United States Patent [19]

Hogan et al.

[11] Patent Number: 5,541,308
[45] Date of Patent: Jul. 30, 1996

[54] NUCLEIC ACID PROBES FOR DETECTION AND/OR QUANTITATION OF NON-VIRAL ORGANISMS

[75] Inventors: James J. Hogan; Richard D. Smith, both of San Diego; Jo A. Kop, San Marcos; Sherrol H. McDonough, San Diego, all of Calif.

[73] Assignee: Gen-Probe Incorporated, San Diego, Calif.

[21] Appl. No.: 200,866

[22] Filed: Feb. 22, 1994

Related U.S. Application Data

[63] Continuation of Ser. No. 806,929, Dec. 11, 1991, abandoned, which is a continuation of Ser. No. 295,208, filed as PCT/US87/03009, Nov. 24, 1987 published as WO88/03957, Jun. 2, 1998, abandoned, which is a continuation-in-part of Ser. No. 83,542, Aug. 7, 1987, abandoned, which is a continuation-in-part of Ser. No. 934,244, Nov. 24, 1986, abandoned.

[51] Int. Cl.⁶ .............................. C07H 21/04; C12Q 1/68
[52] U.S. Cl. .................... 536/23.1; 435/6; 435/91.1; 435/91.2; 435/810; 436/501; 436/63; 536/22.1; 536/24.1; 536/24.3; 536/24.31; 536/24.32; 536/24.33; 935/77; 935/78
[58] Field of Search .................... 435/6, 91.1, 91.2, 435/810; 436/501, 63; 536/22.1, 23.1, 24.1, 24.31–24.33; 935/77, 78

[56] References Cited

U.S. PATENT DOCUMENTS

| | | | |
|---|---|---|---|
| 3,755,086 | 8/1973 | Heimer | 195/103.5 R |
| 3,930,956 | 1/1976 | Juni | 195/103.5 R |
| 4,033,143 | 7/1977 | Juni | 195/100 |
| 4,228,238 | 10/1980 | Swanson | 435/32 |
| 4,237,224 | 12/1980 | Cohen et al. | 435/68 |

(List continued on next page.)

FOREIGN PATENT DOCUMENTS

| | | |
|---|---|---|
| 0155359 | 9/1982 | European Pat. Off. . |
| 0079139 | 5/1983 | European Pat. Off. . |
| 0155360 | 9/1985 | European Pat. Off. . |
| 0232085 | 8/1987 | European Pat. Off. . |
| 0245129 | 11/1987 | European Pat. Off. . |

(List continued on next page.)

OTHER PUBLICATIONS

Lane et al., 82 Proc. Natl. Acad. Sci. USA 6955, 1985.
Rogers et al., 82 Proc. Natl. Acad. Sci. USA 1160, 1985.
Brosius et al., 75 Proc. Natl. Acad. Sci., USA 4801, 1978.
Brosius et al., 77 Proc. Natl. Acad. Sci., USA 201, 1980.
Weisburg et al., 167 Journal of Bacteriology 570, 1986.
Kohne, American Clinical Products Review, Nov. 1986.
Razin, 49 Microbiological Reviews 419, 1985.
Crosa et al., 83 Journal of General Microbiology 271, 1974.
9 Clinical Microbiology Newsletter 90, 1987.
Stahl, 4 Biotechnology 623, 1986.

(List continued on next page.)

Primary Examiner—Stephanie W. Zitomer
Assistant Examiner—Ardin H. Marschel
Attorney, Agent, or Firm—Lyon & Lyon

[57] ABSTRACT

A method for preparing probes, as well as several probes for use in qualitative or quantitative hybridization assays are disclosed. The method comprises constructing an oligonucleotide that is sufficiently complementary to hybridize to a region of rRNA selected to be unique to a non-viral organism or group of non-viral organisms sought to be detected, said region of rRNA being selected by comparing one or more variable region rRNA sequences of said non-viral organism or group of non-viral organisms with one or more variable region rRNA sequences from one or more non-viral organisms sought to be distinguished. Hybridization assay probes for *Mycobacterium avium, Mycobacterium intracellulare,* the *Mycobacterium tuberculosis*-complex bacteria, *Mycoplasma pneumoniae, Legionella, Salmonella, Chlamydia trachomatis, Campylobacter, Proteus mirabilis, Enterococcus, Enterobacter cloacae, E. coli,* Pseudomonas group I, *Neisseria gonorrhoeae,* bacteria, and fungi also are disclosed.

25 Claims, 28 Drawing Sheets

U.S. PATENT DOCUMENTS

| | | | |
|---|---|---|---|
| 4,275,149 | 6/1981 | Litman et al. | 435/7 |
| 4,302,204 | 11/1981 | Wahl et al. | 23/230.2 |
| 4,358,535 | 11/1982 | Falkow et al. | 435/5 |
| 4,394,443 | 7/1983 | Weissman et al. | 435/6 |
| 4,416,988 | 11/1983 | Rubin | 435/91 |
| 4,480,040 | 10/1984 | Owens et al. | 436/504 |
| 4,677,054 | 6/1987 | White et al. | 435/6 |
| 4,689,295 | 8/1987 | Taber et al. | 435/6 |
| 4,717,653 | 1/1988 | Webster, Jr. | 435/5 |
| 4,851,330 | 7/1989 | Kohne | 435/6 |
| 5,030,557 | 7/1991 | Hogan et al. | 435/6 |
| 5,087,558 | 2/1992 | Webster, Jr. | 435/5 |
| 5,217,862 | 6/1993 | Barris et al. | 435/6 |
| 5,288,611 | 2/1994 | Kohne | 435/6 |
| 5,348,854 | 9/1994 | Webster, Jr. | 435/6 |
| 5,432,271 | 7/1995 | Barns et al. | 536/24.32 |

FOREIGN PATENT DOCUMENTS

| | | |
|---|---|---|
| 0133671 | 12/1987 | European Pat. Off. |
| 0250662 | 1/1988 | European Pat. Off. |
| 0277237 | 8/1988 | European Pat. Off. |
| 8301073 | 3/1983 | WIPO |
| 8401174 | 3/1984 | WIPO |
| 8402721 | 7/1984 | WIPO |
| 8803957 | 6/1988 | WIPO |
| 18906704 | 7/1989 | WIPO |

OTHER PUBLICATIONS

Brenner et al., 90 Annals of Internal Medicine 656, 1979.
Ludwig and Stackebrandt, 135 Archives of Microbiology 45, 1983.
Brenner et al., 1 Current Microbiology 71, 1978.
Brenner et al., 35 International Journal of Systematic Bacteriology 50, 1985.
Grimont et al., 21 J. Clin. Microbiol. 431, 1985.
Brenner et al., 30 International Journal SB 236, 1980.
1 Bergy's Manual of Systematic Bacteriology 160, 1984.
Festl et al., 52 Applied and Environmental Microbiology 1190, 1986.
Carbon et al., 9 Nucleic Acid Research 2325, 1981.
Colwell et al., 24 International Journal of Systematic Bacteriology 422, 1974.
Brenner, 23 International Journal of Systematic Bacteriology 298, 1973.
Brenner, 1 Bergy's Manual of Systematic Bacteriology 408, 1984.
McCarroll et al., 22 Biochemistry 5858, 1983.
Veldman et al., 9 Nucleic Acids Research 6935, 1981.
Kilpper–Balz et al., 7 Current Microbiology 245, 1982.
Kilpper–Balz and Schleifer, 10 FEMS Microbiology Letters 357, 1981.
Schleifer and Kilpper–Balz, 34 International Journal of Systematic Bacteriology 31, 1984.
Harvey and Greenwood, 33 International Journal of Systematic Bacteriology 275, 1983.
Lau et al., 447 System Appl. Microbiol. 1987.
Baess 91 Adv. Path. Microbiol. Immunol. Scand. Sect. B 201, 1983.
Imaeda, 35 International Journal of Systematic Bacteriology 147, 1985.
Baess and Bentzon, 86 Acta Pat. Microbiol. Scand. Sect. B 71, 1978.
Drake et al., 25 Journal Clinical Microbiology, 1987.
Stackebrandt and Schleifer, in Biological Biochemical, Biochemical Aspects of Actinomycetes 485, 1984.
Goodfellow and Minnikin, In The Mycobacteria, Kubica and Wayne, eds. Dekker, 1984.
Mordarski et al., 118 Journal of General Microbiology 313, 1980.
Goodfellow and Wayne, in 1 The Biology of the *Mycobacteria* 476, 1982.
Baess, 90 Acta Path. Microbiol. Immunol. Scand. Sect. B 371, 1982.
Bradley, 113 Journal of Bacteriology 645, 1973.
Rogers et al., 82 Proc. Natl. Acad. Sci. USA 1160, 1985.
Yogev and Razin, 36 International Journal of Systematic Bacteriology 426, 1986.
Razin et al., 135 Ann. Microbiol. 9, 1984.
Gobel et al., 133 Journal of General Microbiology 1969, 1987.
Gobel, 226 Science 1211, 1984.
Razin, 49 Microbiol. Rev. 437, 1985.
Jones and Collins, Bergy's Manual of Systematic Bacteriology 1261, 1986.
Kingsburg (1967) J. of Bacteriology, vol. 94, pp. 870–874.
International Search Report for International Appln. No. PCT/US87/03009, Jun. 2, 1988.
Amikam et al., "Mycoplasmas (Mollicutes) Have a Low Number of rRNA Genes," *Journal of Bacteriology* 158:376–378 (1984).
Amikam et al., "Ribosomal RNA genes in Mycoplasma," *Nucleic Acids Research* 10:4215–4222 (1982).
Bahareen et al., "Complementary DNA—25S ribosomal RNA hybridization: an improved method for phylogenetic studies," *Can. J. Microbiol.* 29:546–551 (1983).
Baharaeen, "The evolution of antarctic yeasts," *Ph.D. Thesis: Oklahoma State University; Diss. Abs. Int.* 43.19B:3138–3297 (1982).
Bailey and Scott, *Diagnostic Microbiology*, 4th ed. (St. Louis: The C. V. Mosby Company, 1974) 327–328.
Balch et al., "An Ancient Divergence among the Bacteria," *J. Mol. Evol.* 9:305–311 (1977).
Balch et al., "Methanogens: Reevaluation of a Unique Biological Group," *Microbiological Reviews* 43:260–296 (1979).
Barry et al., "The 16s/23s Ribosomal Spacer Region as a Target for DNA Probes to Identify Eubacteria," *PCR Methods and Application* 81:51–56 (1991).
Baumlein et al., "The Basic Repeat Unit of a *Chlronomus Balbiani* Ring Gene, " *Nucleic Acids Research* 10:3893–3904 (1982).
Bendich and McCarthy, "Ribosomal RNA Homologies among Distantly Related Organisms," *Proc. Natl. Acad. Sci.* 65:349–356 (1970).
Bicknell and Douglas, "Nucleic Acid Homologies Among Species of *Saccharomyces*," *Journal of Bacteriology* 101:505–512 (1970).
Blair et al., "Unfolded 30 S Ribosomal Subunits," *Biophysical Chemistry* 14:81–89 (1981).
Bohnert et al., "Homologies Among Ribosomal RNA and Messenger RNA Genes in Chloroplasts, Mitochondria and *E. coli*," *Molecular Gene Genetics* 179:539–545 (1980).
Bonen et al., "Cyanobacterial evolution: results of 16S ribosomal ribonucelic acid sequence analysis," *Can. J. Biochem.* 57:8797–888 (1979).
Brenner et al., "Conservation of Transfer Ribonuclei Acid and 5S Ribonucleic Acid Cistrons in *Enterobacteriaceae*" *Journal of Bacteriology* 129:1435–1439 (1977).
Brenner and Falkow, "Molecular Relationships Among Members of The Enterobacteriaceae," *Advances in Genetics* 16:81–118 (1971).
Britten et al., "Analysis of Repeating DNA Sequences by Reassociation," *Methods in Enzymology* eds. Grossman and Moldave (Academic Press:NY 1974) Ch. 29, pp. 363–419.

FIG. 1.

| FIG. 1A. | FIG. 1B. |
|---|---|

FIG. 1A.

| | |
|---|---|
| E.coli | AAUUGAAGAGUUUGAUCAUGGCUCAGAUUGAACGCUGGCGGCAGGCCUAACACAUGCAAGU |
| E.coli | AGUGGCGACGGGUGAGUAAUGUCUGGGAAACUGCCUGAUGGAGGGGGAUAACUACUGGAAA |
| E.coli | GGGGACCUUCGGGCCUCUUGCCAUCGGAUGUGCCCAGAUGGGAUUAGCUAGUAGGUGGGGUA |
| E.coli | GGAUGACCAGCCACACUGGAACUGAGACACGGUCCAGACUCCUACGGGAGGCAGCAGUGGG |
| E.coli | CGCGUGUAUGAAGAAGGCCUUCGGGUUGUAAAGUACUUUCAGCGGGGAGGAAGGAGUAAAG |
| E.coli | CACCGGCUAACUCCGUGCCAGCAGCCGCGGUAAUACGGAGGGUGCAAGCGUUAAUCGGAAUU |
| E.coli | GAUGUGAAAUCCCCGGGCUCAACCUGGGAACUGCAUCUGAUACUGGCAAGCUUGAGUCUCGU |
| E.coli | UAGAGAUCUGGAGGAAUACCGGUGGCGAAGGCGGCCCCCUGGACGAAGACUGACGCUCAGGU |
| E.coli | UAGUCCACGCCGUAAACGAUGUCGACUUGGAGGUUGUGCCCUUGAGGCGUGGCUUCCGGAGC |
| E.coli | AGGUUAAAACUCAAAUGAAUUGACGGGGGCCCGCACAAGCGGUGGAGCAUGUGGUUUAAUUC |
| E.coli | CGGAAGUUUUCAGAGAUGAGAAUGUGCCUUCGGGAACCGUGAGACAGGUGCUGCAUGGCUGU |
| E.coli | AACGAGCGCAACCCUUAUCCUUUGUUGCCAGCGGUCCGGCCGGGAACUCAAAGGAGACUGCC |
| E.coli | AUCAUGGCCCUUACGACCAGGGCUACACACGUGCUACAAUGGCGCAUACAAAGAGAAGCGAC |
| E.coli | UCCGGAUUGGAGUCUGCAACUCGACUCCAUGAAGUCGGAAUCGCUAGUAAUCGUGGAUCAGA |
| E.coli | GCCCGUCACACCAUGGGAGUGGGUUGCAAAAGAAGUAGGUAGCUUAACCUUCGGGAGGGCGC |
| E.coli | CAAGGUAACCGUAGGGGAACCUGCGGUUGGAUCACCUCCUUA |

FIG. 1B.

```
CGAACGGGUAACAGGAAGAAGCUUGCUUCUUUGCUGACG      100
CGGUAGCUAAUACCGCAUAACGUCGCAAGACCAAAGAG       200
ACGGCUCACCUAGGCGACGAUCCCUAGCUGGUCUGAGA       300
AAUAUUGCACAAUGGGCGAAGCCUGAUGCAGCCAUGC        400
UUAAUACCUUUGCUCAUUGACGUUACCCGCAGAAGAAG       500
ACUGGGCGUAAGCGCACGCAGGCGGUUUGUUAAGUCA        600
AGAGGGGGUAGAAUCCAGGUGUAGCGGUGAAAUGCG         700
GCGAAAGCGUGGGGAGCAAACAGGAUUAGAUACCCUGG       800
UAACGCGUUAAGUCGACCGCCUGGGGAGUACGGCCGCA       900
GAUGCAACGCGAAGAACCUUACCUGGUCUUGACAUCCA       1000
CGUCAGCUCGUGUUGUGAAAUGUUGGGUUAAGUCCCGC       1100
AGUGAUAAACUGGAGGAAGGUGGGGAUGACGUCAAGUC       1200
CUCGGCGAGAGCAAGGACCUUCAUAAAGUGCCGUCUAG       1300
AUGCCACGGUGAAUACGUUCCCGGGCCUUGUACACACC       1400
UUACCACUUUGUGAUUCAUGACUGGGGUGAAGUCGUAA       1500
                                             1542
```

FIG. 2.

| FIG.2A. | FIG.2B. |
|---|---|
| FIG.2C. | FIG.2D. |

FIG. 2A.

```
E.coli  GGUUAAGCGACUAAGCGUACACGGUGGAUGCCCUGGCAGUCAGAGGCGAUGAAGGACGUGCU
E.coli  AUAACCGGCGAUUUCCGAAUGGGGAAACCCAGUGUGUUUCGACACACUAUCAUUAACUGAAU
E.coli  CUAAGUACCCCGAGGAAAAGAAAUCAACCGAGAUUCCCCAGUAGCGGGCGAGCGAACGGGGA
E.coli  GCGUCUGGAAAGGCGCGCGAUACAGGGUGACAGCCCCGUACACAAAAUGCACAUGCUGUGA
E.coli  AAUAUGGGGGACCAUCCUCCAAGGCUAAAUACUCCUGACUGACCGAUAGUGAACCAGUACC
E.coli  AAAAAGAACCUGAAACCGUGUACGUACAAGCAGUGGGAGCACGCUUAGGCGUGUGACUGCGU
E.coli  CAAGGUUAACCGAAUAGGGGAGCCGAAGGGAAACCGAGUCUUAACUGGGCGUUAAGUUGCAG
E.coli  GUUGAAGGUUGGGUAACACUAACUGGAGGACCGAACCGACUAAUGUUGAAAAUUAGCGGAU
E.coli  GAUAGCUGGUUCUCCCCGAAAGCUAUUUAGGUAGCGCCUCGUGAAUUCAUCUCCGGGGUAG
E.coli  CCCGAUGCAAACUGCGAAUACCGGAGAAUGUUAUCACGGGAGACACGGCCCAGAGCCAGGAUGUUG
E.coli  AGGUCCCAAGUCAUGGUUAAGUGGGAAACGAUGUGGGAAGGCCCAGACAGCCAGGAUGUUG
E.coli  UCACUGGUCGAGUCGGCCUGCGCGGAAGAUGUAACGGGGCUAAACCAUGCACCGAAGCUGCG
E.coli  UGUAAGCUUGCCUGUGAGGCAUGCUGGAGGUAUCAGAAGUGCGAAUGCUGACA
E.coli  AAGACCAAGGUUCCUGUCCAACGUUAAUCGGGGCAGGGUGAGUCGACCCCUAAGGCGAGGC
```

FIG. 2B.

| | |
|---|---|
| AAUCUGGCGAUAAGGCGUCGGUAGGUUGAUAUGAACCGUU | 100 |
| CCAUAGGUUAAUGAGGCGAACCGGGGAACUGAAACAU | 200 |
| GCAGCCCAGAGCCUGAAUCAGUGUGUUAGUGAA | 300 |
| GCUCGAUGAGUAGGGCGGGACACGUGGUAUCCUGUCUG | 400 |
| GUGAGGGAAAGGCGAAAAGAACCCCGGCGAGGGGAGUG | 500 |
| ACCUUUGUAUAAUGGGUCAGCGACUUAUAUCUGUAG | 600 |
| GGUAUAGACCCGAAACCCGGUGAUCUAGCCAUGGGCAG | 700 |
| GACUUGUGGCUGGGGUGAAAGGCCAAUCAAACCGGGA | 800 |
| AGCACUGUUCGGGUCAAGGGUCAUCCCGACUUACCAA | 900 |
| UCCGUCGUGAAGAGGGAAACAACCCAGACCGCCAGCUA | 1000 |
| GCUUAGAAGCAGCCAUCAUUUAAAGAAAGCGUAAUAGC | 1100 |
| GCAGCGACGCUUAUGCGUUGUGGGUAGGGGAGCGUUC | 1200 |
| UAAGUAACGAUAAAGCGGUAAAAGCCCGCUCGCCGG | 1300 |
| CGAAAGGCGUAGUCGAUGGAAACAGGUUAAUAUUCCU | 1400 |

FIG. 2C.

E.coli  GUACUUGGUGUUACUGCGAAGGGGGACGGAGAAGGCUAUGUUGGCCGGGCGACGGUUGUCC

E.coli  GAAAAUCAAGGCUGAGGCUGUGAUGACGAGGCACUACGCGUGCUGAAGCUGAACAAAUGCCCUGCU

E.coli  GUACCCCAAACCGACACAGGUGUCAGGUAGAGAAUACCAAGGCGUUGAGAGAACUCGGGU

E.coli  AGGCACGCCUGAUAUGUAGGUGAGGUUCCUCGCGAUGGAGCUGAAAUCAGUCGAAGAUACCA

E.coli  AAACACGAAAGUGGACGUAUACGGUGUGACGCCUGCCCGGUGCCGGAAGGUUAAUUGAUGG

E.coli  ACGGGCGCGUAACUAUAACGGUCCUAAGGUAGCGAAAUUCCUUGUCGGGUAAGUUCCGACC

E.coli  CGAGACUCAGUGAAAUUGAACUCGCUGUGAAGAUGCAGUGUACCCGCGGCAAGACGGAAAGA

E.coli  AGCCUUGAUGUGUAGGAUAGGUGGAGGCUUUGAAGUGGACGCCAGUCUGCAUGGAGCCG

E.coli  GUUGACCCGUAAUCCGGGACAGUGUCGGUUGUUGACUGGGGCGGUCUCCU

E.coli  CUGGUCGGACAUCAGGAGGUUAGUGCAAUGGCAUAAGCCAGCUUGACUCGCCAGCCGUGACGGC

E.coli  UUCUGAAUGGAAGGGCCAUCGCUCAACGGAUAAAAGGUACUCCGGGGAUAACAGGCUGAUAC

E.coli  CGAUGUCGGCUCAUCACAUCCUGGGGCUGAAGUAGGUCCCAAGGGUAUGGCUGUUCGCCAUU

E.coli  CAGUUCGUCCCCUAUCUGCCGUGGGCGCUGGAGAACUGAGGGGGGCUGCUCCUAGUACGAGA

E.coli  UGCCAAUGGCACUGCCUGGUAGCUAAAUGCGGAAGAGAUAAGUGCUGAAAGCAUCUAAGCAC

E.coli  GGGUCCUGAAGGAACGUUGAAGACGACGUUGAAGCCGGGAUAAGCCGGGUGUAAGGCCAGCGGAUG

E.coli  CCUU

FIG. 2D.

| | |
|---|---|
| CGGUUAAGCGUGUAGGCUGGUUUCCAGGCAAAUCCG | 1500 |
| UCCAGGAAAAGCCUCUAAGCAUCAGGUAACAUCAAAUC | 1600 |
| GAAGGAACUAGGCAAAAUGGUGCCGUAACUUCGGGAGA | 1700 |
| GCUGGCUGCAACUGUUAUUAAAAACACAGCACUGUGC | 1800 |
| GUUAGCGCAAGCGAAGCUCUUGAUCGAAGCCCCGGUAA | 1900 |
| UGCACGAAUGGCGUAAUGAUGGCCAGGCUGUCUCCACC | 2000 |
| CCCCGUGAACCUUUACUAUAGCUUGACACUGAACAUUG | 2100 |
| ACCUUGAAAUAUACCACCCUUUAAUGUUUGAUGUUCUAAC | 2200 |
| CCUAAAGAGUAACGGAGGAGCACGAAGGUUGGCUAAUC | 2300 |
| GCGAGCAGGUUGCGAAAGCAGGUCAUAGUGAUCCGGUGG | 2400 |
| CGCCCAAGAGUUCAUAUCGACGGCGUGUUGGCACCU | 2500 |
| UAAAGUGUACGCGAGCUGGGGUUUAGAACGUCGUGAGA | 2600 |
| GGACCGGAGUGGACGCAUCACUGGUGUCGGGUUGUCA | 2700 |
| GAAACUUGCCCCGAGAGUUCUCCCUGACCCUUUAA | 2800 |
| CGUUGAGCUAACCGGUACUAAUGAACCUGAGGCUUAA | 2900 |
| | 2904 |

FIG. 3A.

E.coli UGCCUGGCGGCCGUAGCGCGGUGGUCCCACCUGACCCCAUGCCGAACUC

E.coli AGUAGGGAACUGCCAGGCAU

FIG. 3B.

AGAAGUGAAACGCCGUAGCGCCGAUGGUAGUGUGGGGUCUCCCCAUGCGAG 100

| FIG.4A. | FIG.4B. | FIG.4C. |

S.cerevisiae.sc UAUCUGGUUGAUCCUGCCAGUAGUCAUAUGCUUGUCUCAAA
S.cerevisiae.sc UUAAAUCAGUUAUCGUUUAUUUGAUAGUUCCUUUACUACAU
S.cerevisiae.sc GAUGUAUUUAUUAGAUAAAAAAUCAAUGUCUUCGCACUCUU
S.cerevisiae.sc AUUUCUGCCCUAUCAACUUUCGAUGGUAGGAUAGUGGCCUA
S.cerevisiae.sc ACGGCUACCACAUCCAAGGAAGGCAGCAGGCGCGCAAAUUA
S.cerevisiae.sc UUGUAAUUGGAAUGAGUACAAUGUAAAUACCUUAACGAGGA
S.cerevisiae.sc AUUAAAGUUGUUGCAGUUAAAAAGCUCGUAGUUGAACUUUG
S.cerevisiae.sc UGGCUAACCUUGAGUCCUUGUGGCUCUUGGCGAACCAGGAC
S.cerevisiae.sc GGAAUAAUAGAAUAGGACGUUUGGUUCUAUUUUGUUGGUUU
S.cerevisiae.sc GUGAAAUUCUUGGAUUUAUUGAAGACUAACUACUGCGAAAG
S.cerevisiae.sc GAUACCGUCGUAGUCUUAACCAUAAACUAUGCCGACUAGGG
S.cerevisiae.sc GUUCUGGGGGGAGUAUGGUCGCAAAGGCUGAAACUUAAAGG
S.cerevisiae.sc GAAACUCACCAGGUCCAGACACAAUAAGGAUUGACAGAUUG
S.cerevisiae.sc AUUUGUCUGCUUAAUUGCGAUAACGAACGAGACCUUAACCU
S.cerevisiae.sc AAGCCGAUGGAAGUUUGAGGCAAUAACAGGUCUGUGAUGCC
S.cerevisiae.sc GCCGAGAGGUCUUGGUAAUCUUGUGAAACUCCGUCGUGCUG
S.cerevisiae.sc CAGCUUGCGUUGAUUACGUCCCUGCCCUUUGUACACACCGC
S.cerevisiae.sc GCAACUCCAUCUCAGAGCGGAGAAUUUGGACAAACUUGGUC
S.cerevisiae.sc UA

*FIG. 4A.*

GAUUAAGCCAUGCAUGUCUAAGUAUAAGCAAUUUAUACAGUGAAACUGCGAA
GGUAUAACCGUGGUAAUUCUAGAGCUAAUACAUGCUUAAAAUCUCGACCCUU
UGAUGAUUCAUAAUAACUUUUCGAAUCGCAUGGCCUUGUGCUGGCGAUGGUU
CCAUGGUUUCAACGGGUAACGGGGAAUAAGGGUUCGAUUCCGGAGAGGGAGC
CCCAAUCCUAAUUCAGGGAGGUAGUGACAAUAAAUAACGAUACAGGGCCCAU
ACAAUUGGAGGGCAAGUCUGGUGCCAGCAGCCGCGGUAAUUCCAGCUCCAAU
GGCCCGGUUGGCCGGUCCGAUUUUUUCGUGUACUGGAUUUCCAACGGGGCCU
UUUUACUUUGAAAAAAUUAGAGUGUUCAAAGCAGGCGUAUUGCUCGAAUAUA
CUAGGACCAUCGUAAUGAUUAAUAGGGACGGUCGGGGGCAUCGGUAUUCAAU
CGUUUGCCAAGGACGUUUUCGUUAAUCAAGAACGAAAGUUGAGGGAUCGAAG
AUCGGUGGUGUUUUUUAAUGACCCACUCGGUACCUUACGAGAAAUCAAAG
AAUUGACGGAAGGGCACCACCAGGAGUGGAGCCUGCGGCUUAAUUUGACUCA
AGAGCUCUUUCUUGAUUUUGUGGGUGGUGGUGCAUGGCCGUUUCUCAGUUGG
ACUAAAUAGUGGUGCUAGCAUUUGCUGGUUAUCCACUUCUUAGAGGGACUAU
CUUAGAACGUUCUGGGCCGCACGCGCGCUACACUGACGGAGCCAGCGAGUCU
GGGAUAGAGCAUUGUAAUUAUUGCUCUUCAACGAGGAAUUCCUAGUAAGCGC
CCGUCGCUAGUACCGAUUGAAUGGCUUAGUGAGGCCUCAGGAUCUGCUUAGA
AUUUGGAGGAACUAAAAGUCGUAACAAGGUUUCCGUAGGUGAACCUGCGGAA

FIG. 4B.

UGGCUCA 100

UGGAAGA 200

CAUUCAA 300

CUGAGAA 400

UCGGGUC 500

AGCGUAU 600

UUCCUUC 700

UUAGCAU 800

UGUCGAG 900

ACGAUCU 1000

UCUUUGG 1100

ACACGGG 1200

UGGAGUG 1300

CGGUUUC 1400

AACCUUG 1500

AAGUCAU 1600

GAAGGGG 1700

GGAUCAU 1800

| FIG.5A. | FIG.5B. | FIG.5C. |
|---|---|---|
| FIG.5D. | FIG.5E. | FIG.5F. |

FIG. 5A.

| | |
|---|---|
| S.cerevisiae | AAACUUUCAACAACGGAUCUCUUGGUUCUCGCAUCGAUGAAGA |
| S.cerevisiae | UUGGUAUUCCAGGGGGCAUGCCUGUUUGAGCGUCAUUUGUUUG |
| S.cerevisiae | UAGUAACGGCGAGUGAAGCGGCAAAAGCUCAAAUUUGAAAUCU |
| S.cerevisiae | ACGUCAUAGAGGGUGAGCAUCCCGUGUGGCGAGGAGUGCGGUU |
| S.cerevisiae | AAUAUUGGCGAGAGACCGAUAGCGAACAAGUACAGUGAUGGAA |
| S.cerevisiae | UGUUUUGUGCCCUCUGCUCCUUGUGGGUAGGGGAAUCUCGCAU |
| S.cerevisiae | GUGGGAAUACUGCCAGCUGGGACUGAGGACUGCGACGUAAGUC |
| S.cerevisiae | GGGUGUAAAACCCAUACGCGUAAUGAAAGUGAACGUAGGUUGG |
| S.cerevisiae | CGAAAGAUGGUGAACUAUGCCUGAAUAGGGUGAAGCCAGAGGA |
| S.cerevisiae | GAACCAUCUAGUAGCUGGUUCCUGCCGAAGUUUCCCUCAGGAU |
| S.cerevisiae | UCAAACUUUAAAUAUGUAAGAAGUCCUUGUUACUUAAUUGAAC |
| S.cerevisiae | GAGUUAAGGUGCCGGAAUACACGCUCAUCAGACACCACAAAAG |
| S.cerevisiae | CGAAUGAACUAGCCCUGAAAAUGGAUGGCGCUCAAGCGUGUUA |
| S.cerevisiae | GUAAGGUCGGGUCGAACGGCCUCUAGUGCAGAUCUUGGUGGUA |
| S.cerevisiae | AGUCGAUCCUAAGAGAUGGGGAAGCUCCGUUUCAAAGGCCUGA |
| S.cerevisiae | UGAAUGUGGAGACGUCGGCGCGAGCCCUGGGAGGAGUUAUCUU |
| S.cerevisiae | UGCUGGCUCCGGUGCGCUUGUGACGGCCCGUGAAAAUCCACAG |
| S.cerevisiae | UAAUGUAGAUAAGGGAAGUCGGCAAAAUAGAUCCGUAACUUCG |
| S.cerevisiae | GGGGCUUGCUCUGCUAGGCGGACUACUUGCGUGCCUUGUUGUA |
| S.cerevisiae | GAAUCUGACUGUCUAAUUAAAACAUAGCAUUGCGAUGGUCAGA |
| S.cerevisiae | ACGGCGGGAGUAACUAUGACUCUCUUAAGGUAGCCAAAUGCCU |
| S.cerevisiae | GCCAAGGGAACGGGCUUGGCAGAAUCAGCGGGGAAAGAAGACC |

FIG. 5B.

ACGCAGCGAAAUGCGAUACGUAAUGUGAAUUGCAGAAUUCCGUGAAUCAUCG

ACCUCAAAUCAGGUAGGAGUACCCGCUGAACUUAAGCAUAUCAAUAAGCGGA

GGUACCUUCGGUGCCCGAGUUGUAAUUUGGAGAGGGCAACUUUGGGGCCGUU

CUUUGUAAAGUGCCUUCGAAGAGUCGAGUUGUUUGGGAAUGCAGCUCUAAGU

AGAUGAAAAGAACUUUGAAAAGAGAGUGAAAAAGUACGUGAAAUUGUUGAAA

UUCACUGGGCCAGCAUCAGUUUUGGUGGCAGGAUAAAUCCAUAGGAAUGUAG

AAGGAUGCUGGCAUAAUGGUUAUAUGCCGCCCGUCUUGAAACACGGACCAAG

GGCCUCGCAAGAGGUGCACAAUCGACCGAUCCUGAUGUCUUCGGAUGGAUUU

AACUCUGGUGGAGGCUCGUAGCGGUUCUGACGUGCAAAUCGAUCGUCGAAUU

AGCAGAAGCUCGUAUCAGUUUUAUGAGGUAAAGCGAAUGAUUAGAGGUUCCG

GUGGACAUUUGAAUGAAGAGCUUUUAGUGGGCCAUUUUUGGUAAGCAGAACU

GUGUUAGUUCAUCUAGACAGCCGGACGGUGGCCAUGGAAGUCGGAAUCCGCU

CCUAUACUCUACCGUCAGGGUUGAUAUGAUGCCCUGACGAGUAGGCAGGCGU

GUAGCAAAUAUUCAAAUGAGAACUUUGAAGACUGAAGUGGGGAAAGGUUCCA

UUUUAUGCAGGCCACCAUCGAAAGGGAAUCCGGUAAGAUUCCGGAACUUGGA

UUCUUCUUAACAGCUUAUCACCCCGGAAUUGGUUUAUCCGGAGAUGGGGUCU

GAAGGAAUAGUUUUCAUGCUAGGUCGUACUGAUAACCGCAGCAGGUCUCCAA

GGAUAAGGAUUGGCUCUAAGGGUCGGGUAGUGAGGGCCUUGGUCAGACGCAG

GACGGCCUUGGUAGGUCUCUUGUAGACCGUCGCUUGCUACAAUUAACAGAUC

AAGUGAUGUUGACGCAAUGUGAUUUCUGCCCAGUGCUCUGAAUGUCAAAGUG

CGUCAUCUAAUUAGUGACGCGCAUGAAUGGAUUAACGAGAUUCCCACUGUCC

CUGUUGAGCUUGACUCUAGUUUGACAUUGUGAAGAGACAUAGAGGGUGUAGA

| | |
|---|---|
| AAUCUUUGAACGCACAUUGCGCCCC | 120 |
| GGAAAAGAAACCAACCGGAUUGCCU | 240 |
| CCUUGUCUAUGUUCCUUGGAACAGG | 360 |
| GGUGGUAAAUUCCAUCUAAAGCUA | 480 |
| GGGAAGGGCAUUUGAUCAGACAUGG | 600 |
| CUUGCCUCGGUAAGUAUUAUAGCCU | 720 |
| GAGUCUAACGUCUAUGCGAGUGUUU | 840 |
| GAGUAAGAGCAUAGCUGUUGGGACC | 960 |
| UGGGUAUAGGGGCGAAAGACUAAUC | 1080 |
| GGGUCGAAAUGACCUUGACCUAUUC | 1200 |
| GGCGAUGCGGGAUGAACCGAACGUA | 1320 |
| AAGGAGUGUGUAACAACUCACCGGC | 1440 |
| GGAGGUCAGUGACGAAGCCUAGACC | 1560 |
| CGUCAACAGCAGUUGGACGUGGGUU | 1680 |
| UAUGGAUUCUUCACGGUAACGUAAC | 1800 |
| UAUGGCUGGAAGAGGCCAGCACCUU | 1920 |
| GGUGAACAGCCUCUAGUUGAUAGAA | 2040 |
| CGGGCGUGCUUGUGGACUGCUUGGU | 2160 |
| AACUUAGAACUGGUACGGACAAGGG | 2280 |
| AAGAAAUUCAACCAAGCGCGAGUAA | 2400 |
| CUAUCUACUAUCUAGCGAAACCACA | 2520 |
| AUAAGUGGGAGCUUCGGCGCCAGUG | 2640 |

*FIG. 5C.*

S.cerevisiae  AAAUACCACUACCUUUAUAGUUUCUUUACUUAUUCAAUGAAGC

S.cerevisiae  UGGGGAGUUUGGCUGGGGCGGCACAUCUGUUAAACGAUAACGC

S.cerevisiae  GUGUGAAUACAAACCAUUGAAAGUGUGGCCUAUCGAUCCUUUA

S.cerevisiae  AGCGACAUUGCUUUUUGAUUCUUCGAUGUCGGCUCUUCCUAUC

S.cerevisiae  AGACAGGUUAGUUUUACCCUACUGAUGAAUGUUACCAGCAAUA

S.cerevisiae  AAGCACCAUCCGCUGGAUUAUGGCUGAACGCCUCUAAGUCAGA

S.cerevisiae  UGAACCAUAGCAGGCUAGCAACGGUGCACUUGGCGGAAAGGCC

S.cerevisiae  GGUAUUGUAAGCGGUAGAGUAGCCUUGUUGUUACGAUCUGCUG

S.cerevisiae

S.cerevisiae

FIG. 5D.

GGAGCUGGAAUUCAUUUUCCACGUUCUAGCAUUCAAGGUCCCAUUCGGGGCU

AGAUGUCCUAAGGGGGGCUCAUGGAGAACAGAAAUCUCCAGUAGAACAAAAG

GUCCCUCGGAAUUUGAGGCUAGAGGUGCCAGAAAAGUUACCACAGGGAUAAC

AUACCGAAGCAGAAUUCGGUAAGCGUUGGAUUGUUCACCCACUAAUAGGGAA

GUAAUUGAACUUAGUACGAGAGGAACAGUUCAUUCGGAUAAUUGGUUUUUGC

AUCCAUGCUAGAACGCGGUGAUUUCUUUGCUCCACACAAUAUAGAUGGAUAC

UUGGGUGCUUGCUGGCGAAUUGCAAUGUCAUUUUGCGUGGGGAUAAAUCAUU

AGAUUAAGCCUUUGUUGUCUGAUUUGU

*FIG. 5E.*

GAUCCGGGUUGAAGACAUUGUCAGG  2760

GGUAAAGCCCCUUAGUUUGAUUUCA  2880

UGGCUUGUGGCAGUCAAGCGUUCAU  3000

CAUGAGCUGGGUUUAGACCGUCGUG  3120

GGCUGUCUGAUCAGGCAUUGCCGCG  3240

GAAUAAGGCGUCCUUGUGGCGUCGC  3360

UGUAUACGACUUAGAUGUACAACGG  3480

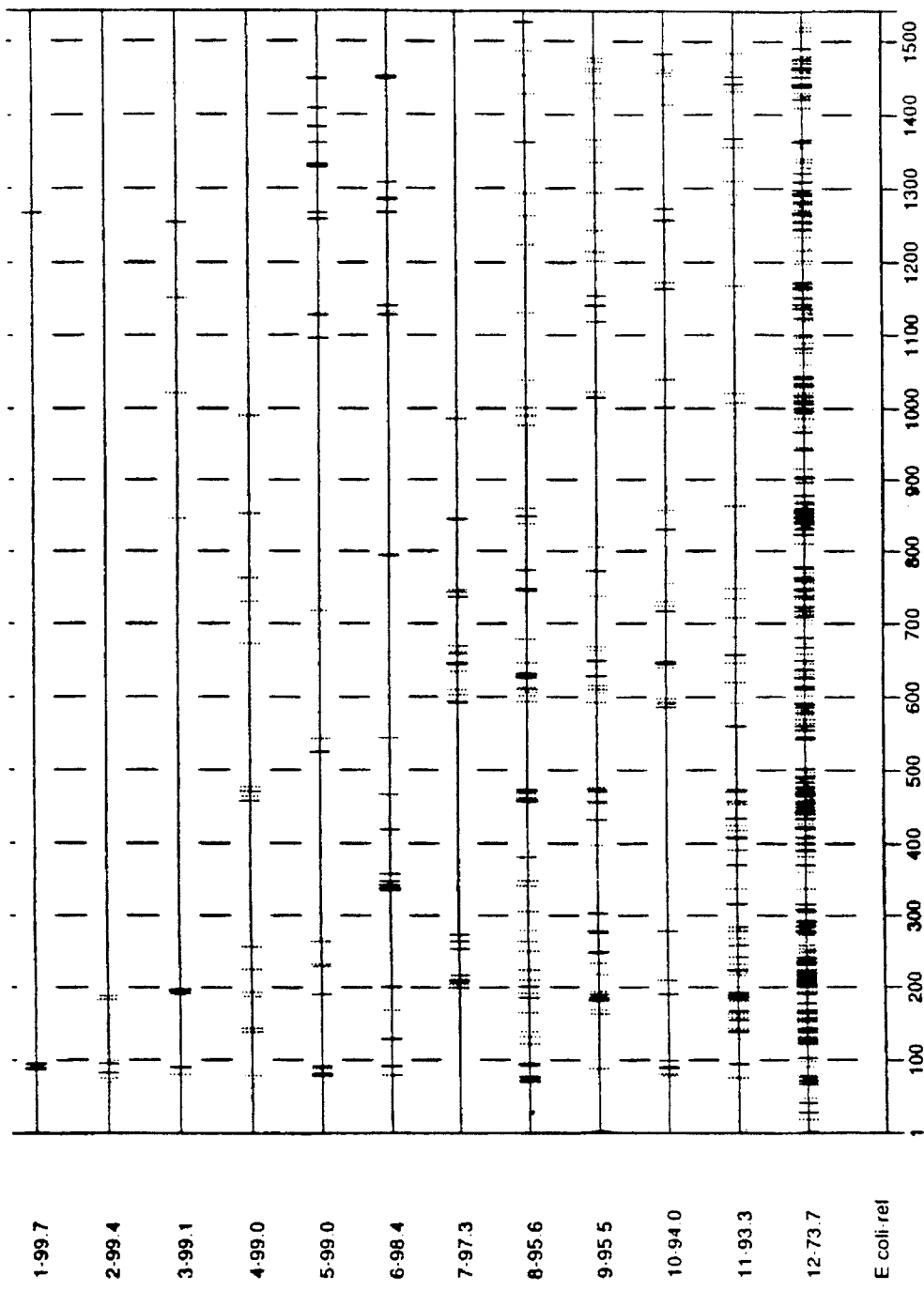

NUCLEIC ACID PROBES FOR DETECTION AND/OR QUANTITATION OF NON-VIRAL ORGANISMS

This application is a continuation of Hogan et al., U.S. Ser. No. 07/806,929, filed Dec. 11, 1991, abandoned entitled "Nucleic Acid Probes For Detection And/Or Quantitation Of Non-Viral Organisms," abandoned, which is a continuation of Hogan et al., U.S. Ser. No. 07/295,208, filed Dec. 9, 1988, abandoned, which is the national filing of Hogan et al., PCT/US87/03009, filed Nov. 24, 1987, published as WO88/03957, Jun. 2, 1988, which is a continuation-in-part of Hogan et al., U.S. Ser. No. 07/083,542, filed Aug. 7, 1987, abandoned, which is a continuation-in-part of Hogan et al., U.S. Ser. No. 06/934,244, filed Nov. 24, 1986, abandoned.

BACKGROUND OF THE INVENTION

1. Field of the Invention

The inventions described and claimed herein relate to probes and assays based on the use of genetic material such as RNA. More particularly, the inventions relate to the design and construction of nucleic acid probes and hybridization of such probes to genetic material of target non-viral organisms in assays for detection and/or quantitation thereof in test samples of, e.g., sputum, urine, blood and tissue sections, food, soil and water.

2. Introduction

Two single strands of nucleic acid, comprised of nucleotides, may associate ("hybridize") to form a double helical structure in which the two polynucleotide chains running in opposite directions are held together by hydrogen bonds (a weak form of chemical bond) between pairs of matched, centrally located compounds known as "bases." Generally, in the double helical structure of nucleic acids, for example, the base adenine (A) is hydrogen bonded to the base thymine (T) or uracil (U) while the base guanine (G) is hydrogen bonded to the base cytosine (C). At any point along the chain, therefore, one may find the base pairs AT or AU, TA or UA, GC, or CG. One may also find AG and GU base pairs in addition to the traditional ("canonical") base pairs. Assuming that a first single strand of nucleic acid is sufficiently complementary to a second and that the two are brought together under conditions which will promote their hybridization, double stranded nucleic acid will result. Under appropriate conditions, DNA/DNA, RNA/DNA, or RNA/RNA hybrids may be formed.

Broadly, there are two basic nucleic acid hybridization procedures. In one, known as "in solution" hybridization, both a "probe" nucleic acid sequence and nucleic acid molecules from a test sample are free in solution. In the other method, the sample nucleic acid is usually immobilized on a solid support and the probe sequence is free in solution.

A probe may be a single strand nucleic acid sequence which is complementary in some particular degree to the nucleic acid sequences sought to be detected ("target sequences"). It may also be labelled. A background description of the use of nucleic acid hybridization as a procedure for the detection of particular nucleic acid sequences is described in U.S. application Ser. No. 456,729, entitled "Method for Detection, Identification and Quantitation of Non-Viral Organisms," filed Jan. 10, 1983 (Kohne I, now issued as U.S. Pat. No. 4,851,330), and U.S. application Ser. No. 655,365, entitled "Method For Detecting, Identifying and Quantitating Organisms and Viruses," filed Sep. 4, 1984 (Kohne II, now issued as U.S. Pat. No. 5,288,611), both of which are incorporated by reference, together with all other applications cited herein.

Also described in those applications are methods for determining the presence of RNA-containing organisms in a sample which might contain such organisms, comprising the steps of bringing together any nucleic acids from a sample and a probe comprising nucleic acid molecules which are shorter than the rRNA subunit sequence from which it was derived and which are sufficiently complementary to hybridize to the rRNA of one or more non-viral organisms or groups of non-viral organisms, incubating the mixture under specified hybridization conditions, and assaying the resulting mixture for hybridization of the probe and any test sample rRNA. The invention is described to include using a probe which detects only rRNA subunit subsequences which are the same or sufficiently similar in particular organisms or groups of organisms and is said to detect the presence or absence of any one or more of those particular organisms in a sample, even in the presence of many non-related organisms.

We have discovered and describe herein a novel method and means for designing and constructing DNA probes for use in detecting unique rRNA sequences in an assay for the detection and/or quantitation of any group of non-viral organisms. Some of the inventive probes herein may be used to detect and/or quantify a single species or strain of non-viral organism and others may be used to detect and/or quantify members of an entire genus or desired phylogenetic grouping.

SUMMARY OF THE INVENTION

In a method of probe preparation and use, a single strand deoxyoligonucleotide of particular sequence and defined length is used in a hybridization assay to determine the presence or amount of rRNA from particular target non-viral organisms to distinguish them from their known closest phylogenetic neighbors. Probe sequences which are specific, respectively, for 16S rRNA variable subsequences of *Mycobacterium avium*, *Mycobacterium intracellulare* and the *Mycobacterium tuberculosis*-complex bacteria, and which do not cross react with nucleic acids from each other, or any other bacterial species or respiratory infectious agent, under proper stringency, are described and claimed. A probe specific to three 23S rRNA variable region subsequences from the *Mycobacterium tuberculosis*-complex bacteria is also described and claimed, as are rRNA variable region probes useful in hybridization assays for the genus Mycobacterium (16S 23S rRNA specific), *Mycoplasma pneumoniae* (5S and 16S rRNA-specific), *Chlamydia trachomatis* (16S and 23S rRNA specific), *Enterobacter cloacae* (23S rRNA specific), *Escherichia coli* (16S rRNA specific), Legionella (16S and 23S rRNA specific), Salmonella (16S and 23S rRNA specific), Enterococci (16S rRNA specific), *Neisseria gonorrhoeae* (16s rRNA specific), Campylobacter (16S rRNA specific), *Proteus mirabilis* (23S rRNA specific), Pseudomonas (23S rRNA specific), fungi (18S and 28S rRNA specific), and bacteria (16S and 23S rRNA specific).

In one embodiment of the assay method, a test sample is first subjected to conditions which release rRNA from any non-viral organisms present in that sample. rRNA is single stranded and therefore available for hybridization with sufficiently complementary genetic material once so released. Contact between a probe, which can be labelled, and the rRNA target may be carried out in solution under conditions which promote hybridization between the two strands. The reaction mixture is then assayed for the presence of hybridized probe. Numerous advantages of the present method for the detection of non-viral organisms over prior art techniques, including accuracy, simplicity, economy and speed will appear more fully from the detailed description which follows.

BRIEF DESCRIPTION OF THE DRAWING

Figures 1, 1A:
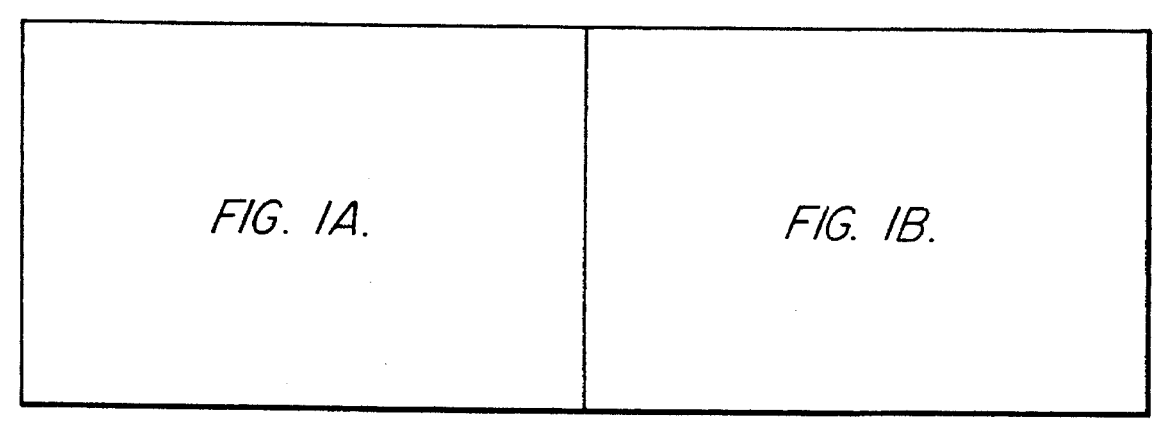

FIGS. 1, 1A and 1B illustrate the primary structure of bacterial 16S rRNA for *Escherichia coli*, depicting standard reference numbers for bases.

FIGS. 1a and 1b provide a chart of the primary structure of bacterial 16S rRNA for *Escherichia coli*, depicting standard reference numbers for bases, and FIG. 1 shows the orientation of FIG. 1a to FIG. 1b.

FIGS. 2, 2A, 2B, 2C and 2D, illustrate the primary structure of bacterial 23S rRNA for *Escherichia coli*, depicting standard reference numbers for bases.

FIGS. 2a, 2b, 2c 2d, provide a chart of the primary structure of bacterial 23S rRNA for *Escherichia coli*, depicting standard reference numbers, and FIG. 2 shows the orientation of FIGS. 2a, 2b, 2c and 2d.

FIGS. 3, 3A and 3B illustrate the primary structure of bacterial 5S rRNA for *Escherichia coli*, depicting standard reference numbers for bases.

FIGS. 3a and 3b provide a chart of the primary structure of bacterial 5S rRNA for *Escherichia coli*, depicting standard reference numbers, and FIG. 3 shows the orientation of FIGS. 3a and 3b.

Figures 4, 4A:
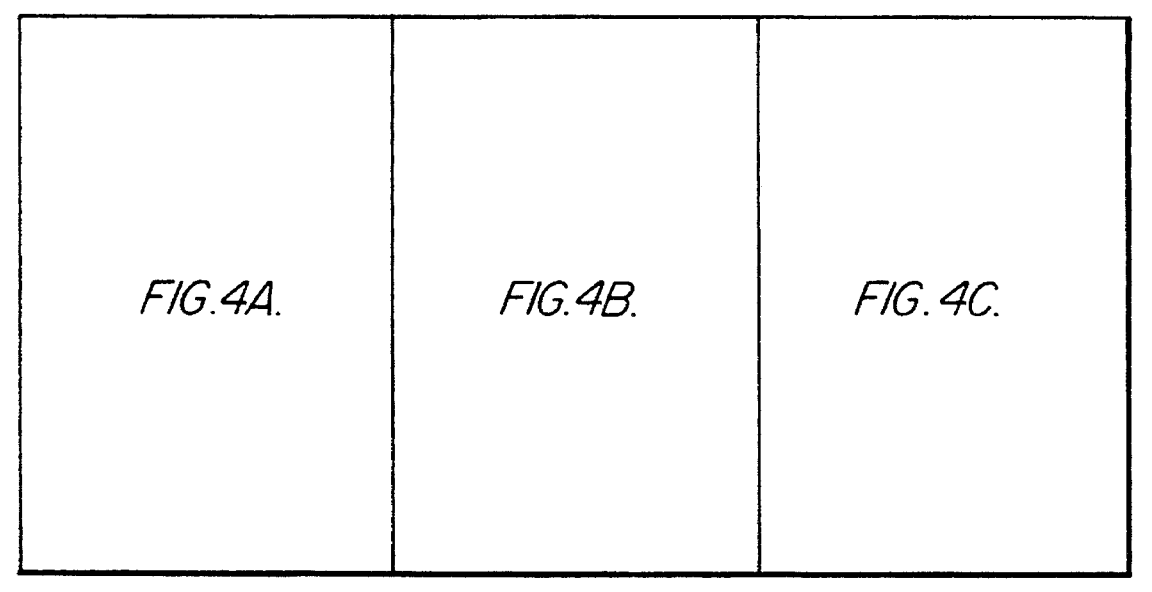

FIGS. 4, 4A, 4B and 4C illustrate the primary structure for the 18S rRNA for *Saccharomyces cerevisiae*, depicting standard reference numbers for bases.

FIGS. 4a, 4b and 4c, provide a chart of the primary structure for the 18S rRNA for *Saccharomyces cerevisiae*, depicting standard reference numbers, and FIG. 4 shows the orientation of FIGS. 4a, 4b and 4c.

Figures 5, 5A, 5D:
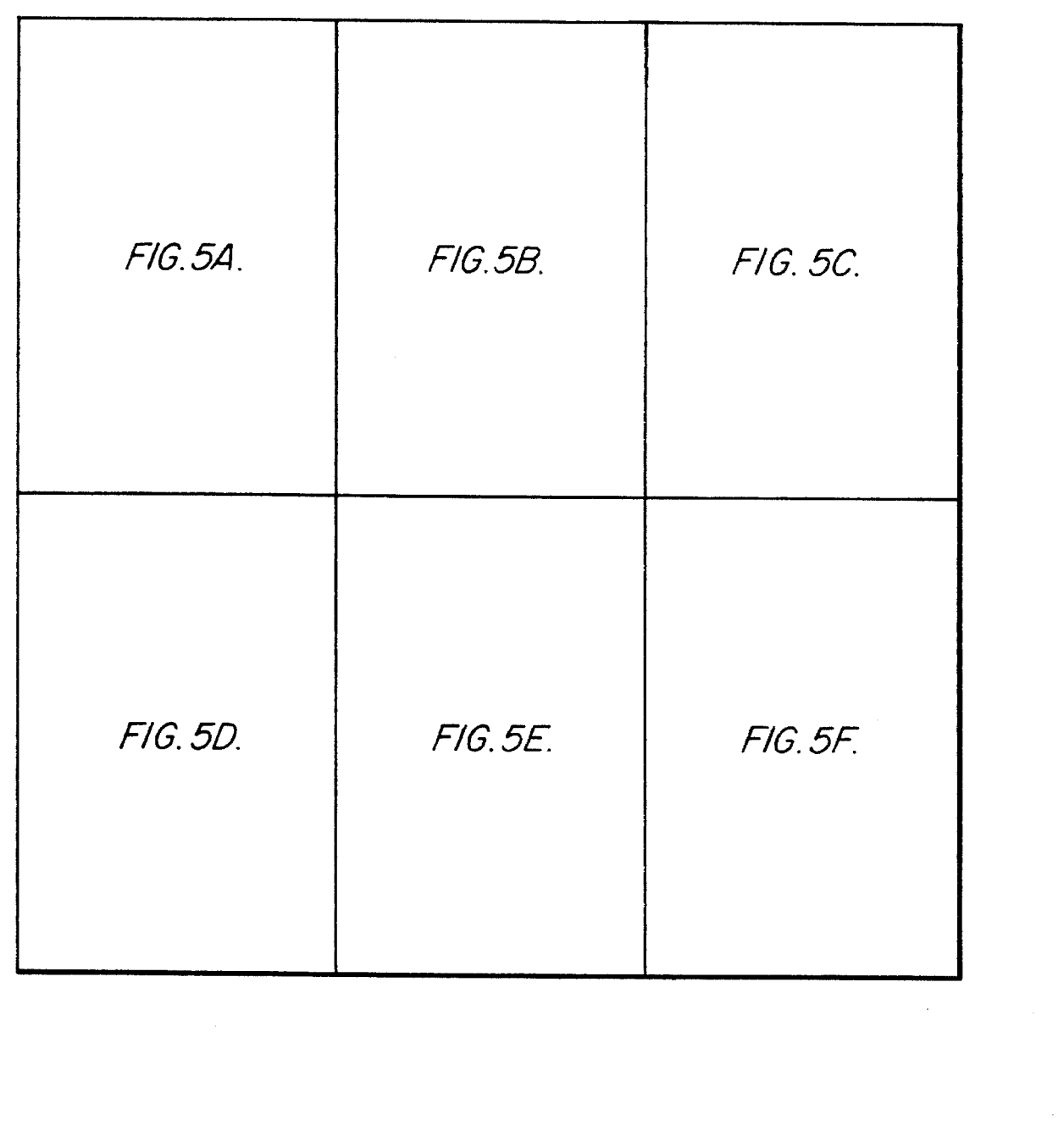

FIGS. 5A to 5F illustrate the primary structure for the 28S rRNA for *Saccharomyces cerevisiae*, depicting standard reference numbers for bases.

FIGS. 5a to 5f, provide a chart of the primary structure for the 18S rRNA for *Saccharomyces cerevisiae*, depicting standard reference numbers, and FIG. 5 shows the orientation of FIGS. 5a to 5f.

FIG. 6 is a diagram showing the locations in the 16S rRNA (using *E. coli* reference numbers) which differ between 12 different sets of related organisms. In Example 1, for example, 99.7 refers to the difference in 16s rRNA between *Clostridium botulinium* and Clostridium subterminale.

Figure 3:
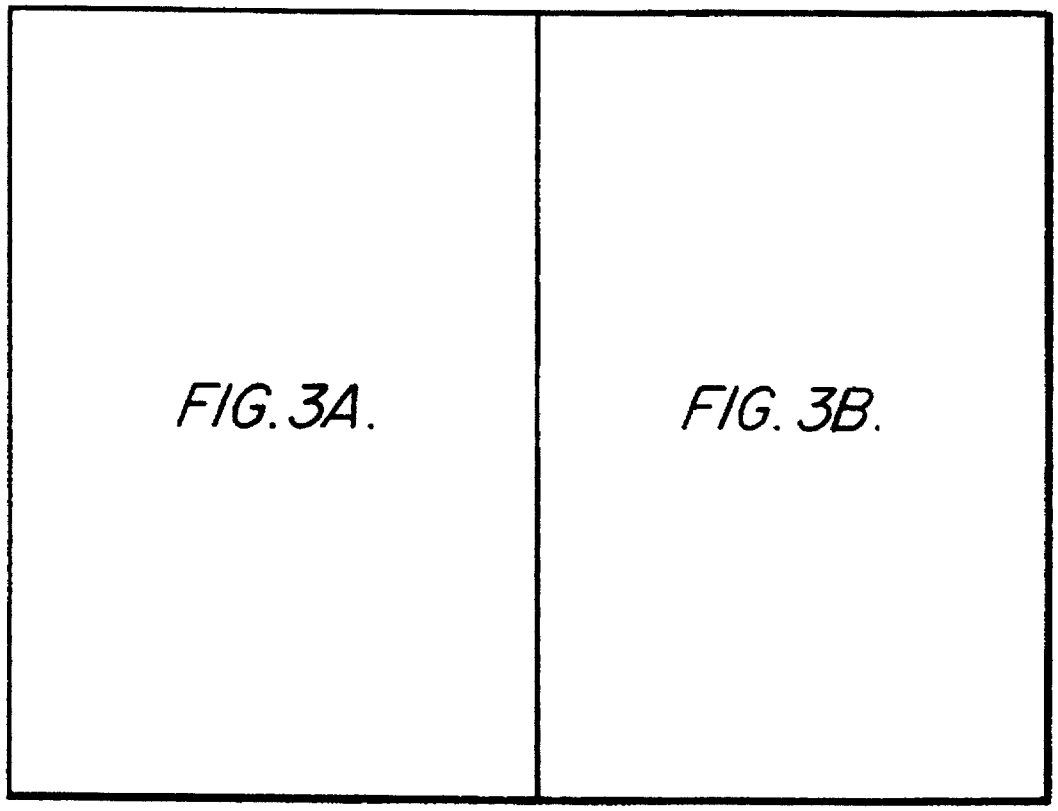

FIG bacteria: members of the phylogenetic group eubacteria, which is considered one of the three primary kingdoms.

Tm: temperature at which 50% of the probe is converted from the hybridized to the unhybridized form.

thermal stability: Temperature at which 50% of the probe:target hybrids are converted to the single stranded form. Factors which affect the thermal stability can affect probe specificity and therefore, must be controlled. Whether a probe sequence is useful to detect only a specific type of organism depends largely on the thermal stability difference between probe:target hybrids ("P:T") and probe:nontarget hybrids ("P:NT"). In designing probes the Tm P:T minus the Tm P:NT should be as large as possible.

In addition to a novel method for selecting probe sequences, we have discovered that it is possible to create a DNA probe complementary to a particular rRNA sequence obtained from a single type of target microorganism and to successfully use that probe in a non-cross reacting assay for the detection of that single microorganism, even in the presence of its known, most closely related taxonomic or phylogenetic neighbors. With the exception of viruses, all prokaryotic organisms contain rRNA molecules including 5S rRNA, 16S rRNA, and a larger rRNA molecule known as 23S rRNA. Eukaryotes are known to have 5.0S, 5.8S, 18S and 28S rRNA molecules or analogous structures. (The term "16S like" sometimes is used to refer to the rRNA found in the small ribosomal subunit, including 18S and 17S rRNA. Likewise the term "23S like" rRNA sometimes is used to refer to the rRNA found in the large ribosomal subunit. 5.8S rRNA is equivalent to the 5' end of the 23S like rRNA.) These rRNA molecules contain nucleotide sequences which are highly conserved among all organisms thus far examined. There are known methods which allow a significant portion of these rRNA sequences to be determined. For example, complementary oligonucleotide primers of about 20–30 bases in length can be hybridized to universally conserved regions in purified rRNA that are specific to the 5S, 16S, or 23S subunits and extended with the enzyme reverse transcriptase. Chemical degradation or dideoxynucleotide- terminated sequencing reactions can be used to determine the nucleotide sequence of the extended product. Lane, D. J. et al., *Proc. Nat'l Acad. Sci. USA* 82, 6955–6959 (1985).

In our invention, comparison of one or more sequenced rRNA variable regions from a target organism to one or more rRNA variable region sequences from a closely related bacterial species is utilized to select a sequence unique to the rRNA of the target organism. rRNA is preferable to DNA as a probe target because of its relative abundance and stability in the cell and because of its patterns of phylogenetic conservation.

Notwithstanding the highly conserved nature of rRNA, we have discovered that a number of regions of the rRNA molecule which can vary in sequence, can vary even between closely related species and can, therefore, be utilized to distinguish between such organisms. Differences in the rRNA molecule are not distributed randomly across the entire molecule, but rather are clustered into specific regions. The degree of conservation also varies, creating a unique pattern of conservation across the ribosomal RNA subunits. The degree of variation and the distribution thereof, can be analyzed to locate target sites for diagnostic probes. This method of probe selection may be used to select more than one sequence which is unique to the rRNA of a target organism.

We have identified variable regions by comparative analysis of rRNA sequences both published in the literature and sequences which we have determined ourselves using procedures known in the art. We use a Sun Microsystems (TM) computer for comparative analysis. The compiler is capable of manipulating many sequences of data at the same time. Computers of this type and computer programs which may be used or adapted for the purposes herein disclosed are commercially available.

Generally, only a few regions are useful for distinguishing between closely related species of a phylogenetically conserved genus, for example, the region 400–500 bases from the 5' end of the 16S rRNA molecule. An analysis of closely related organisms (FIGS. 6, 7 and 8) reveals the specific positions (variable regions) which vary between closely related organisms. These variable regions of rRNA molecules are the likely candidates for probe design.

Figure 7:
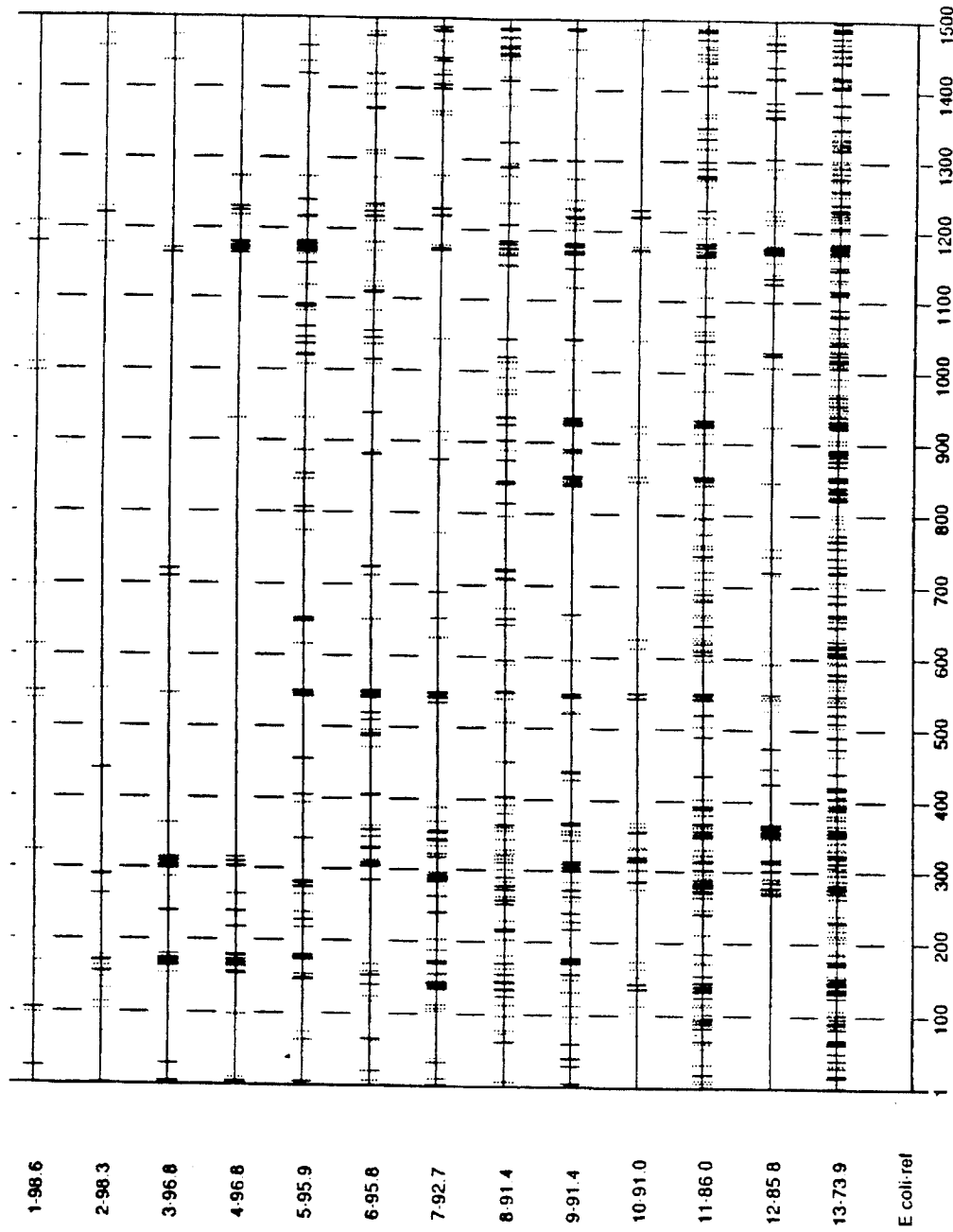
FIG. 7 is a diagram showing the locations in the first 1500 bases of 23S rRNA (using *E. coli* reference numbers) which differ between 12 different sets of related organisms.
Figure 8:
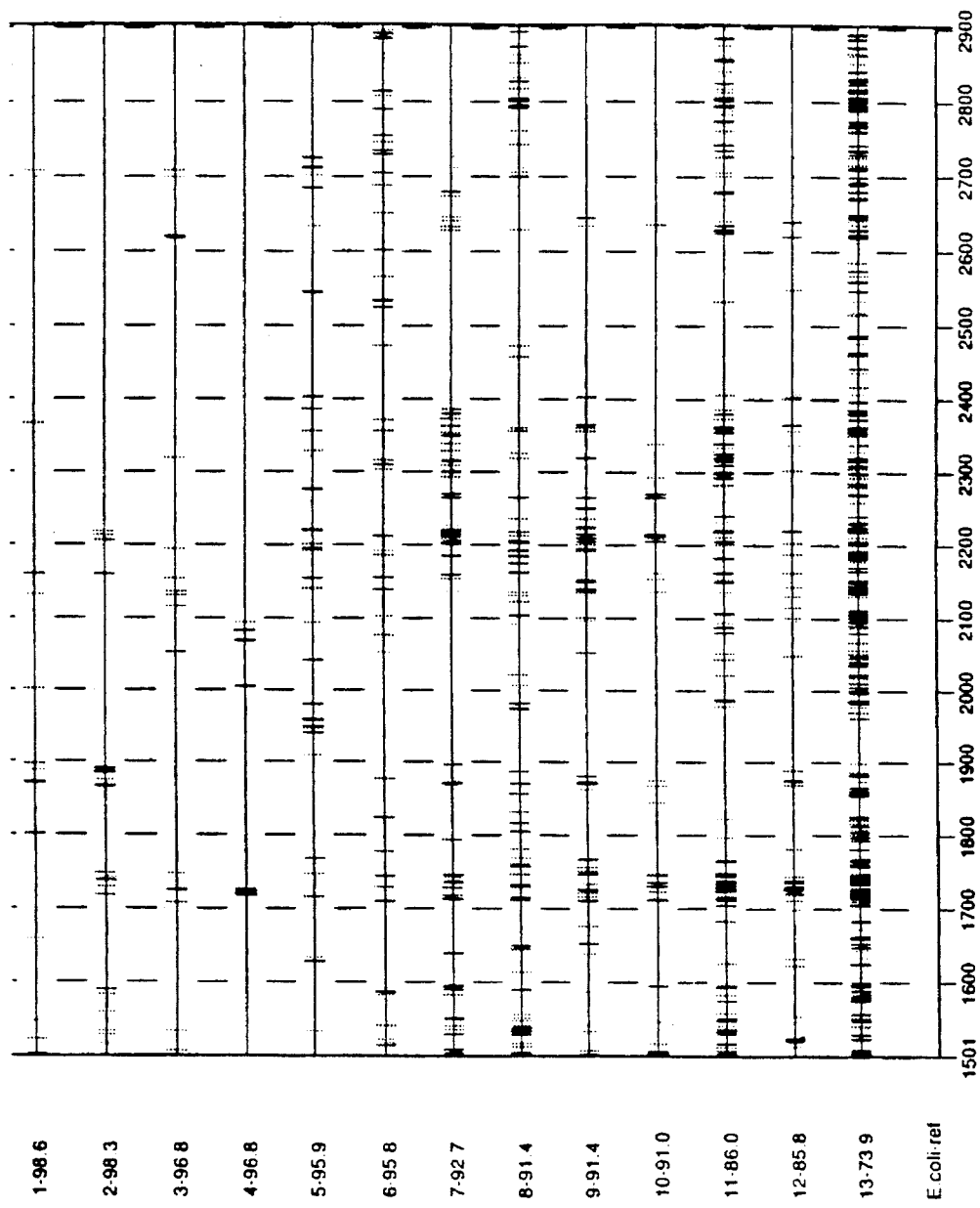

FIGS. 6, 7 and 8 display the variations in 16S and 23S rRNA's between two different bacteria with decreasing amounts of similarity between them. Closer analysis of these figures reveals some subtle patterns between these closely related organisms. In all cases studied, we have seen sufficient variation between the target organism and the closest phylogenetic relative found in the same sample to design the probe of interest. Moreover, in all cases studied to date, the per cent similarity between the target organism (or organisms) and the closest phylogenetically related organisms found in the same sample has been between 90% and 99%. Interestingly, there was enough variation even between the rRNA's of Neisseria's gonorrhoeae and meningitidis (See Example 21) to design probes despite the fact that DNA:DNA homology studies suggested these two species might actually be one and the same.

These figures also show that the differences are distributed across the entire 16S and 23S rRNA's. Many of the differences, nonetheless, cluster into a few regions.

These locations in the rRNA are good candidates for probe design, with our current assay conditions. We also note that the locations of these increased variation densities usually are situated in the same regions of the 16S and 23S rRNA for comparable per cent similarity values. In this manner, we have observed that certain regions of the 16S and 23S rRNA are the most likely sites in which significant variation exists between the target organism and the closest phylogenetic relatives found in a sample. We have disclosed and claimed species specific probes which hybridize in these regions of significant variation between the target organism and the closest phylogenetic relative found in a sample.

Figure 9:
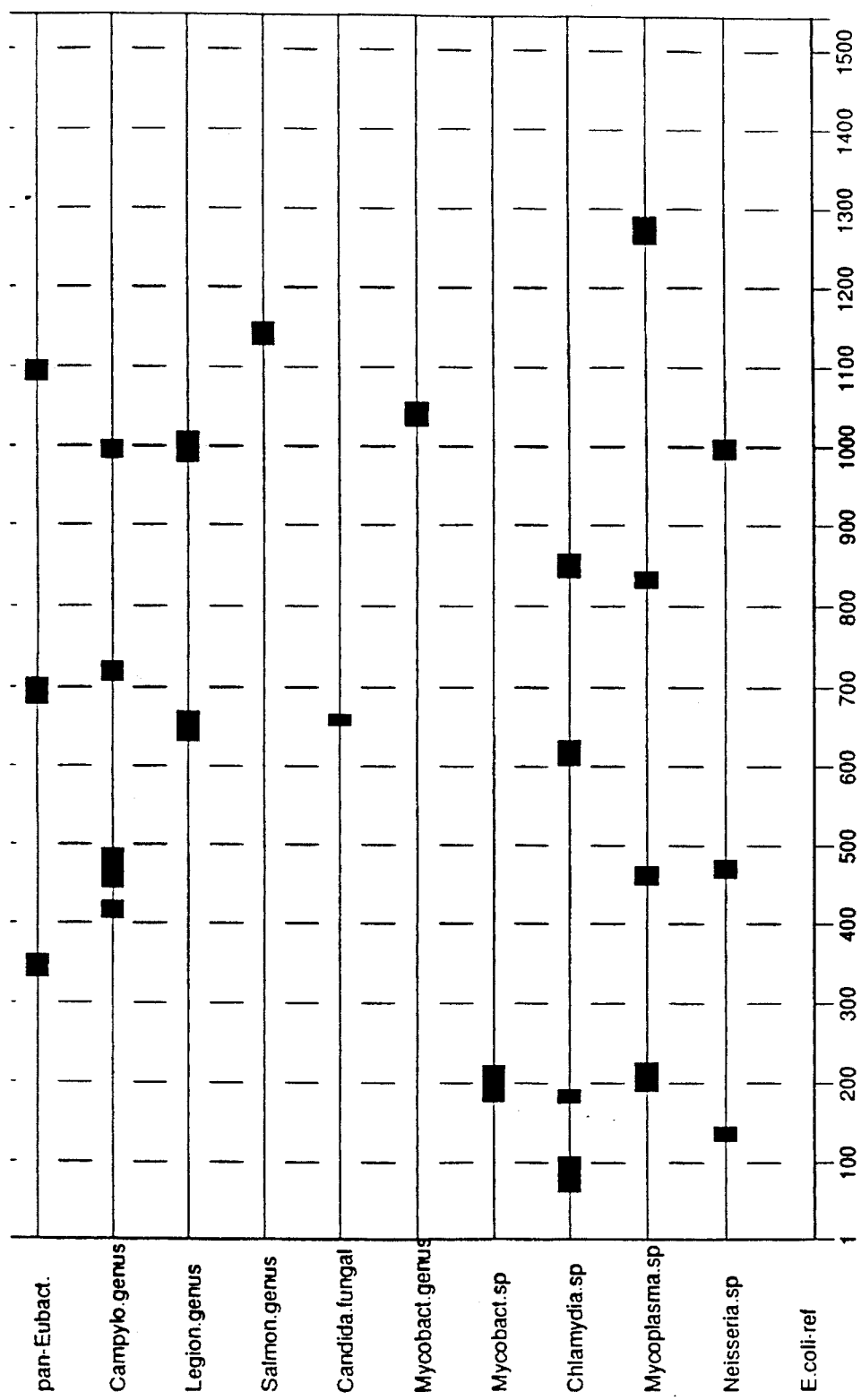
Figure 10:
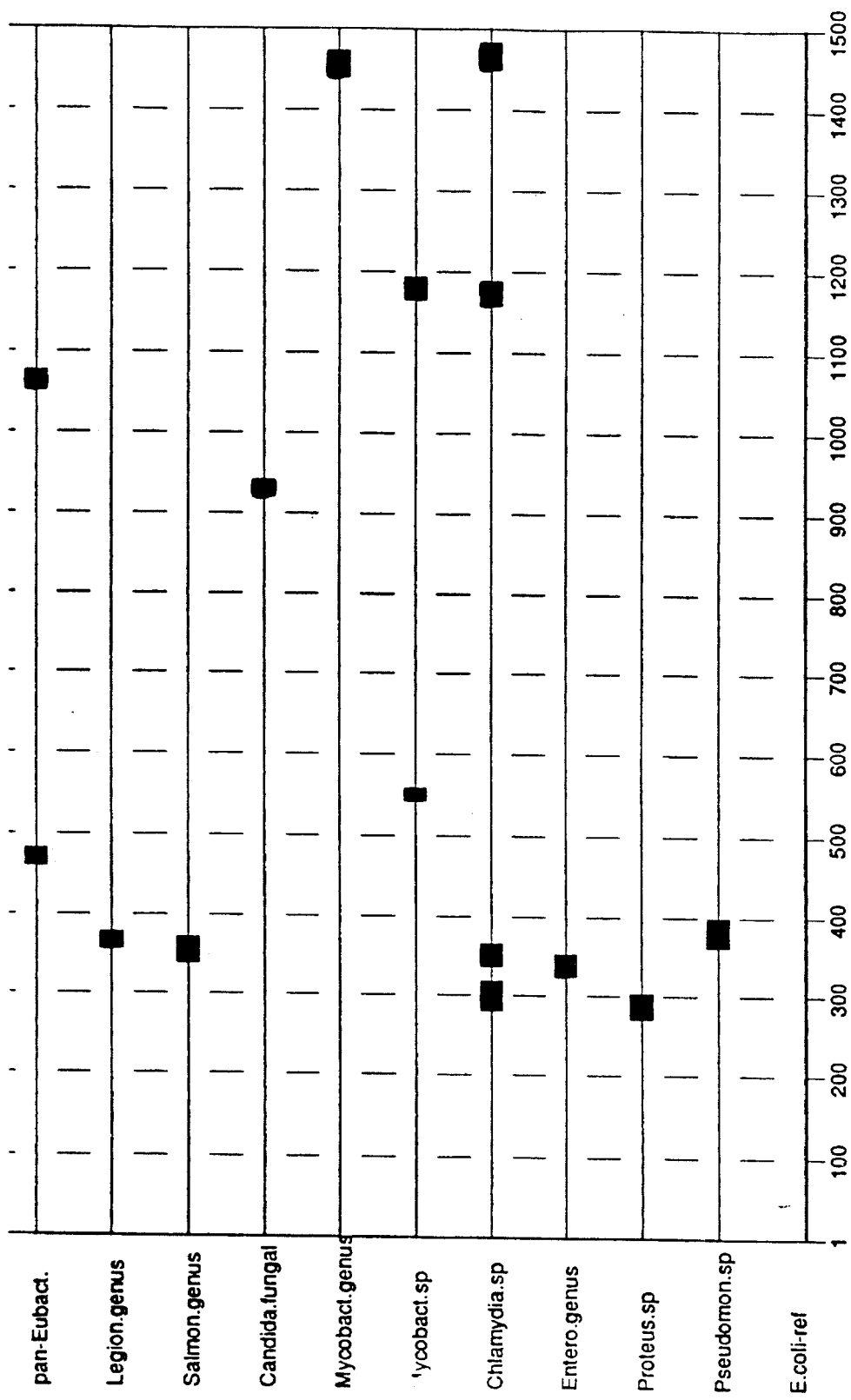
Figure 11:
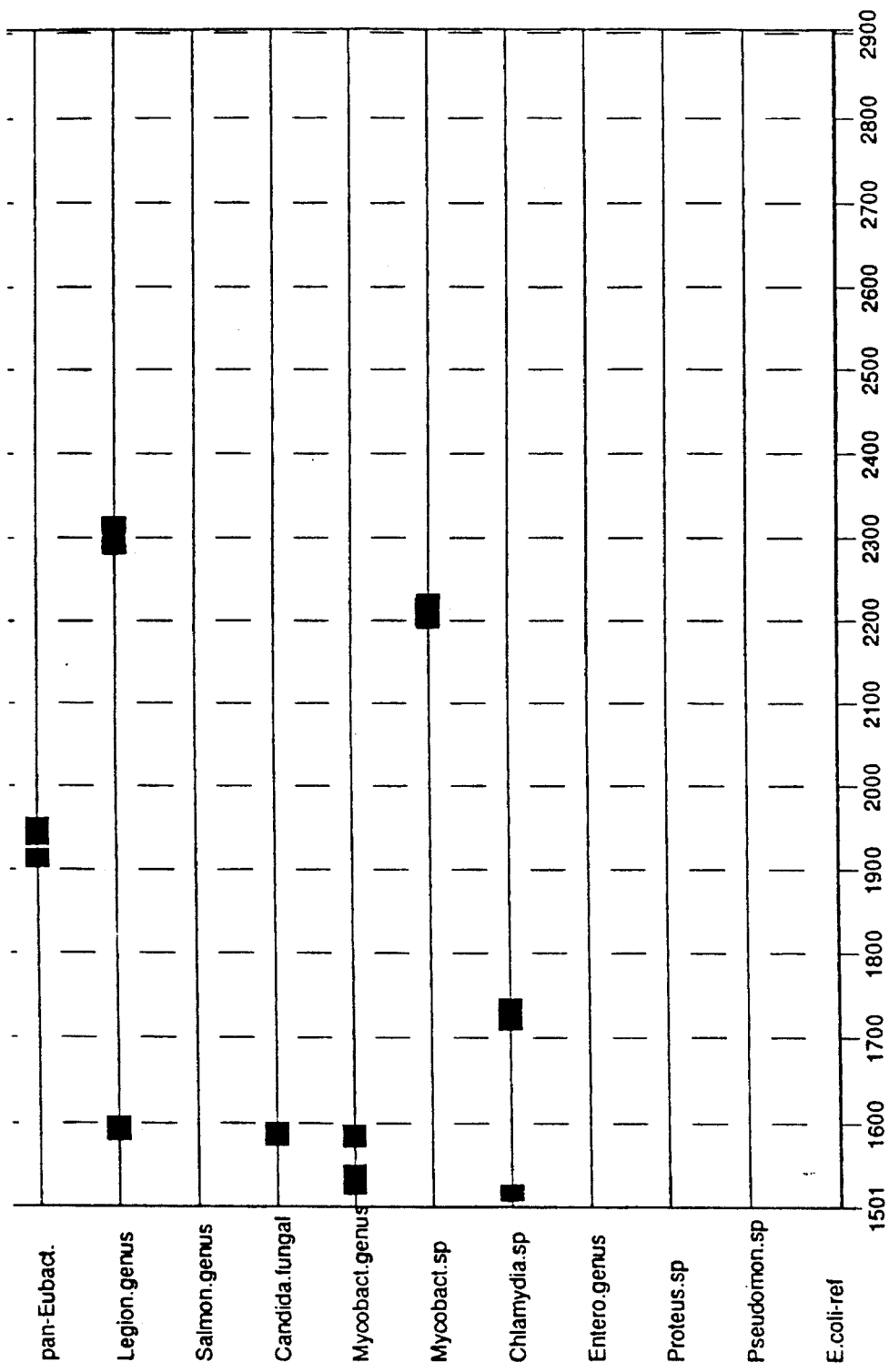

FIGS. 9, 10 and 11 are a schematic representation of the location of probes disclosed and claimed herein. Because 16S and 23S RNAs do not, as a rule, contain sequences of duplication longer than about six nucleotides in length, probes designed by these methods are specific to one or a few positions on the target nucleic acid.

The sequence evolution at each of the variable regions (for example, spanning a minimum of 10 nucleotides) is, for the most part divergent, not convergent. Thus, we can confidently design probes based on a few rRNA sequences which differ between the target organism and its phylogenetically closest relatives. Biological and structural constraints on the rRNA molecule which maintain homologous primary, secondary and tertiary structure throughout evolution, and the application of such constraints to probe diagnostics is the subject of ongoing study. The greater the evolutionary distance between organisms, the greater the number of variable regions which may be used to distinguish the organisms.

Once the variable regions are identified, the sequences are aligned to reveal areas of maximum homology or "match".

At this point, the sequences are examined to identify potential probe regions. Two important objectives in designing a probe are to maximize homology to the target sequence(s) (greater than 90% homology is recommended) and to minimize homology to non-target sequence(s) (less than 90% homology to nontargets is recommended). We have identified the following useful guidelines for designing probes with desired characteristics.

First, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible (for example, dG:rU base pairs are less destabalizing than some others).

Second, the stability of the probe: target nucleic acid hybrid should be maximized. This may be accomplished by avoiding long A and T rich sequences, by terminating the hybrids with G:C base pairs and by designing the probe with an appropriate Tm. The beginning and end points of the probe should be chosen so that the length and %G and %C result in a Tm about 2°–10° C. higher than the temperature at which the final assay will be performed. The importance and effect of various assay conditions will be explained further herein. Third, regions of the rRNA which are known to form strong structures inhibitory to hybridization are less preferred. Finally, probes with extensive self-complementarity should be avoided.

In some cases, there may be several sequences from a particular region which will yield probes with the desired hybridization characteristics. In other cases, one sequence may be significantly better than another which differs merely by a single base.

The following chart indicates how, for one embodiment of the invention useful in the detection of a nucleic acid in the presence of closely related nucleic acid sequences, unique sequences can be selected. In this example, rRNA sequences have been determined for organisms A–E and their sequences, represented numerically, are aligned as shown. It is seen that sequence 1 is common to all organisms A–E. Sequences 2–6 are found only in organisms A, B and C, while sequences 8, 9 and 10 are unique to organism A. Therefore, a probe complementary to sequences 8, 9 or 10 would specifically hybridize to organism A.

| | Illustrative Pattern of Sequence Relationships Among Related Bacteria | | | | | | | | |
|---|---|---|---|---|---|---|---|---|---|
| Organism | | | | rRNA Sequence | | | | | |
| A | 1 | 2 | 3 | 4 | 5 | 6 | 7 | 8 | 9 | 10 |
| B | 1 | 2 | 3 | 4 | 5 | 6 | 7 | 11 | 12 | 13 |
| C | 1 | 2 | 3 | 4 | 5 | 6 | 14 | 15 | 16 | 17 |
| D | 1 | 18 | 19 | 20 | 21 | 22 | 23 | 24 | 25 | 26 |
| E | 1 | 18 | 19 | 20 | 21 | 27 | 28 | 29 | 30 | 31 |

In cases where the patterns of variation of a macromolecule are known, for example, rRNA, one can focus on specific regions as likely candidates for probe design. However, it is not always necessary to determine the entire nucleic acid sequence in order to obtain a probe sequence. Extension from any single oligonucleotide primer can yield up to 300–400 bases of sequence. When a single primer is used to partially sequence the rRNA of the target organism and organisms closely related to the target, an alignment can be made as outlined above. Plainly, if a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

Thus, in Examples 1–3 below, two 16S-derived primers were used. The first primer did not yield probe sequences which met the criteria listed herein. The second primer yielded probe sequences which were determined to be useful following characterization and testing for specificity as described. In Example 4, six 23S primers were used prior to locating the probe sequence set forth.

Once a presumptive unique sequence has been identified, a complementary DNA oligonucleotide is synthesized. This single stranded oligonucleotide will serve as the probe in the DNA/rRNA assay hybridization reaction. Defined oligonucleotides may be synthesized by any of several well known methods, including automated solid-phase chemical synthesis using cyano-ethylphosphoramidite precursors. Barone, A. D. et al., *Nucleic Acids Research* 12, 4051–4060 (1984). In this method, deoxyoligonucleotides are synthesized on solid polymer supports. Release of the oligonucleotide from the support is accomplished by treatment with ammonium hydroxide at 60° C. for 16 hours. The solution is dried and the crude product is dissolved in water and separated on polyacrylamide gels which generally may vary from 10–20% depending upon the length of the fragment. The major band, which is visualized by ultraviolet back lighting, is cut from the gel with a razor blade and extracted with 0.1M ammonium acetate, pH 7.0, at room temperature for 8–12 hours. Following centrifugation, the supernatant is filtered through a 0.4 micron filter and desalted on a P-10 column (Pharmacia). Other well known methods for construction of synthetic oligonucleotide may, of course, be employed.

Current DNA synthesizers can produce large amounts of synthetic DNA. After synthesis, the size of the newly made DNA is examined by gel filtration and molecules of varying size are generally detected. Some of these molecules represent abortive synthesis events which occur during the synthesis process. As part of post-synthesis purification, the synthetic DNA is usually size fractionated and only those molecules which are the proper length are kept. Thus, it is possible to obtain a population of synthetic DNA molecules of uniform size.

It has been generally assumed, however, that synthetic DNA is inherently composed of a uniform population of molecules all of the same size and base sequence, and that the hybridization characteristics of every molecule in the preparation should be the same. In reality, preparations of synthetic DNA molecules are heterogeneous and are composed of significant numbers of molecules which, although the same size, are in some way different from each other and have different hybridization characteristics. Even different preparations of the same sequence can sometimes have different hybridization characteristics.

Accordingly, preparations of the same synthetic probe sequence can have different hybridization characteristics. Because of this the specificity of probe molecules from different preparations can be different. The hybridization characteristics of each preparation should be examined in order to determine the hybridization conditions which must be used in order to obtain the desired probe specificity. For example, the synthetic probe described in Example 4 below has the specificity profile described in Table 14. This data was obtained by using the hybridization and assay conditions described. A separate preparation of this probe which has different hybridization characteristics may not have precisely the same specificity profile when assayed under the conditions presented in Example 4. Such probe preparations have been made. To obtain the desired specificity, these probes can be hybridized and assayed under different conditions, including salt concentration and/or temperature. The actual conditions under which the probe is to be used must be determined, or matched to extant requirements, for each batch of probe since the art of DNA synthesis is somewhat imperfect.

Following synthesis and purification of a particular oligonucleotide sequence, several procedures may be utilized to determine the acceptability of the final product. The first is polyacrylamide gel electrophoresis, which is used to determine size. The oligonucleotide is labelled using, for example, $^{32}$P-ATP and $T_4$ polynucleotide kinase. The labelled probe is precipitated in ethanol, centrifuged and the dried pellet resuspended in loading buffer (80% formamide, 20 mM NaOH, 1 mM EDTA, 0.1% bromophenol blue and 0.1% xylene cyanol). The samples are heated for five minutes at 90° C. and loaded onto a denaturing polyacrylamide gel. Electrophoresis is carried out in TBE buffer (0.1 M Tris HCl pH 8.3, 0.08 M boric acid, 0.002 M EDTA) for 1–2 hours at 1,000 volts. Following electrophoresis of the oligonucleotide the gel is exposed to X-ray film. The size of the oligonucleotide is then computed from the migration of oligonucleotide standards run concurrently.

The sequence of the synthetic oligonucleotide may also be checked by labelling it at the 5' end with $^{32}$P-ATP and $T_4$ polynucleotide kinase, subjecting it to standard chemical degradation techniques, Maxam, A. M. and Gilbert, W., Proc. Nat'l. Acad. Sci. USA 74, 560–564 (1980), and analyzing the products on polyacrylamide gels. Preferably, the nucleotide sequence of the probe is perfectly complementary to the previously identified unique rRNA sequence, although it need not be.

The melting profile, including the melting temperature (Tm) of the oligonucleotide/ rRNA hybrids should also be determined. One way to determine Tm is to hybridize a $^{32}$P-labelled oligonucleotide to its complementary target nucleic acid at 50° C. in 0.1 M phosphate buffer, pH 6.8. The hybridization mixture is diluted and passed over a 2 cm hydroxyapatite column at 50° C. The column is washed with 0.1 M phosphate buffer, 0.02% SDS to elute all unhybridized, single-stranded probes. The column temperature is then dropped 15° C. and increased in 5° C. increments until all of the probe is single-stranded. At each temperature, unhybridized probe is eluted and the counts per minute (cpm) in each fraction determined. The number of cpm shown to be bound to the hydroxyapatite divided by the total cpm added to the column equals the percent hybridization of the probe to the target nucleic acid.

An alternate method for determining thermal stability of a hybrid is outlined below. An aliquot of hybrid nucleic acid is diluted into 1 ml of either 0.12 M phosphate buffer, 0.2% SDS, 1 mM EDTA, 1 mM EGTA or an appropriate hybridization buffer. Heat this 1 ml of solution to 45 degrees C for 5 minutes and place it into a room temperature water bath to cool for 5 minutes. Assay this 1 ml of hybrid containing solution over a hydroxyapatite column, capturing the hybrid and washing away unbound probe. If a hybridization solution other than the 0.12 M phosphate buffer is used, then a dilution of the hybridization solution into the 0.12 M phosphate buffer will be necessary for binding. Keep taking aliquots and diluting into 1 ml of hybridization solution or into the standard 0.12 M phosphate buffer solution described above while raising the heating temperature 5 degrees C at a time. Continue this until all of the hybrid is dissociated. The point where one half of the hybrid is converted to the dissociated form is considered the Tm. The Tm for a given hybrid will vary depending on the hybridization solution being used because the thermal stability depends upon the concentration of different salts, detergents, and other solutes which effect relative hybrid stability during thermal denaturation.

Because the extent and specificity of hybridization reactions such as those described herein are affected by a number of factors, manipulation of one or more of those factors will determine the exact sensitivity and specificity of a particular probe, whether perfectly complementary to its target or not. For example, the base composition of the probe may be significant because G-C base pairs exhibit greater thermal stability as compared to A-T base pairs due to additional hydrogen bonding. Thus, hybridization involving complementary nucleic acids of higher G-C content will be stable at higher temperatures.

We have discovered that the length of the target nucleic acid sequence and, accordingly, the length of the probe sequence can also be important. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 15 and about 50 bases in length and are at least about 75–100% homologous to the target nucleic acid. For most applications 95–100% homology to the target nucleic acid is preferred.

Ionic strength and incubation temperature should also be taken into account in constructing a probe. It is known that the rate of hybridization will increase as ionic strength of the reaction mixture increases and that the thermal stability of hybrids will increase with increasing ionic strength. In general, optimal hybridization for synthetic oligonucleotide probes of about 15–50 bases in length occurs approximately 5° C. below the melting temperature for a given duplex. Incubation at temperatures below the optimum may allow mismatched base sequences to hybridize and can therefore result in reduced specificity.

As to nucleic acid concentration, it is known that the rate of hybridization is proportional to the concentration of the two interacting nucleic acid species. Thus, the presence of compounds such as dextran and dextran sulphate are thought to increase the local concentration of nucleic acid species and thereby result in an increased rate of hybridization. Other agents which will result in increased rates of hybridization are specified in U.S. application Ser. No. 627,795, entitled "Accelerated Nucleic Acid Reassociation Method" filed Jul. 5, 1984, Continuation-in-Part thereof, Serial No. (net yet assigned), filed Jun. 4, 1987, and U.S. application Ser. No. 816,711, entitled "Accelerated Nucleic Acid Reassociation Method", filed Jan. 7, 1986, both of which are incorporated by reference. On the other hand, chemical reagents which disrupt hydrogen bonds such as formamide, urea, DMSO, and alcohols will increase the stringency of hybridization.

Selected oligonucleotide probes may be labelled by any of several well known methods. Useful labels include radioisotopes as well as non-radioactive reporting groups. Isotopic labels include $^3$H, $^{35}$S, $^{32}$P, $^{125}$I, Cobalt and $^{14}$C. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting. The detection method selected will depend upon the hybridization conditions and the particular radio-isotope used for labelling.

Non-isotopic materials can also be used for labelling, and may be introduced by the incorporation of modified nucleotides through the use of enzymes or by chemical modification of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

In one embodiment of the DNA/rRNA hybridization assay invention, a labelled probe and bacterial target nucleic acids are reacted in solution. rRNA may be released from bacterial cells by the sonic disruption method described in Murphy, K. A. et al., U.S. application Ser. No. 841,860, entitled "Method for Releasing RNA and DNA From Cells", filed Mar. 20, 1986, which is incorporated herein by reference. Other known methods for disrupting cells include the use of enzymes, osmotic shock, chemical treatment, and vortexing with glass beads. Following or concurrent with the release of rRNA, labelled probe may be added in the presence of accelerating agents and incubated at the optimal hybridization temperature for a period of time necessary to achieve significant reaction. Following this incubation period, hydroxyapatite may be added to the reaction mixture to separate the probe/rRNA hybrids from the non-hybridized probe molecules. The hydroxyapatite pellet is washed, recentrifuged and hybrids detected by means according to the label used.

Twenty-one embodiments illustrative of the claimed inventions are set forth below, in which a synthetic probe or probes complementary to a unique rRNA sequence from a target organism, or group of organisms is determined, constructed and used in a hybridization assay.

DESCRIPTION OF PARTICULAR EMBODIMENTS

Mycobacterium are acid-fast, alcohol fast, aerobic, non-mobile bacilli. Their lipid content is high and their growth slow. *Mycobacterium avium* and *Mycobacterium intracellulare* are together referred to as *M. avium-intracellulare* because they are so difficult to differentiate. Recently, the *M. avium* complex, which includes *M. intracellulare*, was shown to be the second most commonly isolated, clinically significant Mycobacterium. Good, R. C. et al., J. Infect. Dis. 146, 829–833 (1982). More recent evidence indicates that these organisms are a common cause of opportunistic infection in patients with AIDS (acquired immune deficiency syndrome). Gill, V. J. et al., *J. Clin. Microbio.* 22, 543–546 (1985). Treatment of such infections in AIDS patients is difficult because these organisms are resistant to most anti-tuberculosis drugs. Often a combination of five drugs are used in therapy. The severity of these infections also requires rapid diagnosis which, prior to the invention herein, was not available.

Members of the *Mycobacterium tuberculosis* complex (Mtb) include *Mycobacterium tuberculosis, Mycobacterium bovis, Mycobacterium africanum* and *Mycobacterium microti*. The first three are pathogenic for humans while the last is an animal pathogen. These organisms produce slowly developing granulomas on the skin or they may invade internal organs. Tuberculosis of the lungs can be disseminated to other parts of the body by the circulatory system, the lymph system, or the intestinal tract. Despite advances in public health and the advent of effective chemotherapy, Mycobacterial disease, tuberculosis in particular, continues to represent a major world-wide health problem.

The classical method for detecting bacteria in a test sample involves culturing of the sample in order to expand the number of bacterial cells present into observable colony growths which can be identified and enumerated. If desired, the cultures can also be subjected to additional testing in order to determine antimicrobial susceptibility. Currently, the most widely used procedures for the detection, isolation and identification of Mycobacterium species are the acid-fast bacilli (AFB) smear (using either the Ziehl-Neelsen or fluorochrome techniques), culture methods using Lowenstein-Jensen media and Middlebrook media, and biochemical tests. The AFB relies on the high lipid content of Mycobacterium to retain dye after exposure to acid-alcohol. While the AFB smear test is relatively rapid and simple to perform it does not always detect Mycobacteria and will not differentiate between *Mycobacterium avium* and non-tuberculosis species, between Mycobacterium intracellulare and non-tuberculosis species, or between Mycobacterium tuberculosis-complex bacilli and non-tuberculosis species. For accurate identification of the infecting Mycobacterial species the clinician must rely on culture results which can require anywhere from 3 to 8 weeks of growth followed by extensive biochemical testing. Other tests have been developed based on the detection of metabolic products from Mycobacterium using carbon-14 labelled substrates. In particular, the Bactec (TM) instrument can detect the presence of Mycobacterium within 6 to 10 days of the time of innoculation. Gill, V. J., supra. However, the test does not distinguish Mycobacterium species. It is often important to make this determination so that particular drugs to which the organism is susceptible may be prescribed. For traditional culture methods, this requires an additional 2 to 3 weeks and for the Bactec method, an additional 6 to 10 days.

In addition, specific embodiments for *Mycoplasma pneumoniae*, the Mycobacterium, Legionella, Salmonella, *Chlamydia trachomatis*, Campylobacter, *Proteus mirabilis*, Enterococcus, *Enterobacter cloacae, E. coli*, Pseudomonas Group I, bacteria, fungi and *Neisseria gonorrhoeae* are set forth in the following examples.

As indicated by the below examples, the present invention has significant advantages over each of these prior art methods not only in the enhanced accuracy, specificity and simplicity of the test, but also in greatly reducing the time to achieve a diagnosis. The invention makes possible a definitive diagnosis and initiation of effective treatment on the same day as testing.

EXAMPLE 1

Described below is the preparation of a single strand deoxyoligonucleotide of unique sequence and defined length which is labelled and used as a probe in a solution hybridization assay to detect the presence of rRNA from *Mycobacterium avium*. This unique sequence is specific for the rRNA of *Mycobacterium avium* and does not significantly cross-react under the hybridization conditions of this Example, with nucleic acids from any other bacterial species or respiratory infectious agent, including the closely-related *Mycobacterium intracellulare*. This probe is able to distinguish the two species, notwithstanding an approximate 98% rRNA homology between the two species. In this Example, as well as in Examples 2 and 3, sequences for *M. avium, M, tuberculosis* complex, *M. intracellulare* and related organisms were obtained by using a specific primer to a highly conserved region in the 16S rRNA. The sequence of this primer, derived from *E. coli* rRNA, was 5'-GGC CGT TAC CCC ACC TAC TAG CTA AT-3'. 5 nanograms of primer was mixed with 1 microgram of each rRNA to be sequenced in the presence of 0.1 M KCl and 20mM Tris-HCl pH 8.3 in a final volume of 10 microliters. The reactions were heated 10 min. at 45° C. and then placed on ice. 2.5 microliters of $^{35}S$ 35S dATP and 0.5 microliters of reverse transcriptase were added. The sample was aliquoted into 4 tubes, each tube containing either dideoxy A, G, T, or C. The concentrations of these nucleotides are set forth in Lane et al., supra. The samples were incubated at 40° C. for 30 minutes, and were then precipitated in ethanol, centrifuged and the pellets lyophilized dry. Pellets were resuspended in 10 microliters formamide dyes (100% formamide, 0.1% bromphenol blue and 0.1% xylene cyanol), and loaded onto 80 cm 8% polyacrylamide gels. The gels were run at 2000 volts for 2–4 hours.

Thus, nucleotide sequences for the 16S rRNA of *Mycobacterium avium* and what were considered to be its closest phylogenetic neighbors, *Mycobacterium intracellulare* and *Mycobacterium tuberculosis*, were determined by the method of Lane, D. J. et al., *Proc. Nat. Acad. Sci. USA* 82:6955 (1985). In addition to determining the rRNA sequences for the organisms noted above, a spectrum of clinically significant Mycobacterium were also sequenced. These included *M. fortuitum, M. scrofulaceum* and *M. chelonae*. Selected members of several genera closely related to Mycobacterium were also sequenced, including *Rhodococcus bronchialis, Corynebacterium xerosis* and *Nocardia asteroides*.

Partial rRNA sequences from the above organisms were aligned for maximum nucleotide homology, using commercially available software from Intelligenetics, Inc., 1975 El Camino Real West, Mountain View, Calif. 94040-2216 (IFIND Program). From this alignment, regions of sequence unique to *Mycobacterium avium* were determined. The probe was selected so that it was perfectly complementary to a target nucleic acid sequence and so that it had a 10% or greater mismatch with the aligned rRNA from its known closest phylogenetic neighbor. A sequence 38 bases in length was chosen. The number of mismatched bases relative to the *Mycobacterium avium* sequence were as follows: Mycobacterium tuberculosis (8); *Mycobacterium intracellulare* (5); *Mycobacterium scrofulaceum* (6); *Mycobacterium chelonae* (12); and *Mycobacterium fortuitum* (10).

The following cDNA sequence was characterized by the criteria of length, Tm, and sequence analysis as described at pages 7–8 above and was determined to be specific for the rRNA Mycobacterium avium:

ACCGCAAAAGCTTTCCACCAGAAGACAT-GCGTCTTGAG. This sequence is complementary to a unique segment found in the 16S rRNA of *Mycobacterium avium*. The size of the probe is 38 bases. The probe has a Tm of 74° C. and sequence analysis by the method of Maxam & Gilbert (1980), supra, confirmed that the probe was correctly synthesized. The probe is capable of hybridizing to rRNA of M- avium in the region corresponding to bases 185–225 of *E. coli* 16S rRNA.

To demonstrate the reactivity of this sequence for *Mycobacterium avium*, it was tested as a probe in hybridization reactions under the following conditions. $^{32}P$-end-labeled oligonucleotide probes were mixed with 1 microgram ($7\times10^{-13}$ moles) of purified rRNA from Mycobacterium avium and reacted in 0.12 M PB hybridization buffer (equimolar amounts of $Na_2HPO_4$ and $NaH_2PO_4$), 1 mM EDTA and 0.02% SDS (sodium dodecyl sulfate) at 65° C. for 60 minutes in a final volume of 50 microliters. In separate tubes the probe was mixed with the hybridization buffer both with and without target present. Following separation on hydroxyapatite as outlined in the patent applications identified at page 2, supra, the hybrids were quantitated by scintillation counting. These results are presented in Table 1, showing that the probe has a high extent of reaction to homologous target and very little non-specific binding to the hydroxyapatite.

TABLE 1

HYBRIDIZATION OF THE *M. AVIUM* PROBE TO HOMOLOGOUS TARGET rRNA*

|  | plus rRNA | minus rRNA |
|---|---|---|
| *M. avium* probe | 85–95% | 0.5% |

*% Hybridization = $\frac{\text{cpm bound to hydroxyapatite}}{\text{total cpm added to reaction}}$ Specificity of the probe for *M. avium* was tested by mixing the $^{32}P$ labeled probe with rRNA released from cells of 29 other species of mycobacteria by the sonic disruption techniques described in Murphy et al., U.S. application Ser. No. 841,860. $1\times10^8$ cells were suspended in 0.1 ml 5% SDS and sonicated for 10 minutes at 50°–60° C. 1.0 ml of hybridization buffer (45% sodium diisobutyl sulfosuccinate, 40 mM phosphate buffer pH 6.8 and 1 mM EDTA) was added and the mixture incubated for 60 minutes at 72° C. Following incubation, 4.0 ml of hydroxyapatite solution (0.14 M sodium phosphate buffer, pH 6.8, 0.02% SDS and 1.0 gram hydroxyapatite per 50 mls solution) was added and incubated for 5 minutes at 72° C. The sample was centrifuged and the supernatant removed. 4.0 ml wash solution (0.14 M sodium phosphate pH 6.8) was added and sample was vortexed, centrifuged and the supernatant removed. The radioactivity bound to the hydroxyapatite was determined by scintillation counting. The results are shown in Table 2 and indicate that the probe is specific for *Mycobacterium avium* and does not react with any other mycobacterial species, including *Mycobacterium intracellulare*.

TABLE 2

HYBRIDIZATION OF THE *M. AVIUM* PROBE TO MYCOBACTERIAL SPECIES

| Organism | ATCC# | % Probe Bound |
|---|---|---|
| *Mycobacterium africanum* | 25420 | 1.0 |
| *M. asiaticum* | 25276 | 1.2 |
| *M. avium* | 25291 | 87.6 |
| *M. bovis* | 19210 | 1.2 |
| *M. bovis* (BCG) | 19015 | 1.0 |
| *M. chelonae* | 14472 | 0.9 |
| *M. flavescens* | 14474 | 0.9 |
| *M. fortuitum* | 6841 | 1.0 |
| *M. gastri* | 15754 | 1.2 |
| *M. gordonae* | 14470 | 1.2 |
| *M. haemophilum* | 29548 | 1.3 |
| *M. intracallulare* | 13950 | 1.5 |
| *M. kansasii* | 12478 | 1.2 |
| *M. malmoense* | 29571 | 1.2 |
| *M. marinum* | 827 | 1.2 |
| *M. nonchromogenicum* | 1930 | 1.1 |
| *M. phlei* | 11758 | 1.3 |
| *M. scrofulaceum* | 19981 | 1.2 |
| *M. shimoidei* | 27962 | 2.3 |
| *M. simiae* | 25275 | 1.2 |
| *M. smegmatis* | e14468 | 1.0 |

TABLE 2-continued

HYBRIDIZATION OF THE *M. AVIUM* PROBE TO MYCOBACTERIAL SPECIES

| Organism | ATCC# | % Probe Bound |
|---|---|---|
| M. szulgai | 23069 | 1.0 |
| M. terrae | 15755 | 1.2 |
| M. thermoresistibile | 19527 | 1.3 |
| M. triviale | 23292 | 1.2 |
| M. tuberculosis (avirulent) | 25177 | 1.4 |
| M. tuberculosis (virulent) | 27294 | 1.1 |
| M. ulcerans | 19423 | 1.4 |
| M. vaccae | 15483 | 1.2 |
| M. xenopi | 19971 | 1.5 |

As shown in Table 3 the probe also did not react with the rRNA from any of the respiratory pathogens which were also tested by the method just described. Nor did the probe react with any other closely related or phylogenetically more diverse species of bacteria also tested by that method (Table 4).

TABLE 3

HYDRIDIZATION OF *M. AVIUM* PROBE TO RESPIRATORY PATHOGENS

| Organism | ATCC# | % Probe Bound |
|---|---|---|
| Corynebacterium xerosis | 373 | 0.7 |
| Fusobacterium nucleatum | 25586 | 1.3 |
| Haemophilum influenzae | 19418 | 1.3 |
| Klebsiella pneumoniae | 23357 | 1.8 |
| Legionella pneumophila | 33152 | 0.0 |
| Mycoplasma pneumoniae | 15531 | 3.0 |
| Neisseria meningitidis | 13090 | 0.0 |
| Pseudomonas aeruginosa | 25330 | 0.0 |
| Propionibacterium acnes | 6919 | 1.1 |
| Streptococcus pneumoniae | 6306 | 0.0 |
| Staphylococcus aureus | 25923 | 1.5 |

TABLE 4

HYDRIDIZATION OF THE *M. AVIUM* PROBE TO A PHYLOGENETIC CROSS SECTION OF BACTERIAL SPECIES

| Organism | ATCC# | % Probe Bound |
|---|---|---|
| Acinetobacter calcoaceticus | 33604 | 0.0 |
| Branhamella catarrahalis | 25238 | 0.6 |
| Bacillus subtilis | 6051 | 0.9 |
| Bacteroides fragilis | 23745 | 1.0 |
| Campylobacter jejuni | 33560 | 0.4 |
| Chromobacterium Violaceium | 29094 | 1.7 |
| Clostridium perfringens | 13124 | 2.1 |
| Deinococcus radiodurans | 35073 | 0.8 |
| Derxia gummosa | 15994 | 0.3 |
| Enterobacter aerogenes | 13048 | 0.6 |
| Escherichia coli | 11775 | 0.3 |
| Mycobacterium gordonae | 14470 | 1.9 |
| Mycoplasma hominis | 14027 | 3.3 |
| Proteus mirabilis | 29906 | 0.0 |
| Psudomonas cepacia | 11762 | 1.0 |
| Rahnella aquatilis | 33071 | 2.1 |
| Rhodospirillum rubrum | 11170 | 0.6 |
| Streptococcus mitis | 9811 | 0.9 |
| Vibrio parahaemolyticus | 17802 | 1.2 |
| Yershinia enterocolitica | 9610 | 0.4 |

EXAMPLE 2

After the alignment described in Example 1, the following sequence was characterized by the aforementioned criteria of length, Tm and sequence analysis and was determined to be specific for *Mycobacterium intracellulare:*

ACCGCAAAAGCTTTCCACCTAAAGACAT-GCGCCTAAAG

The sequence is complementary to a unique segment found in the 16S rRNA of *Mycobacterium intracellulare*. The size of the probe was 38 bases. The probe has a Tm of 75° C. and sequence analysis confirmed that the probe was correctly synthesized. The probe hybridizes to RNA of M- intracellulare in the region corresponding to bases 185–225 of *E. coli* 16S rRNA.

To demonstrate the reactivity of this sequence for the *Mycobacterium intracellulare*, the probe was tested in hybridization reactions under the following conditions. $^{32}$P-end-labelled oligonucleotide probe was mixed with 1 microgram ($7 \times 10^{-13}$ moles) of purified rRNA from *Mycobacterium intracellulare* and reacted in 0.12 M PB (equimolar amounts of $Na_2HPO_4$ and $NaH_2PO$), 1 mM EDTA and 0.2% SDS (sodium dodecyl sulfate) at 65° C. for 60 minutes in a final volume of 50 microliters. In separate tubes the probe was mixed with the hybridization buffer with and without target *Mycobacterium intracellulare* rRNA present. Following separation on hydroxyapatite as outlined previously the hybrids were quantitated by scintillation counting. These results are shown in Table 5.

TABLE 5

HYBRIDIZATION OF THE *M. INTRACELLULARE* PROBE TO HOMOLOGOUS TARGET rRNA*/

| | plus rRNA | minus rRNA |
|---|---|---|
| M. intracellulare probe | 85–95% | 0.5% |

*% Hybridization = $\frac{\text{cpm bound to hydroxyapatite}}{\text{total cpm added to reaction}}$ These data shows that the probe has a high extent of reaction to its homologous target and very little non-specific binding to the hydroxyapatite.

Specificity of the *Mycobacterium intracellulare* probe was tested by mixing the $^{32}$P labelled probe with rRNA released from cells from 29 other species of mycobacteria by sonic disruption techniques described in Murphy et. al. U.S. Pat. application Ser. No. 841,860. All hybridization assays were carried out as described in Example 1. Table 6 indicates that the probe is specific for *Mycobacterium intracellulare* and does not react with any other mycobacterial species, including *Mycobacterium avium*. These results are impressive in view of the 98% rRNA homology to *M. avium*; 98% homology to *M. kansasii*; 98% homology to *M. asiaticum*; and 97% homology to *M. tuberculosis*.

TABLE 6

HYBRIDIZATION OF THE *M. INTRACELLULARE* PROBE TO MYCOBACTERIAL SPECIES

| Organism | ATCC# | % Probe Bound |
|---|---|---|
| Mycobacterium africanum | 25420 | 0.9 |
| M. asiaticum | 25276 | 1.1 |
| M. avium | 25291 | 1.3 |
| M. bovis | 19210 | 1.1 |
| M. bovis (BCG) | 19015 | 1.2 |
| M. chelonae | 14472 | 1.0 |
| M. favescens | 14474 | 1.2 |
| M. fortuitum | 6841 | 1.3 |
| M. gastri | 15754 | 1.3 |
| M. gordonae | 14470 | 1.3 |

TABLE 6-continued

HYBRIDIZATION OF THE *M. INTRACELLULARE* PROBE TO MYCOBACTERIAL SPECIES

| Organism | ATCC# | % Probe Bound |
|---|---|---|
| M. haemophilum | 29548 | 0.9 |
| M. intracellulare | 13950 | 78.8 |
| M. kansasii | 12479 | 1.1 |
| M. Malmoense | 29571 | 1.0 |
| M. marinum | 827 | 0.9 |
| M. nonchromogenicum | 1930 | 1.0 |
| M. phlei | 11758 | 1.1 |
| M. scrofulaceum | 19981 | 1.0 |
| M. shimoidei | 27962 | 1.3 |
| M. simiae | 25275 | 1.1 |
| M. smegmatis | e14468 | 1.3 |
| M. szulgai | 23069 | 1.0 |
| M. terrae | 15755 | 1.4 |
| M. thermoresistibile | 19527 | 1.6 |
| M. triviale | 23292 | 1.3 |
| M. tuberculosis (avirulent) | 25177 | 1.2 |
| M. tuberculosis (virulent) | 27294 | 1.2 |
| M. ulcerans | 19423 | 1.1 |
| M. vaccae | 15483 | 1.0 |
| M. xenopi | 19971 | 1.2 |

As shown in Table 7 the probe did not react with the rRNA from any of the respiratory pathogens tested in the hybridization assay. Nor did the probe react with any other closely related or phylogenetically more diverse species of bacteria that were tested (Table 8).

TABLE 7

HYBRIDIZATION OF THE *M. INTRACELLULARE* PROBE TO RESPIRATORY PATHOGENS

| Organism | ATCC# | % Probe Bound |
|---|---|---|
| Corynebacterium xerosis | 373 | 2.2 |
| Fusobacterium nucleatum | 25586 | 1.5 |
| Haemophilum influenzae | 19418 | 1.3 |
| Klebsiella pneumoniae | 23357 | 1.2 |
| Legionella pneumophila | 33152 | 1.2 |
| Mycoplasma pneumoniae | 15531 | 3.2 |
| Neisseria meningitidis | 13090 | 1.1 |
| Pseudomonas aeruginosa | 25330 | 1.0 |
| Propionibacterium acnes | 6919 | 2.9 |
| Streptococcus pneumoniae | 6306 | 1.6 |
| Straphylococcus aureus | 25923 | 1.3 |

TABLE 8

HYBRIDIZATION OF THE *M. INTRACELLULARE* PROBE TO A PHYLOGENETIC CROSS SECTION OF BACTERIAL SPECIES

| Organism | ATTC# | % Probe |
|---|---|---|
| Acinetobacter calcoaceticus | 33604 | 1.5 |
| Branhamella catarrhalis | 25238 | 1.8 |
| Bacillus subtilis | 6051 | 1.7 |
| Bacteroides fragilis | 23745 | 1.9 |
| Campylobacter jejuni | 33560 | 1.9 |
| Chromobacterium Violaceum | 29094 | 1.4 |
| Clostridium perfringens | 13124 | 2.1 |
| Deinococcus radiodurans | 35073 | 2.1 |
| Derxia gummosa | 15994 | 1.6 |
| Enterobacter aerogenes | 13048 | 1.3 |
| Escherichia coli | 11775 | 1.2 |
| Mycobacterium gordonae | 14470 | 2.3 |
| Mycoplasma hominis | 14027 | 2.6 |
| Proteus mirabilis | 29906 | 1.2 |
| Pseudomonas cepacia | 11762 | 1.7 |
| Rahnella aquatilis | 33071 | 1.5 |

TABLE 8-continued

HYBRIDIZATION OF THE *M. INTRACELLULARE* PROBE TO A PHYLOGENETIC CROSS SECTION OF BACTERIAL SPECIES

| Organism | ATTC# | % Probe |
|---|---|---|
| Rhodospirillum rubrum | 11170 | 1.4 |
| Strptococcus mitis | 9811 | 1.4 |
| Vibrio parahaemolyticus | 17802 | 2.5 |
| Yersinia enterocolitica | 9610 | 1.1 |

After the alignment described in Example 1, the following sequence was characterized by the aforementioned three criteria of size, sequence and Tm, and was determined to be specific to the Mtb complex of organisms, *Mycobacterium tuberculosis, Mycobacterium, africanum, Mycobacterium bovis,* and *Mycobacterium microti:*

1. TAAAGCGCTTTCCACCACAAGACATG-CATCCCGTG.

The sequence is complementary to a unique segment found in the 16S rRNA of the Mtb-complex bacteria. The size of the probe is 35 bases. The probe has a Tm of 72° C. and sequence analysis confirmed that the probe was correctly synthesized. It is capable of hybridizing in the region corresponding to bases 185–225 of *E. coli* 16S rRNA.

To demonstrate the reactivity of this sequence for the Mtb complex the probe was tested in hybridization reactions under the following conditions. $^{32}$P-end-labelled oligonucleotide probe was mixed with 1 microgram ($7\times10^{-13}$ moles) of purified rRNA from *Mycobacterium tuberculosis* and reacted in 0.12 M PB hybridization buffer (equimolar amounts of $Na_2HPO_4$, and $NaH_2PO_4$), 1 mM EDTA and 0.2 SDS (sodium dodecyl sulfate) at 65° C. for 60 minutes in a final volume of 50 microliters. In separate tubes the probe was mixed with the hybridization buffer with and without target rRNA from *Mycobacterium tuberculosis* present. Following separation on hydroxyapatite as outlined previously the hybrids were quantitated by scintillation counting. The results are shown in Table 9.

TABLE 9

HYBRIDIZATION OF Mtb-COMPLEX 16S rRNA DNA PROBE TO HOMOLOGOUS TARGET rRNA*/

| | plus rRNA | minus rRNA |
|---|---|---|
| Mtb complex probe | 85–95% | 0.5% |

*% Hybridization = $\frac{\text{cpm bound to hydroxyapatite}}{\text{total cpm added to reaction}}$ This data shows that the probe has a high extent of reaction to homologous target and very little non-specific binding to the hydroxyapatite.

Specificity of the probe for the Mtb complex was tested by mixing the $^{32}$P labelled probe with rRNA released from cells of the 4 Mtb complex bacilli and of other mycobacterial species by sonic disruption techniques described in Murphy et. al., U.S. Pat. application Ser. No. 841,860. All hybridization assays were carried out as described in Example 1. Table 10 indicates that the probe is specific for organisms within the Mtb complex and does not react with any other mycobacterial species.

TABLE 10

HYBRIDIZATION OF Mtb-COMPLEX 16S rRNA DNA PROBE TO MYCOBACTERIAL SPECIES

| Organism | ATCC# | % Probe Bound |
|---|---|---|
| Mycobacterium africanum | 25420 | 68.1 |
| M. asiaticum | 25276 | 3.4 |
| M. avium | 25291 | 0.9 |
| M. bovis | 19210 | 63.1 |
| M. chelonae | 14472 | 1.1 |
| M. flavescens | 14474 | 0.9 |
| M. fortuitum | 6841 | 1.1 |
| M. gastri | 15754 | 0.8 |
| M. gordonae | 14470 | 1.1 |
| M. haemophilum | 29548 | 0.8 |
| M. intracallulare | 13950 | 1.1 |
| M. kansasii | 12479 | 1.3 |
| M. malmoense | 29571 | 0.9 |
| M. marinum | 827 | 1.1 |
| M. nonchromogenicum | 1930 | 1.1 |
| M. phlei | 11758 | 1.3 |
| M. scrofulaceum | 19981 | 1.1 |
| M. shimoidei | 27962 | 1.0 |
| M. simiae | 25275 | 1.2 |
| M. smegmatis | e14468 | 0.9 |
| M. szulgai | 23069 | 1.1 |
| M. terrae | 15755 | 1.0 |
| M. thermoresistibile | 19527 | 1.0 |
| M. triviale | 23292 | 1.2 |
| M. tuberculosis (avirulent) | 25177 | 66.2 |
| M. tuberculosis (virulent) | 27294 | 62.4 |
| M. ulcerans | 19423 | 0.9 |
| M. vaccae | 15483 | 0.8 |
| M. xenopi | 19971 | 2.6 |

As shown in Table 11 the probe did not react with the rRNA from any of the respiratory pathogens tested in the hybridization assay. Nor did the probe react with any other closely related or phylogenetically more diverse species of bacteria that were tested (Table 12).

TABLE 11

HYBRIDIZATION OF Mtb-COMPLEX 16S rRNA DNA PROBE TO RESPIRATORY PATHOGENS

| Organism | ATCC# | % Probe Bound |
|---|---|---|
| Corynebacterium xerosis | 373 | 1.3 |
| Fusobacterium nucleatum | 25586 | 1.0 |
| Haemophilum influenzae | 19418 | 1.6 |
| Klebsiella pneumoniae | 23357 | 1.2 |
| Legionella pneumophila | 33152 | 1.4 |
| Mycoplasma pneumoniae | 15531 | 1.1 |
| Neisseria meningitidis | 13090 | 1.0 |
| Pseudomonas aeruginosa | 25330 | 1.7 |
| Propionibacterium acnes | 6919 | 1.2 |
| Streptococcus pneumoniae | 25923 | 0.9 |

TABLE 12

HYBRIDIZATION OF THE Mtb-COMPLEX 16S rRNA DNA PROBE TO A PHYLOGENETIC CROSS SECTION OF BACTERIAL SPECIES

| Organism | ATCC# | % Probe |
|---|---|---|
| Acinetobacter calcoaceticus | 33604 | 1.3 |
| Branhamella catarrhalis | 25238 | 1.5 |
| Bacillus subtilis | 6051 | 1.3 |
| Bacteroides fragilis | 23745 | 1.3 |
| Campylobacter jejuni | 33560 | 1.1 |
| Chromobacterium violaceum | 29094 | 1.0 |
| Clostridium perfringens | 13124 | 1.2 |
| Deinococcus radiodurans | 35073 | 1.0 |
| Derxia gummosa | 15994 | 1.0 |
| Enterobacter aerogenes | 13048 | 1.0 |
| Escherichia coli | 11775 | 1.0 |
| Mycobacterium gordonae | 14470 | 1.3 |
| Mycoplasma hominis | 14027 | 0.5 |
| Proteus mirabilis | 29906 | 1.0 |
| Pseudomonas cepacia | 11762 | 2.6 |
| Rahnella aquatilis | 33071 | 1.9 |
| Rhodospirillum rubrum | 11170 | 1.0 |
| Streptococcus mitis | 9811 | 1.1 |
| Vibrio parahaemolyticus | 17802 | 0.9 |
| Yersinia enterocolitica | 9610 | 1.1 |

Two derivatives of the probe of Example (numbered 2–3 below) were made and tested:

2.       CCGCTAAAGCGCTTTCCACCACAAGA-CATGCATCCCG

3.       ACACCGCTAAAGCGCTTTCCACCACAA-GACATGCATC.

All three probes have similar Tms (72°; 73.5°; and 72.3°, respectively) and similar hybridization characteristics.

Hybridization to *Mycobacterium tuberculosis* complex organisms was 68–75% and non-specific hybridization to hydroxyapatite was less than 2%. Results of hybridization assay tests for these derivatives follow.

TABLE 13

HYBRIDIZATION OF PROBE OF EXAMPLES 3 AND 2 DERIVATIVES THEREOF TO MYCOBACTERIAL SPECIES

| | | Example | | |
|---|---|---|---|---|
| Organism | ATCC# | % Probe 1 Bound | % Probe 2 Bound | % Probe 3 Bound |
| Mycobacterium africanum | 25420 | 68.1 | 69.4 | 70.6 |
| M. asiaticum | 25274 | 3.4 | 5.3 | 1.8 |
| M. avium | 25291 | .9 | 1.6 | 1.4 |
| M. bovis | 19210 | 63.1 | 75.3 | 74 |
| M. chelonae | 14472 | 1.1 | 1.5 | 1.6 |
| M. flavescens | 14474 | 0.9 | 2.7 | 1.4 |
| M. fortuitum | 6841 | 1.1 | 3.6 | 1.5 |
| M. gastri | 15754 | 0.8 | 3.6 | 1.7 |
| M. gordonae | 14470 | 1.1 | 1.6 | 1.4 |
| M. haemophilum | 29548 | 0.8 | 3.2 | 1.7 |
| M. intracellulare | 13950 | 1.1 | 1.6 | 1.4 |
| M. kansasii | 12478 | 1.3 | 2.1 | 2.0 |
| M. malmoense | 29571 | 0.9 | 2.8 | 1.5 |
| M. marinum | 827 | 1.1 | 2.1 | 1.5 |
| M. nonchromogenicum | 1930 | 1.1 | 3.0 | 1.5 |
| M. phlei | 11758 | 1.3 | 1.3 | 1.1 |
| M. scrofulaceum | 19981 | 1.1 | 3.4 | 1.6 |
| M. shimoidei | 27962 | 1.0 | 2.7 | 1.6 |
| M. simiae | 25275 | 1.2 | 2.9 | 1.8 |
| M. smegmatis | e14468 | 0.9 | 1.5 | 1.2 |
| M. szulgai | 23069 | 1.1 | 3.6 | 1.1 |
| M. terrae | 15755 | 1.0 | 3.7 | 2.0 |
| M. thermo-resistibile | 19527 | 1.0 | 1.6 | 1.3 |
| M. triviale | 23292 | 1.2 | 1.6 | 2.0 |
| M. tuberculosis (avirulent) | 25177 | 66.2 | 75 | 68 |
| M. tuberculosis (virulent) | 27294 | 62.4 | 74 | 75 |
| M. ulcerans | 19423 | 0.9 | 1.7 | 3.0 |

TABLE 13-continued

HYBRIDIZATION OF PROBE OF EXAMPLES 3 AND 2
DERIVATIVES THEREOF
TO MYCOBACTERIAL SPECIES

| | | Example | | |
|---|---|---|---|---|
| Organism | ATCC# | % Probe 1 Bound | % Probe 2 Bound | % Probe 3 Bound |
| M. vaccae | 15483 | 0.8 | 1.4 | 1.2 |
| M. xenopi | 19971 | 2.6 | 1.4 | 1.2 |

EXAMPLE 4

The probe specific for the 23S rRNA of the *M. tuberculosis* complex was obtained by using a primer which was complementary to a highly conserved region of 23S rRNA. The sequence of this primer, derived from *E. coli* rRNA, was 5'-AGG AAC CCT TGG GCT TTC GG-3'. Five nanograms of this primer was mixed with 1 microgram of rRNA from *M. tuberculosis* and other closely related Mycobacterium and the procedure as described for Examples 1, 2 and 3 was followed. After alignment as described in Example 1, the following sequence was determined to be specific to the Mtb complex of organisms, *Mycobacterium tuberculosis, Mycobacterium africanum, Mycobacterium bovis,* and *Mycobacterium microti:*

TGCCCTACCCACACCCACCACAAGGTGATGT.

The sequence is complementary to a unique segment found in the 23S rRNA of the Mtb-complex bacteria. The oligonucleotide probe was characterized as previously described by the criteria of length, Tm and sequence analysis. The size of the probe is 31 bases. The probe has a Tm of 72.5° C. and sequence analysis confirmed that the probe was correctly synthesized. It is capable of hybridizing in the region corresponding to bases 1155–1190 of *E. coli* 23S rRNA.

To demonstrate the reactivity of this sequence for the Mtb complex the probe was tested in hybridization reactions under the following conditions. $^{32}$P-end-labelled oligonucleotide probes were mixed with 1 microgram ($7\times10^{-13}$ moles) of purified rRNA from *Mycobacterium tuberculosis* and reacted in 0.12 M PB hybridization buffer (equimolar amounts of Na$_2$HPO$_4$, and NaH$_2$PO$_4$), 1 mM EDTA and 0.2 SDS (sodium dodecyl sulfate) at 65° C. for 60 minutes in a final volume of 50 microliters. In separate tubes the probe was mixed with the hybridization buffer with and without target rRNA from Mycobacterium tuberculosis present. Following separation on hydroxyapatite as outlined previously the hybrids were quantitated by scintillation counting. The results are shown in Table 14.

TABLE 14

HYBRIDIZATION OF THE Mtb-COMPLEX
23S rRNA DNA PROBE TO
HOMOLOGOUS TARGET rRNA

| | plus rRNA | minus rRNA |
|---|---|---|
| Mtb complex 23S probe | 94% | 1.2% |

These data show that the probe has a high extent of reaction to homologous target and very little non-specific binding to the hydroxyapatite.

Specificity of the probe for the Mtb complex was tested by mixing the $^{32}$P labelled probe with rRNA released from cells of the four Mtb complex bacilli and of 25 other mycobacterial species by sonic disruption techniques described in Murphy et al., U.S. patent application Ser. No. 841,860. All hybridization assays were carried out as described in Example 1. Table 14 indicates that the probe is specific for organisms within the Mtb complex and does not react with any other mycobacterial species.

TABLE 15

HYBRIDIZATION OF Mtb-COMPLEX 23S rRNA DNA
PROBE TO MYCOBACTERIAL SPECIES

| Organism | ATCC# | % Probe Bound |
|---|---|---|
| Mycobacterium africanum | 25420 | 33.6 |
| M. asiaticum | 25276 | 1.2 |
| M. avium | 25291 | 1.0 |
| M. bovis | 19210 | 32.0 |
| M. chelonae | 14472 | 1.2 |
| M. flavescens | 14474 | 1.2 |
| M. fortuitum | 6841 | 1.3 |
| M. gastri | 15754 | 1.1 |
| M. gordonae | 14470 | 1.2 |
| M. haemophilum | 29548 | 1.2 |
| M. intracellulare | 13950 | 1.1 |
| M. kansasii | 12479 | 1.3 |
| M. malmoense | 29571 | 1.3 |
| M. marinum | 827 | 1.2 |
| M. nonchromogenicum | 1930 | 1.0 |
| M. phlei | 11758 | 1.0 |
| M. scrofulaceum | 19981 | 1.1 |
| M. shimoidei | 27962 | 1.2 |
| M. simiae | 25275 | 1.3 |
| M. smegmatis | e14468 | 1.1 |
| M. szulgai | 23069 | 1.1 |
| M. terrae | 15755 | 1.0 |
| M. thermoresistibile | 19527 | 1.2 |
| M. triviale | 23292 | 1.0 |
| M. tuberculosis (avirulent) | 25177 | 33.7 |
| M. tuberculosis (virulent) | 27294 | 38.1 |
| M. ulcerans | 19423 | 1.3 |
| M. vaccae | 15483 | 1.0 |
| M. xenopi | 19971 | 1.3 |

EXAMPLE 5

Three additional *Mycobacterium tuberculosis* complex probes, Examples 5–7 herein, were identified using two unique primers complementary to 23S rRNA. The first sequence is:

CCATCACCACCCTCCTCCGGAGAGGAAAAGG.

The sequence of this Example 5 was obtained using a 23S primer with the sequence 5'-GGC CAT TAG ATC ACT CC-3'. It was characterized and shown to be specific for the Mycobacterium tuberculosis complex of organisms including *Mycobacterium tuberculosis, Mycobacterium africanum* and *Mycobacterium bovis*. This sequence, from 23S rRNA, is 31 bases in length and has a Tm of 72° C. This probe is capable of hybridizing to RNA of the aforementioned organisms in the region corresponding to bases 540–575 of *E. coli* 23S rRNA.

To demonstrate the reactivity and specificity of this probe for Mycobacterium tuberculosis complex, it was tested as a probe in hybridization reactions under the following conditions. $^{32}$P-end-labeled oligonucleotide probe was mixed with rRNA released from cells of 30 species of mycobacteria by the sonic disruption techniques described in Murphy et al., U.S. patent application Ser. No. 841,860. $3\times10^7$ cells were suspended in 0.1 ml 5% SDS and sonicated for 15 minutes at 50°–60° C. One ml of hybridization buffer (45% diisobutyl sulfosuccinate, 40 mM phosphate buffer pH 6.8, 1 mM EDTA, 1 mM EGTA) was added and the mixture incubated at 72° C. for 2 hours. Following incubation, 4 ml of 2% (w/v) hydroxyapatite, 0.12 M sodium phosphate buffer pH6.8, 0.02% SDS, 0.02% sodium azide was added and incubated at 72° C. for 5 minutes. The sample was centrifuged and the supernatant removed. Four ml wash solution (0.12 M sodium phosphate buffer pH6.8, 0.02% SDS, 0.02% sodium azide) was added and the sample was vortexed, centrifuged and the supernatant removed. The radioactivity bound to the hydroxyapatite was determined by scintillation counting. The results are shown in Table 16 and indicate that the probe is specific for the *Mycobacterium tuberculosis* complex of organisms.

TABLE 16

HYBRIDIZATION OF THE *M. TUBERCULOSIS* COMPLEX PROBE OF EXAMPLE 5 TO MYCOBACTERIAL SPECIES

| Organism | ATCC # | % Probe Bound |
| --- | --- | --- |
| *Mycobacterium africanum* | 25420 | 18.0 |
| *M. asiaticum* | 25274 | 2.6 |
| *M. avium* | 25291 | 3.4 |
| *M. bovis* | 19210 | 21.7 |
| *M. bovis* (BCG) | 35734 | 35.3 |
| *M. chelonae* | 14472 | 3.8 |
| *M. flavescens* | 14474 | 2.3 |
| *M. fortuitum* | 6841 | 1.8 |
| *M. gastri* | 15754 | 2.2 |
| *M. gordonae* | 14470 | 2.8 |
| *M. haemophilum* | 29548 | 2.8 |
| *M. intracellulare* | 13950 | 2.1 |
| *M. kansasii* | 12478 | 1.6 |
| *M. malmoense* | 29571 | 2.3 |
| *M. marinum* | 827 | 2.1 |
| *M. nonchromogenicum* | 1930 | 2.3 |
| *M. phlei* | 11758 | 2.1 |
| *M. scrofulaceum* | 19981 | 2.2 |
| *M. shimoidei* | 27962 | 1.9 |
| *M. simiae* | 25275 | 2.2 |
| *M. smegmatis* | e14468 | 2.0 |
| *M. szulgai* | 23069 | 2.2 |
| *M. terrae* | 15755 | 2.2 |
| *M. thermoresistible* | 19527 | 2.2 |
| *M. triviale* | 23292 | 2.0 |
| *M. tuberculosis* (avirulent) | 25177 | 26.4 |
| *M. tuberculosis* (virulent) | 27294 | 36.6 |
| *M. ulcerans* | 19423 | 2.5 |
| *M. vaccae* | 15483 | 2.4 |
| *M. xenopi* | 19971 | 2.8 |

Table 16 shows that the probe also did not cross react with RNA from any of the closely related organisms tested by the method just described.

TABLE 17

HYBRIDIZATION OF THE *M. TUBERCULOSIS* COMPLEX PROBE OF EXAMPLE 5 TO PHYLOGENETICALLY CLOSELY RELATED ORGANISMS

| Organism | ATCC# | % Probe Bound |
| --- | --- | --- |
| *Actinomadura madurae* | 19425 | 2.1 |
| *Actinoplanes italicus* | 10049 | 3.1 |
| *Arthrobacter oxidans* | 14358 | 2.1 |
| *Brevibacterium linens* | e9172 | 1.9 |
| *Corynebacterium xerosis* | 373 | 2.2 |
| *Dermatophilus congolensis* | 14367 | 2.2 |
| *Microbacterium lacticum* | 8180 | 2.1 |
| *Nocardia asteroides* | 19247 | 2.0 |
| *Nocardia brasiliensis* | 19296 | 2.2 |
| *Nocardia otitidis-caviarum* | 14629 | 2.0 |
| *Nocardiopsis dassonvillei* | 23218 | 4.0 |
| *Oerskovia turbata* | 33225 | 2.2 |
| *Oerskovia xanthineolytica* | 27402 | 2.0 |
| *Rhodococcus aichiensis* | 33611 | 1.9 |
| *Rhodococcus aurantiacus* | 25938 | 2.0 |

TABLE 17-continued

HYBRIDIZATION OF THE *M. TUBERCULOSIS* COMPLEX PROBE OF EXAMPLE 5 TO PHYLOGENETICALLY CLOSELY RELATED ORGANISMS

| Organism | ATCC# | % Probe Bound |
| --- | --- | --- |
| *Rhodococcus bronchialis* | 25592 | 2.1 |
| *Rhodococcus chubuensis* | 33609 | 2.3 |
| *Rhodococcus equi* | 6939 | 2.4 |
| *Rhodococcus obuensis* | 33610 | 2.2 |
| *Rhodococcus sputi* | 29627 | 2.3 |

EXAMPLE 6

The second *Mycobacterium tuberculosis* complex probe was obtained using a 23S primer with the sequence 5' CCT GAT TGC CGT CCA GGT TGA GGG AAC CTT TGG G-3'. Its sequence is:

CTGTCCCTAAACCCGATTCAGGGTTC-GAGGTTAGATGC

This sequence, from 23S rRNA, is 38 bases in length and has a Tm of 75° C. It hybridizes in the region corresponding to bases 2195–2235 of *E. coli* 23s rRNA.

Like the complex probe in Example 5, this sequence was characterized and shown to be specific for the *Mycobacterium tuberculosis* complex of organisms including *Mycobacterium tuberculosis*, *Mycobacterium africanum* and *Mycobacterium bovis*.

To demonstrate the reactivity and specificity of the probe of this Example 6 to *Mycobacterium tuberculosis* complex, it was tested as a probe in hybridization reactions under the following conditions described for the probe in Example 5. The results are shown in Table 18 and indicate that the probe is specific for the *Mycobacterium tuberculosis* complex of organisms with the exception of *Mycobacterium thermoresistibile*, a rare isolate which is not a human pathogen.

TABLE 18

HYBRIDIZATION OF THE *M. TUBERCULOSIS* COMPLEX PROBE OF EXAMPLE 6 TO MYCOBACTERIAL SPECIES

| Organism | ATCC # | % Probe Bound |
| --- | --- | --- |
| *Mycobacterium africanum* | 25420 | 56.0 |
| *M. asiaticum* | 25274 | 3.1 |
| *M. avium* | 25291 | 2.6 |
| *M. bovis* | 19210 | 48.0 |
| *M. bovis* (BCG) | 35734 | 63.0 |
| *M. chelonae* | 14472 | 2.8 |
| *M. flavescens* | 14474 | 2.8 |
| *M. fortuitum* | 6841 | 3.0 |
| *M. gastri* | 15754 | 3.2 |
| *M. gordonae* | 14470 | 3.0 |
| *M. haemophilum* | 29548 | 3.0 |
| *M. intracellulare* | 13950 | 3.6 |
| *M. kansasii* | 12478 | 3.9 |
| *M. malmoense* | 29571 | 2.9 |
| *M. marinum* | 827 | 2.9 |
| *M. nonchromogenicum* | 1930 | 4.8 |
| *M. phlei* | 11758 | 2.9 |
| *M. scrofulaceum* | 19981 | 2.6 |
| *M. shimoidei* | 27962 | 3.6 |
| *M. simiae* | 25275 | 3.3 |
| *M. smegmatis* | e14468 | 3.0 |
| *M. szulgai* | 23069 | 2.8 |
| *M. terrae* | 15755 | 2.8 |
| *M. thermoresistibile* | 19527 | 11.7 |
| *M. triviale* | 23292 | 3.2 |
| *M. tuberculosis* (avirulent) | 25177 | 65.0 |
| *M. tuberculosis* (virulent) | 27294 | 53.0 |

TABLE 18-continued

HYBRIDIZATION OF THE *M. TUBERCULOSIS* COMPLEX
PROBE OF EXAMPLE 6 TO MYCOBACTERIAL SPECIES

| Organism | ATCC # | % Probe Bound |
|---|---|---|
| M. ulcerans | 19423 | 2.5 |
| M. vaccae | 15483 | 2.8 |
| M. xenopi | 19971 | 3.3 |

Table 19 shows that the probe also did not cross react with RNA from any of the phylogenetically closely related organisms tested by the method just described.

TABLE 19

HYBRIDIZATION OF THE *M. TUBERCULOSIS* COMPLEX
PROBE OF EXAMPLE 6 TO PHYLOGENETICALLY
CLOSELY RELATED ORGANISMS

| Organism | ATCC # | % Probe Bound |
|---|---|---|
| Actinomadura madurae | 19425 | 1.3 |
| Actinoplanes italicus | 10049 | 0.6 |
| Arthrobacter oxidans | 14358 | 1.1 |
| Brevibacterium linens | e9172 | 0.8 |
| Corynebacterium xerosis | 373 | 1.0 |
| Dermatophilus congolensis | 14367 | 0.6 |
| Microbacterium lacticum | 8180 | 1.9 |
| Nocardia asteroides | 19247 | 0.9 |
| Nocardia brasiliensis | 19296 | 0.8 |
| Nocardia otitidis-caviarum | 14629 | 1.5 |
| Nocardiopsis dassonvillei | 23218 | 0.5 |
| Oerskovia turbata | 33225 | 0.3 |
| Oerskovia xanthineolytica | 27402 | 0.8 |
| Rhodococcus aichiensis | 33611 | 1.6 |
| Rhodococcus aurantiacus | 25938 | 0.7 |
| Rhodococcus bronchialis | 25592 | 1.5 |
| Rhodococcus chubuensis | 33609 | 0.8 |
| Rhodococcus equi | 6939 | 0.3 |
| Rhodococcus obuensis | 33610 | 0.8 |
| Rhodococcus sputi | 29627 | 1.4 |

EXAMPLE 7

The following additional *Mycobacterium tuberculosis* complex probe also has been identified using a 23S primer with the same sequence as that of Example 6, namely, 5'-CCT GAT TGC CGT CCA GGT TGA GGG AAC CTT TGG G-3':

AGGCACTGTCCCTAAACCCGATTCAGGGTTC.
This sequence, from 23S rRNA is 31 bases in length and has a Tm of 71° C. It hybridizes in the region corresponding to bases 2195–2235 of *E. coli* 23S rRNA. As is the case with the *Mycobacterium tuberculosis* complex probes of Examples 5 and 6 herein, this sequence also was characterized and shown to be specific for the Mycobacterium tuberculosis complex of organisms, including *Mycobacterium tuberculosis*, *Mycobacterium africanum* and *Mycobacterium bovis*.

To demonstrate the reactivity and specificity of this probe for *Mycobacterium tuberculosis* complex, it was tested as a probe in hybridization reactions under the conditions described for the probe of Example 5. Table 20 shows that the probe is specific for the *Mycobacterium tuberculosis* complex of organisms.

TABLE 20

HYBRIDIZATION OF THE *MYCOBACTERIUM
TUBERCULOSIS* COMPLEX PROBE OF EXAMPLE 7
TO MYCOBACTERIAL SPECIES

| Organism | ATCC # | % Probe Bound |
|---|---|---|
| Mycobacterium africanum | 25420 | 43.0 |
| M. asiaticum | 25274 | 0.6 |
| M. avium | 25291 | 0.7 |
| M. bovis | 19210 | 43.0 |
| M. bovis (BCG) | 35734 | 46.0 |
| M. chelonae | 14472 | 0.6 |
| M. flavescens | 14474 | 0.6 |
| M. fortuitum | 6841 | 0.5 |
| M. gastri | 15754 | 0.9 |
| M. gordonae | 14470 | 0.7 |
| M. haemophilum | 29548 | 0.6 |
| M. intracellulare | 13950 | 0.6 |
| M. kansasii | 12478 | 0.9 |
| M. malmoense | 29571 | 0.8 |
| M. marinum | 827 | 0.7 |
| M. nonchromogenicum | 1930 | 0.8 |
| M. phlei | 11758 | 0.6 |
| M. scrofulaceum | 19981 | 0.7 |
| M. shimoidei | 27962 | 0.8 |
| M. simiae | 25275 | 0.7 |
| M. smegmatis | e14468 | 0.6 |
| M. szulgai | 23069 | 0.6 |
| M. terrae | 15755 | 0.7 |
| M. thermoresistibile | 19527 | 0.9 |
| M. triviale | 23292 | 0.7 |
| M. tuberculosis (avirulent) | 25177 | 40.0 |
| M. tuberculosis (virulent) | 27294 | 50.0 |
| M. ulcerans | 19423 | 0.7 |
| M. vaccae | 15483 | 0.4 |
| M. xenopi | 19971 | 0.6 |

Table 21 shows that the probe also did not cross react with RNA from any of the closely related organisms tested by the method just described.

TABLE 21

HYBRIDIZATION OF THE *M. TUBERCULOSIS* COMPLEX
PROBE OF EXAMPLE 7 TO PHYLOGENETICALLY
CLOSELY REALTED ORGANISMS

| Organism | ATCC # | % Probe Bound |
|---|---|---|
| Actinomadura madurae | 19425 | 1.0 |
| Actinoplanes italicus | 10049 | 0.6 |
| Arthrobacter oxidans | 14358 | 0.4 |
| Brevibacterium linens | e9172 | 0.8 |
| Corynebacterium xerosis | 373 | 0.6 |
| Dermatophilus congolensis | 14367 | 0.8 |
| Microbacterium lacticum | 8180 | 0.5 |
| Nocardia asteroides | 19247 | 0.7 |
| Nocardia brasiliensis | 19296 | 0.5 |
| Nocardia otitidis-caviarum | 14629 | 0.6 |
| Nocardiopsis dassonvillei | 23218 | 0.6 |
| Oerskovia turbata | 33225 | 0.8 |
| Oerskovia xanthineolytica | 27402 | 0.6 |
| Rhodococcus aichiensis | 33611 | 0.7 |
| Rhodococcus aurantiacus | 25938 | 0.7 |
| Rhocococcus bronchialis | 25592 | 0.6 |
| Rhodococcus chubuensis | 33609 | 0.6 |
| Rhodococcus equi | 6939 | 0.6 |
| Rhodococus obuensis | 33610 | 0.6 |
| Rhodococcus sputi | 29627 | 0.9 |

Notably, overlapping probes may have identical specificity. Compare, for example, the probes of Examples 6 and 7:
Ex. 6    CTGTCCCTAAACCCGATTCAGGGTTC-GAGGTTAGATGC
Ex. 7    AGGCACTGTCCCTAAACCCGATTCAGGGTTC There may be several sequences from a particular region which will yield probes with the desired hybridization characteristics. In other cases, one probe sequence may be significantly better than another probe differing by a single base. In general, the greater the sequence difference (% mismatch) between a target and nontarget organism, the more likely one will be able to alter the probe without affecting its usefulness for a specific application. This phenomenon also was demonstrated by the derivative probes in Example 3.

In Example 7, five bases were added to the 5' end of the probe in Example 6, and 12 bases were removed from the 3' end. The two probes have essentially identical hybridization characteristics.

EXAMPLE 8

The Mycobacterium genus is particularly difficult to distinguish from Nocardia, Corynebacterium and Rhodococcus. These genera have common antigens, precipitins and G & C counts. Despite the fact that these organisms also exhibit 92–94% rRNA homology to the above listed Mycobacterium organisms, we have designed probes which detect all members of the genus Mycobacterium without cross reacting to the related genera.

Figures 2, 2A, 2C:
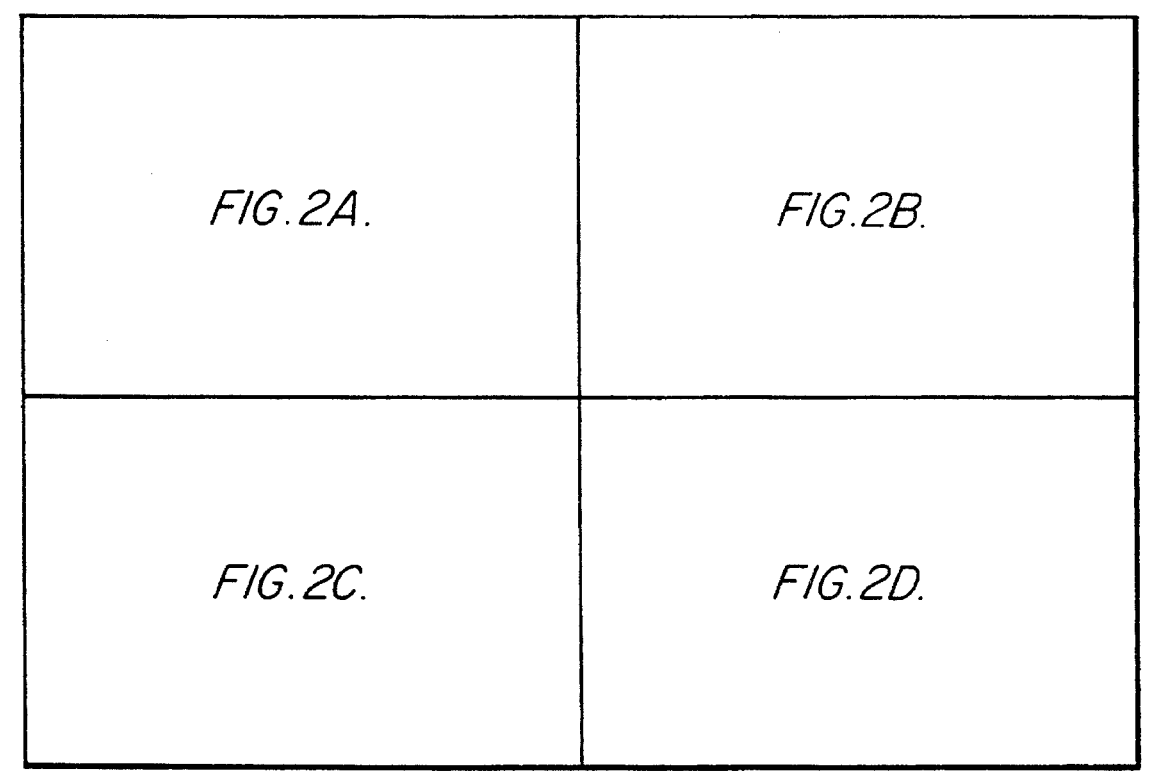

In addition to the Mycobacterium species probes already disclosed, four probes specific for members of the Mycobacterium genus were identified using one primer complementary to 16S rRNA and one primer complementary to 23S rRNA. Sequence 1 was obtained using a 16S primer with the sequence 5'-TTA CTA GCG ATT CCG ACT TCA-3'. Sequences 2, 3 and 4 were obtained using a 23S primer with the sequence 5'-GTG TCG GTT TTG GGT ACG-3'. Sequence 1 is capable of hybridizing to RNA of the genus Mycobacterium in the region corresponding to bases 1025–1060 of E. coli 16S rRNA. Sequences 2–4 hybridize in regions corresponding to the following bases of E. coli 23S rRNA in our numbering system (See FIG. 2); 1440–1475; 1515–1555; 1570–1610 in our numbering system.

The following sequences were characterized and shown to be specific for the genus Mycobacterium:

1. CCA TGC ACC ACC TGC ACA CAG GCC ACA AGG

2. GGC TTG CCC CAG TAT TAC CAC TGA CTG GTA CGG

3. CAC CGA ATT CGC CTC AAC CGG CTA TGC GTC ACC TC

4. GGG GTA CGG CCC GTG TGT GTG CTC GCT AGA GGC

Sequence 1, from 16S rRNA, is 30 bases in length and has a Tm of 73° . Sequence 2, from 23S rRNA, is 33 bases in length and has a Tm of 75° C. Sequence 3, from 23S rRNA, is 35 bases in length and has a Tm of 76° C. Sequence 4, from 23S rRNA, is 33 bases in length and has a Tm of 73° C.

To demonstrate the reactivity and specificity of probe 1 for members of the genus Mycobacterium, it was tested as a probe in hybridization reactions under the following conditions. $^{125}$I-labeled oligonucleotide probe was mixed with rRNA released from cells of 30 species of mycobacteria by the sonic disruption techniques described in Murphy et al., U.S. patent application Ser. No. 841,860. 3×10$^7$ cells were suspended in 0.1 ml 5% SDS and sonicated for 15 minutes at 50°–60° C. One ml of hybridization buffer (45% diisobutyl sulfosuccinate, 40 mM sodium phosphate pH6.8, 1 mM EDTA, 1 mM EGTA) was added and the mixture incubated at 72° C. for 2 hours. Following incubation, 2 ml of separation solution (containing 2.5 g/l cationic magnetic microspheres, 0.17 M sodium phosphate buffer pH6.8, 7.5% Triton X-100 (TM), 0.02% sodium azide) was added and incubated at 72° C. for 5 minutes. The RNA:probe hybrids, bound to the magnetic particles, were collected and the supernatant removed. One ml wash solution (0.12 M sodium phosphate buffer pH6.8, 14% diisobutyl sulfosuccinate, 5% Triton X-100, 0.02% sodium azide) was added, the particles collected and the supernatant removed. This step was repeated two times. The radioactivity bound to the magnetic particles was determined in a gamma counter. The results are shown in Table 22 and indicate that the probes hybridize to organisms in the genus Mycobacterium and that a combination of probes will detect all members of the genus. Table 23 shows that the probes do not react with other closely related bacteria.

TABLE 22

HYBRIDIZATION OF THE MYCOBACTERIUM PROBES 1–4 TO MYCOBACTERIAL SPECIES

| Organism | ATCC # | % Probe 1 Bound | % Probe 2 Bound | % Probe 3 Bound | % Probe 4 Bound |
|---|---|---|---|---|---|
| Mycobacterium africanum | 25420 | 41.5 | 14.7 | 17.9 | 26.7 |
| M. asiaticum | 25274 | 31.8 | 20.2 | 7.9 | 0.1 |
| M. avium | 25291 | 11.7 | 34.7 | 10.1 | 1.6 |
| M. bovis | 19210 | 19.4 | 28.4 | 44.6 | 20.9 |
| M. bovis (BCG) | 35734 | 30.0 | 35.5 | 17.8 | 5.6 |
| M. chelonae | 14472 | 8.6 | 0.7 | 6.3 | 0.2 |
| M. flavescens | 14474 | 29.8 | 17.7 | 2.3 | 0.9 |
| M. fortuitum | 6841 | 34.7 | 2.2 | 4.8 | 0.2 |
| M. gastri | 15754 | 27.6 | 65.1 | 9.6 | 22.3 |
| M. gordonae | 1447 | 50.7 | 55.2 | 3.1 | 0.4 |
| M. haemophilum | 29548 | 40.7 | 60.7 | 0.4 | 12.4 |
| M. intracellulare- | 3950 | 38.8 | 48.3 | 0.9 | 5.4 |
| M. kansasii | 12478 | 53.4 | 27.3 | 24.5 | 27.8 |
| M. malmoense | 29571 | 3.1 | 38.4 | 0.8 | 1.5 |
| M. marinum | 827 | 41.7 | 4.1 | 4.8 | 0.1 |
| M. nonchromogenicum | '930 | 35.0 | 42.9 | 0.5 | 16.4 |
| M. phlei | 11758 | 23.7 | 0.6 | 1.8 | 0.6 |
| M. scrofulaceum | 19981 | 35.1 | 66.9 | 0.9 | 26.4 |
| M. schimoidei | 27962 | 34.6 | 1.4 | 1.3 | 4.8 |
| M. simiae | 25275 | 45.9 | 44.0 | 5.3 | 0.1 |
| M. smegmatis | e14468 | 31.3 | 4.0 | 5.6 | 0.1 |
| M. szulgai | 23069 | 19.4 | 22.3 | 1.5 | 3.0 |
| M. terrae | 15755 | 25.6 | 21.7 | .4 | 12.3 |
| M. thermoresistible | 19527 | 20.3 | 34.5 | 3.1 | 17.6 |
| M. triviale | 23292 | 37.3 | 4.6 | 4.3 | 0.1 |
| M. tuberculosis (avir) | 25177 | 38.5 | 26.3 | 11.3 | 23.0 |
| M. tuberculosis (virul) | 27294 | 13.8 | 12.4 | 38.4 | 22.3 |
| M. ulcerans | 19423 | 33.9 | 28.7 | 0.4 | 8.9 |
| M. vaccae | 15483 | 8.8 | 36.2 | 4.8 | 3.2 |
| M. xenopi | 19971 | 38.4 | 2.1 | 3.8 | 0.2 |

TABLE 23

HYBRIDIZATION OF THE MYCOBACTERIUM PROBES 1–4 TO PHYLOGENETICALLY CLOSELY RELATED ORGANISMS

| Organism | ATCC # | % Probe 1 Bound | % Probe 2 Bound | % Probe 3 Bound | % Probe 4 Bound |
|---|---|---|---|---|---|
| Actinomadura madurae | 19425 | 0.2 | 0.3 | 0.2 | 0.1 |
| Actinoplanes italicus | 10049 | 0.4 | 0.5 | 0.3 | 0.2 |
| Arthrobacter oxidans | 14358 | 0.2 | 0.4 | 0.3 | 0.1 |
| Brevibacterium | e9172 | 0.3 | 0.3 | 0.3 | 0.1 |

TABLE 23-continued

HYBRIDIZATION OF THE MYCOBACTERIUM PROBES 1–4 TO PHYLOGENETICALLY CLOSELY RELATED ORGANISMS

| Organism | ATCC # | % Probe 1 Bound | % Probe 2 Bound | % Probe 3 Bound | % Probe 4 Bound |
|---|---|---|---|---|---|
| linens | | | | | |
| Corynebacterium xerosis | 373 | 0.4 | 0.3 | 0.3 | 0.1 |
| Dermatophilus congolensis | 14367 | 0.4 | 0.6 | 0.3 | 0.1 |
| Microbacterium lacticum | 8180 | 0.2 | 0.3 | 0.2 | 0.1 |
| Nocardia asteroides | 19247 | 0.3 | 0.3 | 0.4 | 0.1 |
| Nocardia otitidiscaviarum | 14629 | 0.4 | 0.3 | 0.6 | 0.1 |
| Nocardiopsis dassonvillei | 23218 | 0.3 | 0.2 | 0.3 | 0.1 |
| Oerskovia turbata | 33225 | 0.2 | 0.2 | 0.3 | 0.1 |
| Oerskovia xanthineolytica | 27402 | 0.2 | 0.3 | 0.3 | 0.1 |
| Rhodococcus aichiensis | 33611 | 0.4 | 0.2 | 0.3 | 0.2 |
| Rhodococcus aurantiacus | 25938 | 0.3 | 0.4 | 0.3 | 0.2 |
| Rhodococcus bronchialis | 25592 | 0.4 | 0.3 | 0.3 | 0.1 |
| Rhodococcus chubuensis | 33609 | 0.6 | 0.4 | 0.3 | 0.3 |
| Rhodococcus equi | 6939 | 0.4 | 0.4 | 0.4 | 0.5 |
| Rhodococcus obuensis | 33610 | 0.5 | 0.5 | 0.3 | 0.1 |
| Rhodococcus sputi | 29627 | 0.4 | 0.5 | 0.4 | 0.3 |

EXAMPLE 9

Mycoplasmas are small, aerobic bacteria lacking cell walls. *Mycoplasma pneumoniae* is estimated to cause 8–15 million infections per year. The infections may be asymptomatic or range in severity from mild to severe bronchitis and pneumonia. The organism is believed to cause about 10% of pneumonias in the general population and 10–50% of the pneumonias of members of groups in prolonged, close contact such as college students and military personnel.

Diagnosis until now has required isolation of the organism in culture or demonstration of an increase in antibody titer. Culturing of the organism involves inoculation of respiratory tract specimens onto agar or biphasic media containing bacterial growth inhibitors. Examination for growth at 3–4 and 7–10 days is used to establish the presence or absence of any mycoplasma. *Mycoplasma pneumoniae* must then be identified by hemadsorption (the ability of *M. pneumoniae* to adhere sheep or guinea pig erythrocytes), hemolysis (the ability of *M. pneumoniae* to produce beta hemolysis of sheep or guinea pig erythrocytes in blood agar), growth inhibition by specific antibodies, or immunofluorescence with specific antibodies. The present invention has significant advantages over each of these prior art methods both because of the simplicity of the test and because of the greatly reduced time necessary to achieve a diagnosis.

A probe specific for the 5S rRNA of *M. pneumoniae* was obtained by a comparison of known rRNA sequences. The particular sequences aligned were from *M. pneumoniae, M. gallisepticum* and *Ureaplasma urealyticum* (Rogers, M. J. et al. 1985, Proc. Natl. Acad. Sci. USA, 82 (1160–1164), *M. capricolum* (Hori, H. et al. 1981, Nucl. Acids Res. 9, 5407–5410) and Spiroplasma sp. (Walker, R. T. et al. 1982 Nucl. Acids Res. 10, 6363–6367). The alignments were performed as described above and outlined at page 6. 5S rRNA can be isolated and sequenced as outlined in Rogers et al., or a primer can be made which is complementary to a conserved region in the 5S rRNA and sequencing performed as outlined in Examples 1–4. The conserved region of 5S rRNA is documented in Fox, G. E. and Woese, C. R., 1975, Nature 256: 505–507. The following sequence was determined to be specific for Mycoplasma pneumoniae:

GCTTGGTGCTTTCCTATTCTCACTGAAA-CAGCTACATTCGGC.

The sequence is complementary to a unique segment found in the 5S rRNA of *Mycoplasma pneumoniae* in the region corresponding to bases 65–108 of *E. coli* 5S rRNA, and was selected by comparison to 5S rRNA sequences from *Mycoplasma gallisepticum, Spiroplasma mirum* and *Ureaplasma urealyticum*. The oligonucleotide probe was characterized as described above. The size of the probe was 42 bases. The probe has a Tm of 71.5° C.

To demonstrate the reactivity of this sequence for *Mycoplasma pneumoniae*, the probe was tested in hybridization reactions under the following conditions. $^{32}$P-end-labelled oligonucleotide probe was mixed with 1 microgram ($7 \times 10^{-13}$ moles) of purified rRNA from *Mycoplasma pneumoniae* and reacted in 0.12 M PB (equimolar amounts of $Na_2HPO_4$ and $NaH_2PO_4$), 1 mM EDTA and 0.2% SDS (sodium dodecyl sulfate) at 65° C. for 60 minutes in a final volume of 50 microliters. In separate tubes the probe was mixed with the hybridization buffer with and without target *Mycoplasma pneumoniae* rRNA present. Following separation on hydroxyapatite as outlined previously the hybrids were quantitated by scintillation counting. These results are shown in Table 24.

TABLE 24

HYBRIDIZATION OF THE *M. PNEUMONIAE* 5S rRNA DNA PROBE TO HOMOLOGOUS TARGET rRNA*/

| | plus rRNA | minus rRNA |
|---|---|---|
| *M. pneumoniae* 5S probe | 85–95% | 0.5% |

*% Hybridization = $\frac{\text{cpm bound to hydroxyapatite}}{\text{total cpm added to reaction}}$ This data shows that the probe has a high extent of reaction to its homologous target and very little non-specific binding to the hydroxyapatite.

Specificity of the *M. pneumoniae* 5S probe was tested by mixing the $^{32}$P labelled probe with rRNA released from cells from other Mycoplasma species. All hybridization assays were carried out as described in Example 1. Table 25 indicates that the probe is specific for *Mycoplasma pneumoniae* and does not react with any other Mycoplasma species.

TABLE 25

HYBRIDIZATION OF *M. PNEUMONIAE* PROBE TO OTHER MYCOPLASMA SPECIES

| Organism | ATCC # | % Probe Bound |
|---|---|---|
| *Acholeplasma laidlawii* | 14089 | 3.3 |
| *M. buccale* | 23636 | 1.7 |
| *M. capricolum* | 23205 | 2.4 |
| *M. columbinsale* | 33549 | 1.4 |
| *M. faucium* | 25293 | 1.4 |
| *M. fermentans* | 15474 | 1.0 |
| *M. gallisepticum* | 19610 | 1.8 |
| *M. gallopavonis* | 33551 | 1.6 |
| *M. genitalium* | 3353c | 1.7 |
| *M. hominis* | 14027 | 1.3 |
| *M. orale* | 23714 | 1.8 |
| *M. pneumoniae* | 15531 | 78.0 |
| *M. primatum* | 15497 | 1.6 |
| *M. salivarium* | 23064 | 0.6 |
| *Spiroplasma mirum* | | 2.3 |

As shown in Table 26, the probe did not react with any other closely related or phylogenetically diverse species of bacteria.

TABLE 26

HYBRIDIZATION OF *M. PNEUMONIAE* PROBE TO A PHYLOGENETIC CROSS SECTION OF BACTERIA

| Organism | ATCC # | % Probe Bound |
|---|---|---|
| *Corynebacterium xerosis* | 373 | 1.4 |
| *Haemophilus influenzae* | 19418 | 1.4 |
| *Klebsiella pneumoniae* | 23357 | 1.3 |
| *Legionella pneumophila* | 33152 | 1.8 |
| *Mycobacterium tuberculosis* (avir) | 25177 | 1.6 |
| *Mycoplasma pneumoniae* | 15531 | 52 |
| *Neisseria meningitidis* | 13077 | 0.6 |
| *Propionibacterium acnes* | 6919 | 2.0 |
| *Pseudomonas aeruginosa* | 25330 | 1.6 |
| *Staphylococcus aureus* | 12598 | 2.0 |
| *Streptococcus pneumonia* | c6306 | 1.9 |

Four additional probe sequences (numbered 2–5 below) specific for *Mycoplasma pneumonias* were obtained by utilizing four unique primers complementary to conserved regions on 16S rRNA. The regions correspond, respectively, to bases 190–230; 450–490; 820–860; and 255–1290 of *E. coli* 16s rRNA. Probe sequence #1 was obtained using a primer with the sequence 5'-GGCCGTTACCCCACCTAC-TAGCTAAT-3'. Probe sequence #2 was obtained with a primer with the sequence 5'-GTATTACCGCGGCT-GCTGGC-3'. Probe sequence #3 was obtained with a primer with the sequence 5'-CCGCTTGTGCGGGCCCCCGT-CAATTC-3'. Probe sequence #4 was obtained using a primer with the sequence 5'-CGATTACTAGCGATTCC-3'. Sequencing reactions were performed as outlined in previous examples. The pneumoniae sequences were compared with sequences from *Mycoplasma genitalium, Mycoplasma capricolum, Mycoplasma gallisepticum* and *Spiroplasma mirum*.

The following probe sequences were characterized by criteria described in example one of the parent application and were shown to be specific for *Mycoplasma pneumoniae*:

2. AATAACGAACCCTTGCAGGTC-CTTTCAACTTTGAT

3. CAGTCAAACTCTAGCCATTACCT-GCTAAAGTCATT

4. TACCGAGGGGATCGCCCCGACAGCTAGTAT

5. CTTTACAGATTTGCTCACTTTTA-CAAGCTGGCGAC.

Probe #2 is 35 bases in length and has a Tm of 67° C.
Probe #3 is 35 bases in length and has a Tm of 66° C.
Probe #4 is 30 bases in length and has a Tm of 69° C.
Probe #5 is 35 bases long with a Tm of 66° C.

When the four probes were mixed and used in hybridization assays at 60° C. in the same manner as previous examples, they were found to be specific for *M. pneumoniae*. The probes do not cross react with other respiratory pathogens or with any organism representing the bacterial phylogenetic tree (Table 28).

TABLE 27

HYBRIDIZATION OF *MYCOPLASMA PNEUMONIAE* PROBES 2–5 TO MYCOPLASMA SPECIES

| Organism | ATCC # | % Probe Bound |
|---|---|---|
| *Acholesplasma axanthum* | 27378 | 0.34 |
| *Acholeplasma laidlawii* | 14089 | 0.30 |
| *Mycoplasma arginini* | 23838 | 0.20 |
| *Mycoplasma arthritidis* | 19611 | 0.49 |
| *Mycoplasma bovigenitalium* | 19852 | 0.18 |
| *Mycoplasma bovis* | 25523 | 0.43 |
| *Mycoplasma buccale* | 23636 | 0.37 |
| *Mycoplasma californicum* | 33451 | 0.79 |
| *Mycoplasma capricolum* | 23205 | 0.38 |
| *Mycoplasma columbinasale* | 33549 | 0.54 |
| *Mycoplasma columborale* | 29258 | 0.50 |
| *Mycoplasma faucium* | 25293 | 0.45 |
| *Mycoplasma fermentans* | 15474 | 0.27 |
| *Mycoplasma gallisepticum* | 19610 | 0.25 |
| *Mycoplasma gallopavonis* | 33551 | 0.47 |
| *Mycoplasma genitalium* | 33530 | 2.5 |
| *Mycoplasma hominis* | 14027 | 0.52 |
| *Mycoplasma hyorhinis* | 17981 | 0.46 |
| *Mycoplasma orale* | 23714 | 0.56 |
| *Mycoplasma pneumoniae* | 15531 | 34.0 |
| *Mycoplasma primatum* | 15497 | 0.71 |
| *Mycoplasma pulmonis* | 19612 | 0.68 |
| *Mycoplasma salivarium* | 23064 | 0.46 |
| *Spiroplasma citri* | 29416 | 0.60 |
| *Spiroplasma mirum* | 29335 | 0.52 |

TABLE 28

HYBRIDIZATION OF *MYCOPLASMA PNEUMONIA* PROBES 2–5 WITH OTHER BACTERIA

| Organism | ATCC # | % Probe Bound |
|---|---|---|
| *Actinomyces israelii* | 10049 | 1.0 |
| *Bacteroides fragilis* | 23745 | 1.4 |
| *Bifidobacterium breve* | 15700 | 1.0 |
| *Bordetella bronchiseptica* | 10580 | 0.9 |
| *Clostridium innocuum* | 14501 | 1.0 |
| *Clostridium pasteurianum* | 6013 | 0.9 |
| *Clostridium perfringens* | 13124 | 1.1 |
| *Clostridium ramosum* | 25582 | 1.0 |
| *Corynebacterium xerosis* | 373 | 0.8 |
| *Erysipelothrix rhusiopathiae* | 19414 | 1.1 |
| *Escherichia coli* | 11775 | 1.0 |
| *Haemophilus influenzae* | 19418 | 0.9 |
| *Klebsiella pneumoniae* | 15531 | 1.0 |
| *Lactobacillus acidophilus* | 4356 | 1.4 |
| *Legionella pneumophila* | 33154 | 0.8 |
| *Listeria monocytogenes* | 15313 | 1.2 |
| *Moraxella osloensis* | 19976 | 1.1 |
| *Mycobacterium tuberculosis* | 25177 | 1.0 |
| *Neisseria meningitidis* | 13077 | 1.0 |
| *Pasteurella multocida* | 6529 | 1.6 |

TABLE 28-continued

HYBRIDIZATION OF *MYCOPLASMA PNEUMONIA* PROBES 2–5 WITH OTHER BACTERIA

| Organism | ATCC # | % Probe Bound |
| --- | --- | --- |
| Peptococcus magnus | 14955 | 0.9 |
| Propionibacterium acnes | 6919 | 1.1 |
| Psuedomonas aeruginosa | 25330 | 1.0 |
| Staphylococcus aureus | 12600 | 1.0 |
| Streptococcus faecalis | 19433 | 1.5 |
| Streptococcus mitis | 9811 | 1.0 |
| Streptococcus pneumoniae | 6306 | 1.0 |
| Streptococcus pyogenes | 19615 | 1.1 |

EXAMPLE 10

The genus Legionella contains 22 species which are all potentially pathogenic for humans. These organisms cause Legionnaires' disease, an acute pneumonia, or Pontiac fever, an acute, non-pneumonic, febrile illness that is not fatal. Legionella species have also been shown to be responsible for nosocomial pneumonia occuring predominantly among immunocompromised patients.

Legionellosis, which includes Legionnaires' disease and Pontiac fever, is diagnosed on the basis of clinical symptoms, either direct or indirect fluorescence antibody tests, and by culture using a buffered charcoal yeast extract (BCYE) agar containing selective antimicrobial agents. There is no single definitive genus test known in the prior art. (See Bergey's Manual of Systematic Bacteriology at page 283, (ed. 1984 ) ) . The fluorescent antibody tests are not able to identify all species of Legionella, but only those few for which antibodies exist. The culture method is not definitively diagnostic for Legionella species.

The oligonucleotide sequences described below, when used as probes in a nucleic acid hybridization assay, accurately identify all species of Legionella. This assay is more sensitive than culture or antibody tests and shortens significantly the time of identification and, thus, diagnosis. The assay, therefore, represents a significant improvement over prior diagnostic methods.

Three probe sequences specific for the genus Legionella were obtained by utilizing three unique primers complementary to conserved regions on both 16S and 23S rRNA. Sequence 1 was obtained by using a 16S primer with the sequence 5'-TCT ACG CAT TTC ACC GCT ACA C-3'. Probe sequence 2 was obtained with a 23S primer of sequence 5'-CAG TCA GGA GTA TTT AGC CTT-3'. Probe sequence 3 was obtained with a 16S primer of sequence 5'GCT CGT TGC GGG ACT TAA CCC ACC AT-3'. Sequencing with these primers was performed as described for previous examples.

The following three sequences were characterized by the criteria described in Example 1 and were shown to be specific for the genus Legionella. The phylogenetically nearest neighbors *Escherichia coli, Pseudomonas aeruginosa, Vibrio parahaemolyticus* and *Acinetobacter calcoaceticus* were used as comparisons with sequences from Legionella species.

1. TACCCTCTCCCATACTCGAGTCAACCAGTATTATCTGACC

2. GGATTTCACGTGTCCCGGCCTACTTGTTCGGGTGCGTAGTTC

3. CATCTCTGCAAAATTCACTGTATGTCAAGGGTAGGTAAGG.

Sequence 1, from 16S rRNA, is 40 bases in length and has a Tm of 72° C. Sequence 2, from 23S rRNA, is 42 bases in length and has a Tm of 73° C. Sequence 3, from 16S rRNA, is 40 bases in length and has a Tm of 68° C. These sequences are capable of hybridizing to RNA of the genus Legionella in the regions corresponding respectively to, 630–675 of *E. coli* 16s rRNA; 350–395 of *E. coli* 23s rRNA; and 975–1020 of *E. coli* 16s rRNA. When mixed together the probes had a combined average Tm of 73° C. Analysis on polyacrylamide gels showed that each probe was the correct length and sequence analysis demonstrated that each was the correct sequence of bases.

When the three probes were mixed and used in a hybridization assay, they were found to be specific for the genus Legionella (Tables 29 and 30) and did not cross react with other respiratory pathogens or with any selected organism from the phylogenetic tree (Tables 31 and 32). Use of more than one probe, i.e., a mixture of probes, can result in increased assay sensitivity and/or in an increase in the number of non-vital organisms to be detected.

TABLE 29

HYBRIDIZATION OF LEGIONELLA PROBES TO HOMOLOGOUS TARGET rRNA

|  | plus rRNA | minus rRNA |
| --- | --- | --- |
| Legionella probe | 80% | 1.0% |

TABLE 30

HYBRIDIZATION OF LEGIONELLA PROBES TO LEGIONELLA SPECIES

| Organism | ATCC# | % Probes Bound |
| --- | --- | --- |
| L. anisa | 35292 | 42.0 |
| L. bozemanii | 33217 | 58.0 |
| L. cherrii | 35252 | 69.0 |
| L. dumoffii | 33279 | 57.0 |
| L. erythra | CDC#9PIW044C | 26.0 |
| L. feeleii | 35303 | 59.0 |
| L. hackeliae | 35250 | 47.0 |
| L. jamestowniensis | 35298 | 20.0 |
| L. jordanis | 33623 | 50.6 |
| L. longbeachae | 33484 | 48.0 |
| L. maceachernii | 35300 | 25.0 |
| L. micdadei | 33704 | 38.0 |
| L. oakridgensis | 33761 | 44.0 |
| L. parisiensis | 9060 | 69.0 |
| L. pneumophila 1* | 6736 | 75.0 |
| L. pneumophila 2 |  | 64.0 |
| L. pneumophila 3 |  | 73.0 |
| L. pneumophila 4 |  | 73.0 |
| L. pneumophila 5 |  | 78.0 |
| L. pneumophila 6 |  | 75.0 |
| L. pneumophila 7 |  | 73.0 |
| L. pneumophila 8 |  | 63.0 |
| L. pneumophila 11 |  | 75.0 |
| L. rubrilucens | 35304 | 12.0 |
| L. sainthelensi | 35248 | 61.0 |
| L. sainticrucis | 35301 | 24.0 |
| L. spiritensis | CDC#MSH9 | 55.0 |
| L. steigerwaltii | 7430 | 56.0 |
| L. wadsworthii | 33877 | 37.0 |

*The numbers 1–8 and 11 are serotypes of *L. pneumophila*.

TABLE 31

HYBRIDIZATION OF LEGIONELLA PROBES TO RESPIRATORY PATHOGENS

| Organism | ATCC # | % Probe Bound |
|---|---|---|
| Corynebacterium xerosis | 373 | 2.1 |
| Haemophilus influenzae | 19418 | 2.3 |
| Klebsiella pneumoniae | 23357 | 2.0 |
| Mycoplasma pneumoniae | 15531 | 2.3 |
| Neisseria meningitidis | 13090 | 2.2 |
| Pseudomonas aeruginosa | 25330 | 1.2 |
| Propionibacterium acnes | 6919 | 1.6 |
| Streptococcus pneumoniae | 6306 | 0.8 |
| Staphylococcus aureus | 25923 | 1.6 |

TABLE 32

HYBRIDIZATION OF LEGIONELLA PROBES TO A PHYLOGENETIC CROSS SECTION OF BACTERIAL SPECIES

| Organism | ATCC # | % Probe Bound |
|---|---|---|
| Acinetobacter calcoaceticus | 33604 | 1.4 |
| Branhamella catarrahalis | 25238 | 2.0 |
| Bacillus subtilis | 6051 | 1.9 |
| Bacteroides fragilis | 23745 | 2.2 |
| Campylobacter jejuni | 33560 | 1.2 |
| Chromobacterium violaceum | 29094 | 1.3 |
| Clostridium perfringens | 13124 | 1.9 |
| Deinococcus radiodurans | 35073 | 1.8 |
| Derxia gummosa | 15994 | 2.0 |
| Enterobacter aerogenes | 13048 | 1.4 |
| Escherichia coli | 11775 | 1.2 |
| Mycoplasma hominis | 14027 | 1.1 |
| Proteus mirabilis | 29906 | 1.4 |
| Pseudomonas cepacia | 11762 | 1.1 |
| Rahnella aquatilis | 33071 | 1.7 |
| Rhodospirillum rubrum | 11170 | 2.0 |
| Streptococcus mitis | 9811 | 2.0 |
| Vibrio parahaemolyticus | 17802 | 2.0 |
| Yersinia enterocolitica | 9610 | 1.2 |

Three additional probe sequences (numbered 4-6) specific for the genus Legionella were obtained by utilizing two primers complementary to conserved regions on 23S rRNA. Sequence 4 was made from a 23S primer with the sequence 5'-CCT TCT CCC GAA GTT ACG G-3'. Probe sequences 5 and 6 were made from a 23S primer of sequence 5'-AAG CCG GTT ATC CCC GGG GTA ACT TTT-3". Sequencing with these primers was performed as described for previous examples.

The following three sequences were characterized by the criteria previously described and were shown to be specific for the genus Legionella. The phylogenetically nearest neighbors *Escherichia coli*, *Pseudomonas aeruginosa*, *Vibrio parahaemolyticus* and *Actinetobacter calcoaceticus* were used for comparisons with sequences from Legionella species.

4. GCG GTA CGG TTC TCT ATA AGT TAT GGC TAG C
5. GTA CCG AGG GTA CCT TTG TGC T
6. CAC TCT TGG TAC GAT GTC CGA C

Probe 4, complementary to 23S rRNA in the region corresponding to bases 1585–1620 of *E. coli* 23s rRNA, is 31 bases long and has a Tm of 67° C. Probe 5, complementary to 23S rRNA in the region corresponding to bases 2280–2330 of *E. coli* 23s rRNA, is 22 bases long and has a Tm of 66° C. Probe 6, complementary to 23S rRNA in the same region as Probe 5, is 22 bases long and has a Tm of 63° C.

When the three probes were mixed with probe 3 above and used in a hybridization assay as described for probes 1–3, they were found to be specific for the genus Legionella (Table 33) and did not cross react with other respiratory pathogens or with any selected organism from the phylogenetic tree (Tables 34 and 35). Using more than one probe, i.e., a mixture of probes, can improve assay sensitivity and/or increase the number of non-viral organisms detected.

TABLE 33

HYBRIDIZATION OF LEGIONELLA PROBES TO LEGIONELLA SPECIES

| Organism | ATCC # | % Probes Bound |
|---|---|---|
| L. anisa | 35292 | 29.6 |
| L. bozemanii | 33217 | 35.5 |
| L. cherrii | 35252 | 29.2 |
| L. dumoffii | 33279 | 26.0 |
| L. erythra | 35303 | 32.0 |
| L. feelii | CDC #9P1WO44C | 32.0 |
| L. hackeliae | 35250 | 39.0 |
| L. jamestowniensis | 35298 | 31.2 |
| L. jordanis | 33623 | 25.7 |
| L. longbeachae | 33484 | 27.6 |
| L. maceahernii | 35300 | 39.3 |
| L. micdadei | 33204 | 31.0 |
| L. oakridgensis | 33761 | 24.4 |
| L. parisiensi | 35299 | 31.2 |
| L. pneumophila 1* | 33153 | 40.0 |
| L. pneumophila 2 | 33154 | 38.5 |
| L. pneumophila 3 | 33155 | 44.6 |
| L. pneumophila 4 | 33156 | 48.6 |
| L. pneumophila 5 | 33216 | 32.0 |
| L. pneumophila 6 | 33215 | 43.0 |
| L. pneumophila 7 | 33823 | 29.5 |
| L. pneumophila 8 | 35096 | 37.6 |
| L. pneumophila 11 | 43130 | 44.5 |
| L. rubrilucens | 35304 | 30.1 |
| L. sainthelensis | 35248 | 27.0 |
| L. sasinticrucis | 35301 | 22.0 |
| L. spiritensis | CDC#MSH9 | 40.5 |
| L. steigerwalti | 35302 | 31.7 |
| L. wadsworthii | 33877 | 30.0 |

*The numbers 1–8 and 11 are serotypes of *L. pneumophila*.

TABLE 34

HYBRIDIZATION OF LEGIONELLA PROBES TO RESPIRATORY PATHOGENS

| Organism | ATCC # | % Probe Bound |
|---|---|---|
| Corynebacterium xerosis | 373 | 0.13 |
| Haemophilum influenzae | 19418 | 0.12 |
| Klebsiella pneumoniae | 23357 | 0.13 |
| Neisseria meningitidis | 13090 | 0.14 |
| Pseudomonas aeruginosa | 25330 | 0.13 |
| Propionibacterium acnes | 6919 | 0.11 |
| Streptococcus pneumoniae | 6306 | 0.08 |
| Staphylococcus aureus | 25923 | 0.15 |

TABLE 35

HYBRIDIZATION OF LEGIONELLA PROBES TO A PHYLOGENETIC CROSS SECTION OF BACTERIAL SPECIES

| Organism | ATCC # | % Probe Bound |
|---|---|---|
| Acinetobacter calcoaceticus | 33604 | 0.12 |
| Branhamella catarrahalis | 25238 | 0.13 |
| Bacillus subtilis | 6051 | 0.09 |
| Bacteroides fragilis | 23745 | 0.12 |
| Campylobacter jejuni | 33560 | 0.06 |
| Chromobacterium violaceum | 29094 | 0.33 |

TABLE 35-continued

HYBRIDIZATION OF LEGIONELLA PROBES TO
A PHYLOGENETIC CROSS SECTION OF BACTERIAL
SPECIES

| Organism | ATCC # | % Probe Bound |
|---|---|---|
| Clostridium perfringens | 13124 | 0.07 |
| Deinococcus radiodurans | 35073 | 0.11 |
| Derxia gummosa | 15994 | 0.15 |
| Enterobacter aerogenes | 13048 | 0.26 |
| Escherichia coli | 11775 | 0.09 |
| Mycoplasma hominis | 14027 | 0.09 |
| Proteus mirabilis | 29906 | 0.09 |
| Pseudomonas cepacia | 17762 | 0.20 |
| Rahnella aquatilis | 33071 | 0.15 |
| Rhodospirillum rubrum | 11170 | 0.13 |
| Streptococcus mitis | 9811 | 0.07 |
| Vibrio parahaemolyticus | 17802 | 0.11 |
| Yersinia enterocolitica | 9610 | 0.19 |

EXAMPLE 11

Chlamydia are gram-negative, non-motile, obligate intracellular bacteria. The species C. trachomatis is associated with endemic trachoma (the most common preventable form of blindness), inclusion conjunctivitis and lymphogranuloma venereum (LGV). It is a major cause of nongonococcal urethritis in men and may cause cervicitis and acute salpingitis in women. Eye disease or chlamydial pneumonia may develop in newborns passing through the infected birth canal.

There are several methods known in the art for identification of C. trachomatis in the urogenital tract, for example, by direct immunofluorescent staining or enzyme immunoassay of clinical specimens. The method of choice, however, remains culture of the organism in cycloheximide treated McCoy cells. Cell culture is followed by morphological or fluorescent antibody staining for confirmation of the organism's identity.

The inventive oligonucleotide sequences described below, when used as probes in nucleic acid hybridization assay, accurately identify Chlamydia trachomatis isolates. This assay test is equal in sensitivity to culture or antibody tests and, in the case of culture, significantly shortens the time to identification, and thus, diagnosis.

The use of probes to identify and distinguish between members of the species is novel and inventive. Indeed, Kingsbury, D. T., and E. Weiss, 1968 J. Bacteriol. 96: 1421–23 (1968); Moulder, J. W., ASM News, Vol.50, No.8, (1984) report a 10% DNA homology between C. trachomatis and C. psittaci. Moreover, these reports show that different C. trachomatis strains differ in DNA homology. Weisberg, W. G. et. al, J. Bacteriol. 167:570–574 (1986) published the 16S rRNA sequences of C. psittaci and noted that C. trachomatis and C. psittaci share a greater than 95% rRNA homology. From these reports, it may be inferred that it would be difficult to invent (1) probes capable of hybridizing to all strains of C. trachomatis; and (2) probes capable of distinguishing between C. trachomatis and C. psittaci. The following probes accomplish both objectives.

Ten probe sequences specific for Chlamydia trachomatis were made using seven unique primers complementary to conserved regions of both 16S and 23S rRNA. Probe sequence 1 was obtained from a 16S primer of sequence 5'-TCT ACG CAT TTC ACC GCT ACA C-3'. Probe sequence 2 was obtained with a 16S primer of sequence 5'-CCG CTT GTG CGG GCC CCC GTC AAT TC-3'. Sequences 3 and 4 were obtained using a 16S primer with the sequence 5'-GGC CGT TAC CCC ACC TAC TAG CTA AT-3'. Probe sequences 5 and 6 were obtained with a 23S primer of sequence 5'-CTT TCC CTC ACG GTA-3'. Probe sequences 7 and 8 were obtained with a 23S primer of sequence 5'-CCT TCT CCC GAA GTT ACG G-3'. Probe sequence 9 was obtained with a 23S primer of sequence 5'-TCG GAA CTT ACC CGA CAA GGA ATT TC-3'. Probe sequence 10 was obtained with a primer of sequence 5'-CTA CTT TCC TGC GTC A-3'.

The following ten sequences were characterized using the criteria described in Example 1 and were shown to be specific for the rRNA of Chlamydia trachomatis. The phylogenetically nearest neighbor Chlamydia psittaci was used for comparison with Chlamydia trachomatis sequence.

1. CCG ACT CGG GGT TGA GCC CAT CTT TGA CAA

2. TTA CGT CCG ACA CGG ATG GGG TTG AGA CCA TC

3. CCG CCA CTA AAC AAT CGT CGA AAC AAT TGC TCC GTT CGA

4. CGT TAC TCG GAT GCC CAA ATA TCG CCA CAT TCG

5. CAT CCA TCT TTC CAG ATG TGT TCA ACT AGG AGT CCT GAT CC

6. GAG GTC GGT CTT TCT CTC CTT TCG TCT ACG

7. CCG TTC TCA TCG CTC TAC GGA CTC TTC CAA TCG

8. CGA AGA TTC CCC TTG ATC GCG ACC TGA TCT

9. CCG GGG CTC CTA TCG TTC CAT AGT CAC CCT AAA AG

10. TAC CGC GTG TCT TAT CGA CAC ACC CGC G

Sequence 1, from 16S rRNA, is 30 bases in length and has a Tm of 66° C. Sequence 2, from 16S rRNA, is 32 bases in length and has a Tm of 67° C. Sequence 3, from S rRNA, is 39 bases in length and has a Tm of 70° C. Sequence 4, from 16S rRNA, is 33 bases in length and has a Tm of 69° C. Sequence 5, from 23S rRNA, is 41 bases in length and has a Tm of 71° C. Sequence 6, from 23S rRNA, is 30 bases in length and has a Tm of 72° C. Sequence 7, from 23S rRNA, is 33 bases in length and has a Tm of 72 C. Sequence 8, from 23S rRNA, is 30 bases in length and has a Tm of 71° C. Sequence 9, from 23S rRNA is 35 bases in length and has a Tm of 74° C. Sequence 10 is 28 bases in length and has a Tm of 72° C.

The reactivity and specificity of the probes was tested hybridization assay. $^{32}$P-end-labeled oligonucleotide probes 1 and 2 were mixed with purified RNA or RNA released from at least 107 organisms in 0.55 ml of 41% diisobutyl sulfosuccinate, 3% sodium dodecyl sulfate, 0.03 M sodium phosphate pH 6.8, 1 mM EDTA, 1 mM EGTA at 60° C. (probe 1) or 64° C. (probe 2) for 1 hour. Hybrids were bound to hydroxyapatite as described in previous examples and the amount of radioactivity bound was determined by scintillation counting. Table 36 shows that probes 1 and 2 hybridize well to all serotypes of C. trachomatis tested. Probe 1 does not react with any strain of C. psittaci tested and probe 2 does not react with two of the strains. Probe 2 does react with the ovine polyarthritis strain of C. psittaci, an organism which is not known to infect humans. Table 37 demonstrates the reactivity and specificity of probes 3–9 when $^{125}$I-labeled and used as a mix. In this case, the hybrids were bound to cationic magnetic particles as described in Arnold et al., U.S. patent App. Ser. No. 020,866 filed Mar. 2, 1987. These probes hybridize well to all strains of C. trachomatis tested and not to any strains of *C. psittaci*. Probes 3–9 were further tested against a panel of organisms commonly found in the urogenital tract (Table 38) and a phylogenetic cross section of organisms (Table 39). In all cases, the probes were shown to be specific. Probe 10 is 25% non-homologous to *C. psittaci* and also should be specific for *C. trachomatis*.

TABLE 36

HYBRIDIZATION OF CHLAMYDIA TRACHOMATIS
PROBES 1 AND 2 TO CHLAMYDIA RNA

| | | % Probe Bound | |
|---|---|---|---|
| Organism | ATCC # | Probe 1 | Probe 2 |
| Chlamydia trachomatis serotype C | VR578 | 22 | 39 |
| Chlamydia trachomatis serotype E | VR348B | 27 | 48 |
| Chlamydia trachomatis serotype G | VR878 | 20 | 44 |
| Chlamydia trachomatis serotype I | VR880 | 20 | 42 |
| Chlamydia trachomatis serotype K | VR887 | 28 | 45 |
| Chlamydia psittaci guinea pig conjunctivitis strain | VR813 | 1.2 | 1.4 |
| Chlamydia psittaci ovine abortion strain | VR656 | 1.0 | 3.0 |
| Chlamydia psittaci ovine poly-arthritis strain | VR619 | 1.1 | 35.3 |

TABLE 37

HYBRIDIZATION OF *CHLAMYDIA TRACHOMATIS*
PROBES 3–9 WITH CHLAMYDIA rRNA

| Organism | Serovar | ATCC# | Ratio Counts Bound* |
|---|---|---|---|
| C. trachomatis | A | | 689 |
| C. trachomatis | B | | 560 |
| C. trachomatis | Ba | | 1066 |
| C. trachomatis | C | VR548 | 962 |
| C. trachomatis | D | | 1192 |
| C. trachomatis | E | VR348 | 1022 |
| C. trachomatis | F | | 391 |
| C. trachomatis | G | VR878 | 874 |
| C. trachomatis | H | | 954 |
| C. trachomatis | I | VR880 | 943 |
| C. trachomatis | J | | 482 |
| C. trachomatis | K | VR887 | 999 |
| C. trachomatis | L1 | | 638 |
| C. trachomatis | L2 | | 501 |
| C. trachomatis | L3 | VR903 | 821 |
| C. psittaci | | VR125 | 1.6 |
| C. psittaci | | VR629 | 0.9 |
| C. psittaci | | VR656 | 1.3 |
| C. psittaci | | VR813 | 1.2 |

*Ratio = $\frac{\text{counts bound when RNA present}}{\text{counts bound when no RNA present}}$

TABLE 38

HYBRIDIZATION OF *CHLAMYDIA TRACHOMATIS*
PROBES 3–9 TO ORGANISMS
FOUND IN THE UROGENITAL TRACT

| Organism | ATCC# | Ratio Count Bound* |
|---|---|---|
| Achromobacter xylosoxidans | 27061 | 1.9 |
| Acinetobacter lwoffii | 15309 | 1.2 |
| Branhamella catarrhalis | 25238 | 1.2 |

TABLE 38-continued

HYBRIDIZATION OF *CHLAMYDIA TRACHOMATIS*
PROBES 3–9 TO ORGANISMS
FOUND IN THE UROGENITAL TRACT

| Organism | ATCC# | Ratio Count Bound* |
|---|---|---|
| Candida albicans | 18804 | 2.4 |
| Flavobacterium meningosepticum | 13253 | 1.1 |
| Gardnerella vaginalis | 14018 | 1.3 |
| Lactobacillus acidophilus | 4356 | 0.8 |
| Listeria monocytogenes | 15313 | 0.7 |
| Mycobacterium smegmatis | 14468 | 1.1 |
| Moraxella osloensis | 19976 | 1.3 |
| Neisseria gonorrhoeae | 19424 | 2.3 |
| Pasteurella multocida | 6529 | 1.0 |
| Peptostreptococcus anaerobius | 27337 | 1.2 |
| Streptococcus agalactiae | 13813 | 4.0 |
| Streptococcus faecalis | 19433 | 2.6 |

*Ratio = $\frac{\text{counts bound when RNA present}}{\text{counts bound when no RNA present}}$

TABLE 39

HYBRIDIZATION OF *CHLAMYDIA TRACHOMATIS*
PROBES 3–9 TO
PHYLOGENETICALLY DIVERSE ORGANISMS

| Organism | ATCC# | Ratio Count Bound* |
|---|---|---|
| Bacillus subtilis | 6051 | 2.2 |
| Bacteroides fragilis | 23745 | 1.6 |
| Campylobacter jejuni | 33560 | 1.4 |
| Chromabacterium violaceum | 29094 | 1.4 |
| Deinococcus radiodurans | 35073 | 1.8 |
| Derxia gummosa | 15994 | 1.3 |
| Enterobacter aerogenes | 13048 | 1.9 |
| Escherichia coli | 11775 | 1.9 |
| Mycoplasma hominis | 14027 | 1.3 |
| Pseudomonas cepacia | 17762 | 2.2 |
| Proteus mirabilis | 29906 | 2.2 |
| Rahnella aquatilis | 33071 | 1.9 |
| Rhodospirillum rubrum | 11170 | 1.9 |
| Vibrio parahaemolyticus | 17802 | 2.0 |
| Yersinia enterocolitica | 9610 | 2.5 |

*Ratio = $\frac{\text{counts bound when RNA present}}{\text{counts bound when no RNA present}}$

EXAMPLE 12

Campylobacters are motile, microaerophilic, gram negative curved rods. The genus is quite diverse and distinct from other genera. Although the genus is well defined, some revision is occurring at the species level (Romaniuk, P. J. et al., *J. Bacteriol.* 169:2137–2141 (1987). Three Campylobacter species, *Campylobacter jejuni*, *C. coli* and *C. laridis*, cause enteritis in humans. The disease includes diarrhea, fever, nausea, abdominal pain and in some cases, vomiting. These organisms cause an estimated 2 million infections per year in the U.S. (estimate based on the number of Salmonella and Shigella induced cases of diarrheal disease). Other members of the genus cause septicemias in humans and abortion and infertility in sheep and cattle.

Diagnosis of Campylobacter enteritis is currently dependent upon growth and isolation of the organism in culture, followed by a number of biochemical tests. Optimum growth of campylobacters requires special conditions such as low oxygen tension and high temperature (42° C.). No single set of conditions is recommended for isolation of all Campylobacter species.

The oligonucleotide sequences listed below, when used in a hybridization assay, hybridize to the 16S rRNA of the Campy-lobacter species of interest. The present invention has significant advantages over the prior art methods of detection of Campylobacter because one probe can detect all Campylobacters of interest; the other two probes detect the enteric Campylobacters and one can detect human isolates of Campylobacter. In addition, the probes have advantages over the prior art in terms of ease of the assay and greatly reduced time to identification and therefore, diagnosis.

The four probes which hybridize to the 16S rRNA of Campylobacter species of interest were constructed using three unique primers complementary to 16S rRNA. Sequences 1 and 2 were made using a 16S primer with the sequences 5'-GTA TTA CCG CGG CTG CTG GCA C-3'. Sequence 3 was made using a 16S primer with the sequence 5'-CCG CTT GTG CGG GCC CCC GTC AAT TC-3'. Sequence 4 was made with a 16S primer with the sequence 5'-GCT CGT TGC GGG ACT TAA CCC AAC AT-3'.

The following sequences were characterized and shown to hybridize to *Campylobacter jejuni, E. coli* and *E. laridis*. The phylogenetically nearest neighbors *Vibrio parahaemolyticus* and *Wollinella succinogenes* were used for comparison with the campy-lobacter sequences.

1. CGC TCC GAA AAG TGT CAT CCT CC
2. CCT TAG GTA CCG TCA GAA TTC TTC CC
3. GCC TTC GCA ATG GGT ATT CTT GGT G
4. GGT TCT TAG GAT ATC AAG CCC AGG

Sequence 1, from 16S rRNA, is 23 bases in length and has a Tm of 65° C. Sequence 2, from 16S rRNA, is 26 bases in length and has a Tm of 64° C. Sequence 3, from 16S rRNA, is 25 bases in length and has a Tm of 66° C. Sequence 4, from 16S rRNA, is 24 bases in length and has a Tm of 61° C. Sequence 1 is capable of hybridizing in the region corresponding to bases 405–428 of *E. coli* 16s rRNA; Sequence 2 is capable of hybridizing in the region corresponding to bases 440–475 of *E. coli* 16s rRNA; Sequence 3 is capable of hybridizing in the region corresponding to bases 705–735 of *E. coli* 16s rRNA; Sequence 4 is capable of hybridizing in the region corresponding to bases 980–1010 of *E. coli* 16s rRNA.

The reactivity and specificity of the probes for campylobacter was tested in hybridization assays. 32p end-labeled oligonucleotide probes were mixed with purified RNA or RNA released from cells in 0.1% sodium dodecyl sulfate. 0.5 ml of hybridization solution (41% diisobutyl sulfosuccinate, 30mM sodium phosphate, pH 6.8, 0.7% sodium dodecyl sulfate, 1 mM EDTA, 1 mM EGTA) was added and the mixture incubated at 60° C. for 1 to 1.5 hour. Following incubation, 2 to 2.5 ml of separation solution (2% hydroxyapatite, 0.12 M sodium phosphate, pH6.8, 0.02% sodium dodecyl sulfate) was added and the mixture incubated at 60° C. for five minutes. The sample was centrifuged and the supernatant removed. 2.5 ml of wash solution (0.12 M sodium phosphate, pH6.8, 0.02% sodium dodecyl sulfate) was added and the sample mixed, centrifuged and the supernatant removed. The radioactivity bound to the hydroxyapatite was determined by scintillation counting.

Table 40 indicates that the probes hybridize well to the Campylobacter species of interest, *E. jejuni, E. coli,* and *E. laridis*. Probe 1 detects all of the Campylobacter species tested, probes 2 and 4 detect only the enteric campylobacters, and probe 3 detects all of the Campylobacter species except *E. sputorum,* an organism isolated from cattle. Thus all of the probes are useful for identifying campylobacter in stool samples. The choice of which probe to use for other applications would depend upon the level of specificity required (i.e., enteric campylobacters, or all Campylobacter species).

TABLE 40

HYBRIDIZATION OF CAMPYLOBACTER PROBES 1–4 TO CAMPYLOBACTER SPECIES

| | | % Probe Bound (*) | | | |
|---|---|---|---|---|---|
| Organism | ATCC # | 1 | 2 | 3 | 4 |
| Campylobacter coli | 33559 | 64 | 70 | 52 | 49 |
| C. fetus subsp. fetus | 27374 | 68 | 0.1 | 66 | 0.5 |
| C. fetus subsp. venerealis | 19438 | 66 | 0.7 | 54 | 1.2 |
| C. jejuni | 33560 | 63 | 76 | 51 | 56 |
| C. laridis | 35221 | 74 | 73 | 64 | 52 |
| C. sputorum subsp. bubulus | 33562 | 71 | 3.0 | 2.5 | 0 |

(*) % Probe Bound = cpm bound to hybroxyapatite-cpm bound when no RNA present/total cpm used in the assay Table 41 shows that the probes do not hybridize to closely related organisms or organisms found in the gastrointestinal tract.

TABLE 41

HYBRIDIZATION OF CAMPYLOBACTER PROBES 1–4 TO CLOSELY RELATED ORGANISMS AND ORGANISMS FOUND IN THE GASTRO-INTESTINAL TRACT.

| | | % Probe Bound (%) | | | |
|---|---|---|---|---|---|
| Organism | ATCC # | 1 | 2 | 3 | 4 |
| Bacteroides fragilis | 25285 | 0 | 0.2 | 0.7 | 0 |
| Escherichia coli | 11775 | 1.3 | 0.5 | 0.5 | 0 |
| Salmonella typhimurium | 14028 | 0 | 0 | 0.3 | 0 |
| Shigella boydii | 29929 | 0 | 0.2 | 0.5 | 0 |
| Shigella dysenteriae | 13313 | 0 | 0.7 | 0.2 | 0 |
| Shigella flexneri | 29903 | 0 | 0 | 0.5 | 0 |
| Shigella sonnei | 29930 | 0 | 0 | 0.1 | 0 |
| Vibrio parahaemolyticus | 17802 | 0 | 1.9 | 0.1 | 0 |
| Wollinella succinogenes | 29543 | 0.4 | 2.1 | 2.2 | 0 |
| Yersinia pseudotuberculosis | 29833 | 0.6 | 0.2 | 1.7 | 0.3 |

(*) % probe bound = cpm bound to hydroxyapatite-cpm bound when no RNA present/total cpm used in the assay The probes specific for the enteric Campylobacters, probes 2 and 4, were further tested and shown not to react with rRNAs of other organisms found in the gastrointestinal tract.

TABLE 42

HYBRIDIZATION OF CAMPYLOBACTER PROBES 2 AND 4 TO ORGANISMS FOUND IN THE GASTRO-INTESTINAL TRACT.

| | | % Probe Bound (*) | |
|---|---|---|---|
| Organism | ATCC # | Probe 2 | Probe 4 |
| Citrobacter diversus | 27156 | 0 | 0 |
| Clostridium perfringens | 13124 | 0 | 0 |
| Enterobacter cloacae | 13047 | 0 | 0 |
| Klebsiella pneumoniae | 23357 | 0 | 0.5 |
| Proteus mirabilis | 25933 | 0 | 0 |
| Serratia marcescens | 13880 | 0 | 0 |
| Staphylococcus aureus | e12600 | | |
| Staphylococcus epidermidis | 14990 | 0 | 0.3 |
| Streptococcus bovis | 33317 | 0 | 0 |

(*) % probe bound = cpm bound to hydroxyapatite-cpm bound when no RNA present/total cpm used in the assay

EXAMPLE 13

Streptococci are gram positive, oxidase negative coccoid bacteria. The genus has been divided into 18 groups, A–R, on the basis of group-specific carbohydrates. Group D streptococci are further subdivided into the enteroccocci (*S. faecium, S. faecalis, S. avium* and *S. gallinarum* and the non-enterococci *S. bovis* and *S. equinus. S. faecium, S. faecal* is and *S. avium* are considered the medically important enteroccocci. Some species of streptococcus are human pathogens; others are normal flora in the mouth and intestine but are capable of causing disease when introduced to other sites. Two examples are *S. faecium* and *S. faecalis* which are normally found in the intestine but may spread to cause bacteremia, wound infections, and as many as 10% of the urinary tract infections in the U.S.

Current methods of detection of enterococci require culture of the specimen for 18–72 hours followed by a battery of biochemical tests. The oligonucleotide sequence shown below, when used in a hybridization assay, accurately detects *Streptococcus faecalis, S. avium,* and *S. faecium.* The inventive probe does not cross react with other Streptococci or Staphylococci which are very closely related in DNA homology. (Kiepper-Baez, 1981, 1982, Schliefer 1984.) The current invention also reduces the number of tests which must be run on a sample and greatly reduces the time to identification and thus, diagnosis. This represents a significant improvement over prior art methods.

The probe sequence was identified using a primer complementary to 16S rRNA with the sequence 5'-CCG CTT GTG CGG GCC CCC GTC AAT TC-3'. The following sequence was characterized and shown to be specific for three enterococci, *S. faecium, S. faecalis* and *S. avium.* The phylogenetically nearest neighbors *S. agalactiae, S. bovis, S. pneumoniae* and *S. pyogenes* were used for comparison with the sequences of interest.

1. TGC AGC ACT GAA GGG CGG AAA CCC TCC AAC ACT TA

The sequence is 35 bases in length and has a Tm of 72° C. It is capable of hybridizing in the region corresponding to bases 825–860 of *E. coli* 16s rRNA. To demonstrate the reactivity and specificity of the probe, it was used in a hybridization assay with purified RNA or RNA released from cells. A suspension containing at least $10^7$ cells in 2% sodium dodecyl sulfate was vortexed in the presence of glass beads. 0.1 ml of suspension was mixed with 0.1 ml of hybridization buffer (0.96 M sodium phosphate, pH 6.8, 0.002 M EDTA, 0.002 M EGTA) and incubated at 65° C. for 2 hours. After incubation, 5 ml of 2% hydoxyapatite, 0.12 M sodium phosphate pH 6.8, 0.02% sodium dodecyl sulfate was added and the mixture was incubated at 65° C. for 10 minutes. The sample was centrifuged and the supernatant removed. Five ml of wash solution (0.12 M phosphate buffer, pH 6.8, 0.02% sodium dodecyl sulfate) was added and the samples were vortexed, centrifuged, and the supernatant removed. The amount of radioactivity bound to the hydroxyapatite was determined by scintillation counting. Table 43 shows that the probe reacts well with *S. faecium, S. faecalis,* and *S. avium,* and does not react with other closely related organisms.

TABLE 43

HYBRIDIZATION OF THE ENTEROCOCCUS PROBE TO CLOSELY RELATED ORGANISMS.

| Organism | ATCC # | % Probe Bound |
|---|---|---|
| Staphylococcus aureus | 12600 | 1.4 |
| Streptococcus agalactiae | 13813 | 1.5 |
| Streptococcus avium | 14025 | 22.7 |
| Streptococcus bovis | 33317 | 1.4 |
| Streptococcus faecalis | 19433 | 45.3 |
| Streptococcus faecium | 19434 | 43.0 |
| Streptococcus mitis | 9811 | 1.5 |
| Streptococcus pneumoniae | 6306 | 1.5 |
| Streptococcus pyogenes | 19615 | 1.3 |

EXAMPLE 14

Pseudomonads are gram-negative, non-sporeforming, nonfermentative bacilli. Pseudomonads are common inhabitants of soil and water and rarely infect healthy individuals. When the organisms encounter already compromised patients, they can cause a variety of clinical syndromes including wound infections, post-surgical infections, septicemia, infant diarrhea and respiratory and urinary tract infections. Members of the genus Pseudomonas are particularly important to identify in a clinical sample because of the resistance of the organisms to antibiotics. Nucleic acid homology studies have divided the genus into five homology classes known as RNA groups I–V. Eighty-three percent of all clinical isolates of Pseudomonas are from RNA group I and *Pseudomonas aeruginosa* is by far the most common species isolated.

Current methods of detection of pseudomonas require culture of a patient sample for 24–72 hours, followed by a battery of biochemical tests. The oligonucleotide sequence below, when used in a hybridization assay, detects the clinically important group I pseudomonas. The present invention reduces the number of tests which must be run on a sample, and reduces the time to detection. This represents a significant improvement over prior art methods.

The sequence was obtained with a primer complementary to a conserved region on 23S rRNA with the sequence 5'-CTT TCC CTC ACG GTA-3'. The following sequence was shown to detect group I pseudomonads:

1. CAG ACA AAG TTT CTC GTG CTC CGT CCT ACT CGA TT

The probe is 35 bases in length and has a Tm of 70° C. It is capable of hybridizing to the RNA of group I Pseudomonas in the region corresponding to bases 365–405 of *E. coli* 23s rRNA. To demonstrate the reactivity and specificity of the probe, it was used in a hybridization assay. $^{32}$P-end-labeled oligonucleo-tide was mixed with RNA released from at least $10^7$ organisms by standard methods in 0.48 M sodium phosphate pH 6.8, 1% sodium dodecyl sulfate, 1 mM EDTA, 1 mM EGTA and incubated at 65° C. for two hours. After incubation, the RNA:DNA hybrids were bound to hydroxyapatite as described for previous examples and the radio-activity bound was determined by scintillation counting. Table 44 demonstrates that the probe reacted well with all 8 species of group I pseudomonads that were tested. The probe did not react with RNA from group II or group V organisms. A low reaction was seen with *Pseudomonas acidovorans,* a group III organism which re-presents <1% of all isolates of nonfermentative bacilli from clinical samples. Table 45 demonstrates that the probe does not react with other closely related organisms which were tested.

TABLE 44

HYBRIDIZATION OF PSUEDOMONAS GROUP I PROBE TO PSEUDOMONAS RNAs

| Organism | Group | ATCC # | % Probe* Bound |
|---|---|---|---|
| Pseudomonas alcaligenes | I | 14909 | 24 |
| Pseudomonas aeruginosa | I | 10145 | 83 |
| Pseudomonas denitrificans | I | 13867 | 83 |
| Pseudomonas fluorescens | I | 13525 | 82 |
| Pseudomonas mendocina | I | 25411 | 79 |
| Pseudomonas pseudoalcaligenes | I | 17440 | 78 |
| Pseudomonas putida | I | 12633 | 80 |
| Pseudomonas stutzeri | I | 17588 | 84 |
| Pseudomonas cepacia | II | 25416 | 0 |
| Pseudomonas pickettii | II | 27511 | 1.0 |
| Pseudomonas acidovorans | III | 15668 | 11 |
| Pseudomonas maltophilia | V | 13637 | 0.2 |

*% Probe Bound = counts bound when RNA present − counts bound when no RNA present/total counts used in the assay

TABLE 45

HYBRIDIZATION OF PSEUDOMONAS GROUP I PROBE TO RNAs OF CLOSELY RELATED ORGANISMS

| Organism | ATCC # | % Probe* Bound |
|---|---|---|
| Acinetobacter calcoaceticus | 23055 | 1.6 |
| Legionella pneumophila | 33155 | 0.6 |
| Moraxella phenylpyruvica | 23333 | 0.3 |
| Morganella morganii | 25830 | 0 |
| Vibrio parahaemolyticus | 17802 | 0.6 |

*% Probe Bound = counts bound when RNA present − counts bound when no RNA present/total counts used in the assay

EXAMPLE 15

Examples 15–18 disclose probes for the *Entero-bacteriaceae,* all of which are highly related at the DNA level. Even fewer differences exist at the rRNA level. For example, Proteus vulgaris 16s rRNA is 93% homologous to *E. coli.* These factors illustrate the difficulties associated with making rRNA probes specific for this group of organisms. Nevertheless, we have invented probes for *Enterobacter cloacae, Proteus mirabilis,* Salmonella and *E. coli.*

Members of the genus Enterobacter are motile, gram negative, non-sporeforming bacilli which belong in the family Enterobacteriaceae. The genus is a large and heterogeneous group. Eight species have been defined but only 5 are clinically significant. *Enterobacter cloacae* and *E. aerogenes* are the most common isolates and are associated with genitourinary, pulmonary, blood, central nervous system and soft tissue infections in humans.

The current method for identifying *Enterobacter cloacae* from patient samples involves culture of the specimen on agar plates for 18–24 hours, followed by a battery of biochemical tests. The oligonucleotide sequence described below, when used as a probe in a nucleic acid hybridization assay, accurately identifies *Enterobacter cloacae.* The present invention reduces the number of tests which must be run on a sample, the time to identification and therefore, diagnosis, and thus represents a significant improvement over prior art methods.

The probe specific for *Enterobacter cloacae* was obtained with a primer complementary to a conserved region of 23S rRNA with the sequence 5'-CAG TCA GGA GTA TTT AGC CTT-'3.

The following sequence was characterized and shown to be specific for *E. cloacae.* The phylogenetically nearest neighbors *Escherichia coli, Klebsiella pneumoniae, Proteus vulgaris, Salmonella enteritidis,* and *Citrobacter freundii* were used as comparisons with the sequence of *E. cloacae.*

1. GTG TGT TTT CGT GTA CGG GAC TTT CAC CC

The probe is 29 bases in length and has a Tm of 68° C. It is capable of hybridizing to RNA of *E. cloacae* in the region corresponding to bases 305–340 of *E. coli* 23s rRNA. To demonstrate the reactivity and specificity of the probe for *E. cloacae,* it was used in a hybridization assay. $^{32}$P-end-labeled oligonucleotide probe was mixed with RNA released from at least $10^7$ organisms in 1% sodium dodecyl sulfate, 0.48 M sodium phosphate, pH 6.8 (0.2 ml final volume) and incubated at 60° C. for 2 hours. Following incubation, 5 ml of 2% hydroxyapatite, 0.12 M sodium phosphate pH 6.8, 0.02% sodium dodecyl sulfate was added and the mixture incubated at 60° C. for 10 minutes. The sample was centrifuged and the supernatant removed. Five ml of wash solution (0.12 M sodium phosphate, pH 6.8, 0.02% sodium dodecyl sulfate) was added, the sample vortexed, centrifuged and the supernatant removed. The amount of radioactivity bound to the hydroxyapatite was determined by scintillation counting. The results are shown in Table 46 and demonstrates that the probe reacts well with *E. cloacae* and does not react with the RNA of closely related organisms.

TABLE 46

HYBRIDIZATION OF *ENTEROBACTER CLOACAE* PROBE TO CLOSELY RELATED ORGANISMS

| Organisms Name | ATCC # | % Probe Bound |
|---|---|---|
| Citrobacter freundii | 8090 | 1.8 |
| Enterobacter aerogenes | 13048 | 1.4 |
| Enterobacter cloacae | 13047 | 27. |
| Escherichia coli | 11775 | 1.0 |
| Klebsiella pneumoniae | 13883 | 1.7 |
| Proteus mirabilis | 29906 | 0.9 |
| Proteus vulgaris | 13315 | 0.6 |
| Providencia stuartii | 29914 | 1.1 |

Table 47 shows that the probe does not react with the RNA of organisms found in urine.

TABLE 47

HYBRIDIZATION OF ENTEROBACTER CLOACAE PROBE TO ORGANISMS FOUND IN URINE.

| Organisms Name | ATCC # | % Probe Bound |
|---|---|---|
| Candida albicans | 18804 | 0.8 |
| Candida krusei | 34135 | 0.8 |
| Candida parapsilosis | 22019 | 0.9 |
| Candida topicalis | 750 | 1.1 |
| Pseudomonas aeruginosa | 10145 | 1.0 |
| Serratia marcescens | 13880 | 1.6 |
| Staphylococcus aureus | 12600 | 1.7 |
| Staphylococcus epidermidis | 14990 | 1.4 |
| Streptococcus agalactiae | 13813 | 2.5 |
| Torulopsis glabrata | 2001 | 0.9 |

EXAMPLE 16

Members of the genus Proteus are motile, gram negative, non-sporeforming bacilli which belong in the family Enterobac-teriaceae. Four species of Proteus have been described and three of them, Proteus mirabilis, P. vulgaris, and P. penneri, cause human disease.

The most common type of proteus infection involves the urinary tract, but septicemia, pneumonia and wound infections also occur. Proteus mirabilis is the species most often isolated and may account for up to 10% of all acute, uncomplicated urinary tract infections. Species, rather than genus level identification of the causative organism is desirable because of differential antibiotic susceptibility among the species.

The current method for identifying Proteus mirabilis from patient samples involves culture of the specimen on agar plates for 18-24 hours, followed by a battery of biochemical tests. The oligonucleotide sequence described below, when used as a probe in a nucleic acid hybridization assay, accurately identifies Proteus mirabilis. The present invention reduces the number of tests which must be run on a sample, the time to identification and therefore, diagnosis and treatment. This represents a significant improvement over prior art methods.

The probe specific for Proteus mirabilis was obtained with a primer complementary to a conserved region of 23S rRNA with the sequence 5'-CAG TCA GGA GTA TTT AGC CTT-3'.

The following sequence was characterized and shown to be specific for P. mirabilis. The phylogenetically nearest neighbors Escherichia coli, Klebsiella pneumoniae, Proteus vulgaris and Salmonella enteritidis were used as comparisons with the sequence of Proteus mirabilis.

1. CCG TTC TCC TGA CAC TGC TAT TGA TTA AGA CTC

This probe is capable of hybridizing to the RNA of P. mirabilis in the region corresponding to base 270-305 of E. coli 23s rRNA. The probe is 33 bases in length and has a Tm of 66° C. To demonstrate the reactivity and specificity of the probe for P. mirabilis, it was used in a hybridization assay. $^{32}$P-end-labeled oligonucleotide probe was mixed with RNA released from at least $10^7$ organisms in 1% sodium dodecyl sulfate, 0.48 M sodium phosphate, pH 6.8, 1 mM EDTA, 1 mM EGTA (0.2 ml final volume) and incubated at 64° C. for 2 hours. Following incubation, 5 ml of 2% hydroxyapatite, 0.12 M sodium phosphate pH 6.8, 0.02% sodium dodecyl sulfate was added and the mixture incubated at 64° C. for 10 minutes. The sample was centrifuged and the supernatant removed. Five ml of wash solution (0.12 M sodium phosphate, pH 6.8, 0.02% sodium dodecyl sulfate) was added, the sample vortexed, centrifuged and the supernatant was removed. The amount of radioactivity bound to the hydroxyapatite was deter-mined by scintillation counting. The results are shown in Table 48 and demonstrate that the probe reacts well with P. mirabilis and does not react with 27 other closely related bacteria. Table 49 shows that the probe does not react with 24 other phylogenetically diverse bacteria and two yeasts tested in the same manner as the organisms in Table 48.

TABLE 48

HYBRIDIZATION OF PROTEUS MIRABILIS PROBE TO CLOSELY RELATED ORGANISMS

| Organism Name | ATCC# | % Probe Bound |
|---|---|---|
| Citrobacter diversus | 27156 | 1.1 |
| Citrobacter freundii | 8090 | 1.1 |
| Citrobacter freundii | 6750 | 1.0 |
| Enterobacter aerogenes | 13048 | 1.0 |
| Enterobacter agglomerans | 27155 | 1.0 |
| Enterobacter cloacae | e13047 | 1.1 |
| Enterobacter gergoviae | 33028 | 1.0 |
| Enterobacter sakazakii | 29544 | 1.1 |
| Escherichia coli | 10798 | 1.2 |
| Escherichia coli | 11775 | 1.2 |
| Escherichia coli | 29417 | 1.2 |
| Klebsiella oxytoca | 13182 | 1.0 |
| Klebsiella ozaenae | 11296 | 1.1 |
| Klebsiella planticol | 33531 | 0.9 |
| Klebsiella pneumoniae | 13883 | 1.3 |
| Klebsiella pneumoniae | 23357 | 1.1 |
| Klebsiella rhinoscleromatis | 13884 | 1.2 |
| Klebsiella terrigena | 33257 | 1.1 |
| Klebsiella trevisanii | 33558 | 1.0 |
| Kluyvera ascorbata | 33433 | 0.9 |
| Proteus mirabilis | 25933 | 69.0 |
| Porteus penneri | 33519 | 2.5 |
| Proteus vulgaris | 13315 | 1.7 |
| Providencia alcalifaciens | 9886 | 1.1 |
| Providencia rettgeri | 29944 | 1.3 |
| Providencia stuartii | 29914 | 1.1 |
| Salmonella arizonae | 29933 | 1.1 |
| Salmonella enteritidis | 13076 | 0.8 |

TABLE 49

HYBRIDIZATION OF PROTEUS MIRABILIS PROBE TO PHYLOGENETICALLY DIVERSE ORGANISMS

| Organism Name | ATCC# | % Probe Bound |
|---|---|---|
| Acinetobacter calcoaceticus | 33604 | 0.8 |
| Bacillus subtilis | 6051 | 1.2 |
| Bacteroides fragilis | 23745 | 0.9 |
| Branhamella catarrhalis | 25238 | 0.7 |
| Campylobacter jejuni | 33560 | 1.0 |
| Candida krusei | 34135 | 0.8 |
| Chromobacterium violaceum | 29094 | 1.1 |
| Clostridium perfringens | 13124 | 0.9 |
| Deinococcus radiodurans | 35073 | 0.8 |
| Derxia gummosa | 15994 | 0.8 |
| Hafnia alvei | 13337 | 0.9 |
| Morganella morganii | 25830 | 0.9 |
| Pseudomonas aeruginosa | 10145 | 1.0 |
| Pseudomonas cepacia | 17762 | 0.9 |
| Rahnella aquatilis | 33071 | 0.9 |
| Rhodospirillum rubrum | 11170 | 0.8 |
| Serratia marcescens | 13880 | 0.9 |
| Serratia odorifera | 33077 | 0.9 |
| Staphylococcus aureus | e12600 | 0.8 |
| Staphylococcus epidermidis | 14990 | 0.8 |
| Streptococcus mitis | 9811 | 0.8 |
| Streptococcus pnuemoniae | e6306 | 0.9 |

TABLE 49-continued

HYBRIDIZATION OF PROTEUS MIRABILIS PROBE TO PHYLOGENETICALLY DIVERSE ORGANISMS

| Organism Name | ATCC# | % Probe Bound |
|---|---|---|
| *Torulopsis glabrata* | 2001 | 0.9 |
| *Vibrio parahaemolyticus* | 17802 | 0.8 |
| *Xanthomonas maltophilia* | 13637 | 1.1 |
| *Yersinia enterocolitica* | 9610 | 0.8 |

EXAMPLE 17

Members of the genus Salmonella are motile, gram negative, non-sporeforming bacilli which belong in the family Enterobacteriaceae. All salmonellae are highly related and some microbiologists consider them to be one species. Five subgroups have been identified using nucleic acid homology studies and over 1400 different serotypes have been described. All serotypes have been implicated in human enteric disease ranging from self-limited gastroenteritis with mild symptoms, to severe gastroenteritis with bacteremia, to typhoid fever, a potentially life-threatening illness. *S. cholerasuis, S. paratyphi A* and *S. typhi* are the serotypes most often associated with severe disease and bacteremia. Diagnosis of Salmonella-induced enteritis is dependent upon detection of the organism in stool samples. Because infection occurs primarily by ingestion of contaminated milk, food and water, methods for identifying Salmonella in these products before release to consumers is critical.

Current methods for detection of members of the genus Salmonella involve culture of the specimen for 1–3 days on selective media followed by a battery of biochemical tests. Often an enrichment step is needed to isolate Salmonella from clinical samples or food products. The oligonucleotide sequences shown below, when used in a hybridization assay, accurately identify members of the genus Salmonella. The present inventive probes are specific for all members of the genus and do not react with the other closely related Enterobacteriaceae genera. These inventive probes reduce the number of tests which must be run on a sample and greatly reduce the time to identification. This represents a significant improvement over prior art methods.

The probes specific for the genus Salmonella were obtained with two primers complementary to 16S and 23S rRNA. Sequence 1 was obtained using a 16S primer with the sequence 5' TTA CTA GCG ATT CCG ACT TCA 3'. Sequence 2 was obtained using a 23S primer with the sequence 5' CAG TCA GGA GTA TTT AGC CTT 3'. The following sequences were characterized and shown to be specific for the genus Salmonella:

1. CTC CTT TGA GTT CCC GAC CTA ATC GCT GGC
2. CTC ATC GAG CTC ACA GCA CAT GCG CTT TTG TGT A

Sequence 1, from 16S rRNA, is 30 bases in length and has a Tm of 73° C. Sequence 2, from 23S rRNA, is 34 bases long and has a Tm of 71° C. These probes are capable of hybridizing in the regions corresponding to bases 1125–1155 of *E. coli* 16s rRNA and 335–375 of *E. coli* 23s rRNA, respectively. To demonstrate the reactivity and specificity of probe 1 for members of the genus Salmonella, $^{32}$P-end-labeled oligonucleotide was tested as a probe in a hybridization reaction. Purified RNA, or RNA released from at least $10^7$ organisms by standard methods, was mixed with 1 ml hybridization buffer (final concentration 43% diisobutyl sulfosuccinate, 60mM sodium phosphate pH 6.8, 1 mM EDTA, 1 mM EGTA) and incubated at 72° C. for 2–12 hours. Following incubation, 5 ml of separation solution (2% hydroxyapatite, 0.12 M sodium phosphate, pH 6.8, 0.02% sodium dodecyl sulfate) was added and the sample were mixed, incubated at 72° C. for 5 minutes, centrifuged and the supernatants removed. Four ml of wash solution (0.12 M sodium phosphate pH 6.8, 0.02% sodium dodecyl sulfate) was added and the samples were vortexed, centrifuged, and the supernatants removed. The amount of radioactivity bound to the hydroxyapatite was determined by scintillation counting. The results shown in Table 50 indicate that a combination of the two probes hybridized to the 5 subgroups of Salmonella and to all 31 of the serotypes which were tested.

TABLE 50

HYBRIDIZATION OF SALMONELLA PROBES 1 AND 2 TO MEMBERS OF THE GENUS SALMONELLA

| Subgroup and Organism | | ATCC# | % Probe Bound | |
|---|---|---|---|---|
| | | | Probe 1 | Probe 2 |
| I | *Salmonella choleraesuis* | 10708 | 24 | 40 |
| I | *Salmonella enteritidis* | 13076 | 15 | 67 |
| I | *Salmonella paratyphi* A | 9150 | 1.4 | 70 |
| I | *Salmonella* sp. serotype anatum | 9270 | 40 | 26 |
| I | *Salmonella* sp. serotype cubana | 12007 | 54 | 35 |
| I | *Salmonella* sp. serotype give | 9268 | 12 | 40 |
| I | *Salmonella* sp. serotype heidelberg | 8326 | 53 | 33 |
| I | *Salmonella* sp. serotype illinois | 11646 | 36 | 46 |
| I | *Salmonella* sp. serotype montevideo | 8387 | 35 | 32 |
| I | *Salmonella* sp. serotype newington | 29628 | 52 | 34 |
| I | *Salmonella* sp. serotype newport | 6962 | 3.4 | 36 |
| I | *Salmonella* sp. serotype putten | 15787 | 34 | 39 |
| I | *Salmonella* sp. serotype saintpaul | 9712 | 28 | 30 |
| I | *Salmonella* sp. serotype senftenberg | 8400 | 38 | 43 |
| I | *Salmonella* sp. serotype simsbury | 12004 | 29 | 29 |
| I | *Salmonella* sp. serptype sloterdijk | 15791 | 34 | 30 |
| I | *Salmonella* sp. serotype thompson | 8391 | 32 | 41 |
| I | *Salmonella* sp. serotype vellore | 15611 | 35 | 2.6 |
| I | *Salmonella typhi* | 19430 | 7.0 | 21 |
| I | *Salmonella typhimurium* | 14028 | 69 | 69 |
| II | *Salmonella slalmae* | 6959 | 3.0 | 46 |
| II | *Salmonella* sp. serotype maarssen | 15793 | 6.6 | 30 |
| III | *Salmonella arizonae* | 33952 | 2.9 | 38 |
| III | *Salmonella arizonae* | 12324 | 5.5 | 42 |
| III | *Salmonella arizonae* | 29933 | 2.3 | 62 |
| III | *Salmonella arizonae* | 29934 | 63 | 12 |
| III | *Salmonella arizonae* | 12323 | 4.0 | 39 |
| III | *Salmonella arizonae* | 12325 | 51 | 1.9 |
| IV | *Salmonella* sp. serotype harmelen | 15783 | 5.8 | 8.0 |
| IV | *Salmonella* sp. serotype ochsenzoll | 29932 | 7.5 | 40 |
| V | *Salmonella* sp. serotype bongor | cdc1319 | 60 | 1.8 |

The specificity of the probes for members of the genus Salmonella was demonstrated with hybridization reactions containing RNA from organisms closely related to Salmonella. The results are shown in Table 51.

TABLE 51

HYBRIDIZATION OF SALMONELLA PROBES 1 AND 2 TO RNA OF CLOSELY RELATED ORGANISMS

| | | % Probe Bound | |
|---|---|---|---|
| Organism | ATCC# | Probe 1 | Probe 2 |
| Citrobacter freundii | 6750 | 2.2 | 0 |
| Edwardsiella tarda | 15947 | 0 | 0 |
| Enterobacter agglomerans | 27155 | 0.6 | 0 |
| Enterobacter cloacae | 13047 | 0 | 0 |
| Enterobacter sakazakii | 29544 | 0 | 0 |
| Escherichia coli | 10798 | 0 | 0 |
| Escherichia coli | 29417 | 0 | 0 |
| Klebsiella pnuemoniae | 23357 | 0.7 | 0 |
| Kluyvera ascorbata | 33433 | 0 | 0.5 |
| Proteus mirabilis | 25933 | 0.2 | 0 |
| Shigella flexneri | 29903 | 0 | 0 |

*% Probe Bound = counts bound to hydroxyapatite-counts bound when no RNA present/total counts used in assay Table 52 shows that Salmonella probes 1 and 2 do not hybridize to phylogenetically diverse organisms.

TABLE 52

HYBRIDIZATION OF SALMONELLA PROBES 1 AND 2 TO RNA OF A PHYLOGENETIC CROSS SECTION OF ORGANISMS

| | | % Probe Bound* | |
|---|---|---|---|
| Organism | ATCC# | Probe 1 & | Probe 2 |
| Acinetobacter calcoaceticus | 33604 | 1.1 | 0.1 |
| Bacillus subtilis | 6051 | 0 | 0.5 |
| Bacteroides fragilis | 23745 | 0.1 | 0 |
| Branhamella catarrhalis | 25238 | 0.9 | 0 |
| Campylobacter jejuni | 33560 | 0 | 0.2 |
| Candida krusei | 34135 | 0.4 | 0.3 |
| Chromobacterium violaceum | 29094 | 1.7 | 0 |
| Clostridium perfringens | 13124 | 0.3 | 0 |
| Deinococcus radiodurans | 35073 | 1.6 | 0.1 |
| Derxia gummosa | 15994 | 1.2 | 0 |
| Hafnia alvei | 13337 | 1.8 | 0 |
| Morganelli morganii | 25830 | 0 | 1.1 |
| Pseudomonas aeruginosa | 10145 | 0.5 | 0.7 |
| Pseudomonas cepacia | 17762 | 0 | 0 |
| Psuedomonas maltophilia | 13637 | 1.9 | 0 |
| Rahnella aquatilis | 33071 | 1.2 | 0.3 |
| Rhodospirillum rubrum | 11170 | 0.9 | 0 |
| Serratia marcescens | 13880 | 0 | 0 |
| Serratia odorifera | 33077 | 2.6 | 0.2 |
| Staphylococcus aureus | e12600 | 0.2 | 0 |
| Staphylococcus epidermidis | 14990 | 0 | 0 |
| Streptococcus mitis | 9811 | 1.2 | 0.7 |
| Streptococcus pneumoniae | e6306 | 0 | 0 |
| Torulopsis glabrata | 2001 | 0 | 0 |
| Vibrio parahaemolyticus | 17802 | 0 | 0.2 |
| Yersinia enterocolitica | 9610 | 0 | 0 |

*% Probe Bound = Counts bound to hydroxyapatite-counts bound when no RNA present/total counts used in assay

EXAMPLE 18

*Escherichia coli* is a gram negative, nonsporeforming bacillus which belongs in the family Enterobacteriaceae. Five species of Escherichia have been described: *E. coli*, which accounts for >99% of the clinical isolates, *E. hermanii*, *E. blattae*, *E. vulneris* and *E. fergusonii*. *E. coli* is a leading cause of urinary tract infections, bactermia and neonatal meningitidis, and can cause a type of gastroenteritis known as traveller's diarrhea.

The current method for identifying *E. coli* from patient samples involves culture of the specimen on agar plates for 18–72 hours, followed by a battery of biochemical tests on isolated colonies. The oligonucleotide sequence described below, when used as a probe in a nucleic acid hybridization assay, accurately detects *E. coli* even in the presence of other organisms. The present invention reduces the number of tests which must be run on a sample and reduces the time to identification and therefore diagnosis and treatment. This represents a significant improvement over prior art methods.

The probe specific for *E. coli* was derived from the published *E. coli* sequence (Brosius, et al. *Proc. Natl. Acad. Sci. U.S.A.* 75:4801–4805 (1978)), using Proteus vulgaris (Carbon, et al., *Nuc. Acids Res.* 9:2325–2333 (1981)), *Klebsiella pneumoniae, Salmonella enteritidis, Enterobacter gergoviae* and *Citrobacter freundii* for comparison. The probe sequence is shown below.

1. GCA CAT TCT CAT CTC TGA AAA CTT CCG TGG

It hybridizes to RNA of *E. coli* in the region of 995–1030 of 16s rRNA. The probe is 30 bases in length and has a $T_m$ of 66° C. To demonstrate the reactivity and specificity of the probe for *E. coli*, it was used in a hybridization assay. $^{32}$P-end-labeled oligonucleotide probe was mixed with two unlabeled oligonucleotides of sequence 5'-TGG ATG TCA AGA CCA GGT AAG GTT CTT CGC GTT GCA TCG-3' and 5'-CTG ACG ACA GCC ATG CAG CAC CTG TCT CAC GGT TCC CGA AGG CA-3' and with purified RNA, or RNA released from cells with detergent and heat, in 1% sodium dodecyl sulfate (SDS), 0.48 M sodium phosphate pH 6.8, 1 mM EDTA, 1 mM EGTA (0.2 ml final volume) and incubated at 60° C. for 2 hours. Following incubation, 5 ml of 2% hydroxyapatite, 0.12 M sodium phosphate pH 6.8, 0.02% sodium dodecyl sulfate was added and the mixture incubated at 60° C. for 10 minutes. The sample was centrifuged and the supernatant removed. Five ml of wash solution (0.12 M sodium phosphate, pH 6.8, 0.02% sodium dodecyl sulfate) was added, the sample vortexed, centrifuged and the supernatant was removed. The amount of radioactivity bound to the hydroxyapatite was determined by scintillation counting.

An example of a use for this probe would be to detect *E. coli* in urine samples. Table 53 shows that the probe detects 7 out of 8 strains of *E. coli* tested. The probe also reacts with *E. fergusonii*, an organism which would only rarely be found in urine.

Table 54 shows that the probe does not react with any other genus tested except Shigella, another organism rarely isolated from urine. These results show that the probe will be useful in detecting *E. coli* from urine samples.

TABLE 53

HYBRIDIZATION OF E. COLI TO ESCHERICHIA SPECIES

| Organism | ATCC# | % Probe Bound |
|---|---|---|
| Escherichia coli | 10798 | 70 |
| E. coli | 11775 | 67 |
| E. coli | 23722 | 58 |
| E. coli | 25404 | 68 |
| E. coli | 25922 | 55 |
| E. coli | 29417 | 72 |
| E. coli | 33780 | 0.8 |
| E. coli | 35150 | 45 |
| E. fergusonii | 35469 | 55 |
| E. hermanii | 33650 | 0.7 |
| E. vulneris | 33821 | 0.8 |

TABLE 54

HYBRIDIZATION OF THE *E. COLI* PROBE TO CLOSELY RELATED ORGANISMS

| Organism | ATCC# | % Probe Bound |
| --- | --- | --- |
| *Citrobacter freundii* | 6750 | 0.8 |
| *Citrobacter freundii* | 8090 | 0.9 |
| *Citrobacter freundii* | 29221 | 0.6 |
| *Citrobacter freundii* | 33128 | 0.6 |
| *Enterobacter aerogens* | 13048 | 1.2 |
| *Enterobacter agglomeans* | 27155 | 0.9 |
| *Enterobacter cloacae* | 13047 | 0.9 |
| *Enterobacter gergoviae* | 33023 | 0.7 |
| *Enterobacter sakazakii* | 29544 | 0.6 |
| *Klebsiella oxytoca* | 13182 | 0.7 |
| *Klebsiella pneumoniae* | 13883 | 0.7 |
| *Proteus mirabilis* | 29906 | 0.7 |
| *Proteus vulgaris* | 13315 | 0.8 |
| *Shibella boydii* | 8700 | 76 |
| *Shigella dysenteriae* | 13313 | 0.8 |
| *Shigella flexneri* | 29903 | 71 |
| *Shigella sonnei* | 29930 | 75 |

EXAMPLE 19

The bacteria encompass a morphologically and physiologically diverse group of unicellular organisms which occupy most natural environments. Although many bacteria are harmless or beneficial to their environment or host, some are harmful and cause disease. The presence of any bacteria in some locations is undesirable or indicative of disease (e.g., culture media, pharmaceutical products, body fluids such as blood, urine or cerebrospinal fluid, and tissue biopsies). Low levels of bacteria are considered acceptable in other products such as drinking water and food products. Accordingly, there is a need for a means for detecting and quantitating bacteria in a sample.

The current method of detection and quantitation of total bacteria in a sample requires culture on multiple types of media under different conditions of temperature and atmosphere. To date, no single test exists to detect or quantitate all bacteria. The oligonucleotide sequences shown below, when used in a hybridization assay, detect a broad phylogenetic cross section of bacteria. The present invention reduces the number of tests which need to be performed and also reduces the time required for the assay. Comparison of the hybridization results from an unknown sample to a set of standards will allow some quantitation of the number of bacteria present. This represents a significant improvement over prior art methods.

The bacterial probes were designed following examination of published sequences of rRNA and sequences determined at Gen-Probe. The sequences used for the comparison include *Agrobacterium tumefaciens* (Yang et al., *Proc. Natl. Acad. Sci. U.S.A.*, 82:4443, (1985), *Anacystis nidulans* (Tomioka and Sugiura. *Mol. Gen. Genet.* 191:46, (1983), Douglas and Doolittle *Nuc. Acids Res.* 12:3373, (1984), *Bacillus subtilis* (Green et al., Gene 37:261. (1985), *Bacillus stearothermophilus* (Kop et al., DNA 3:347, (1984), *Bacteroides fragilis* (Weisburg et al., *J. Bacteriol.* 164:230, (1985), *Chlamydia psittaci* (Weisburg et al., *J. Bacteriol.* 167:570. (1986)), *Desulfovibrio desulfuricans* (Oyaizu and Woese, *System. Appl. Microbiol.* 6:257, (1985); *Escherichia coli*, (Brosius et al., *Proc. Natl. Acad. Sci. U.S.A.* 77:201, (1980); *Flavobacterium heparinum* (Weisburg et al., *J. Bacteriol.* 164:230, (1985); *Heliobacterium chlorum* (Woese et al., *Science* 229:762, (1985); Mycoplasma PG50 (Frydenberg and Christiansen, *DNA* 4:127, (1985); *Proteus vulgaris* (Carbon et al., *Nuc. Acids Res.* 2325, (1981); *Pseudomonas testosteroni* (Yang et al., *Proc. Natl. Acad. Sci. U.S.A.* 82:4443, (1985); *Rochalimaea quintana* (Weisburg et al., *Science* 230:556, (1985); *Saccharomyces cerevisiae* (Rubstoy et al., *Nuc. Acids Res.* 8:5779, (1980); Georgiev et al., *Nuc. Acids Res.* 9:6953, (1981); and human (Torczynski et al., *DNA* 283, (1985); Gonzalez et al., *Proc. Natl. Acad. Sci. U.S.A.* 82:7666, (1985)).

The following sequences were shown to hybridize to a broad phylogenetic cross section of bacteria and not to yeast or human rRNA:

1. CCA CTG CTG CCT CCC GTA GGA GTC TGG GCC
2. CCA GAT CTC TAC GCA TTT CAC CGC TAC ACG TGG
3. GCT CGT TGC GGG ACT TAA CCC AAC AT
4. GGG GTT CTT TTC GCC TTT CCC TCA CGG
5. GGC TGC TTC TAA GCC AAC ATC CTG
6. GGA CCG TTA TAG TTA CGG CCG CC
7. GGT CGG AAC TTA CCC GAC AAG GAA TTT CGC TAC C

Probe 1 is 30 bases long and has a Tm of 70° C. Probe 2 is 33 bases long and has a Tm of 69° C. Probe 3 is 26 bases long and has a Tm of 67° C. Probe 4 is 27 bases long and has a Tm of 69° C. Probe 5 is 24 bases long and has a Tm of 66° C. Probe 6 is 23 bases long and has a Tm of 62° C. Probe 7 is 34 bases long and has a Tm of 66° C. Probes 1–3 hybridize to 16S rRNA in the following regions, respectively, (corresponding to *E. coli* bases) 330–365; 675–715; and 1080–1110. Probes 4–7 hybridize to 23S rRNA in the following regions, respectively, (corresponding to *E. coli* bases) 460–490; 50–1080; and 1900–1960 (probes 6 and 7). The oligonucleotides interact with regions on the rRNA which are highly conserved among eubacteria. This means that they can be used as bacterial probes in a hybridization assay. A second use is as a tool to obtain rRNA sequence. For example, an oligonucleotide can be hybridized to the rRNA of interest and extended with reverse transcriptase. The sequence of the resulting DNA can be determined and used to deduce the complementary rRNA sequence as described in the Detailed Description of the Invention.

One application of the invention is to detect bacteria in urine (bacteriuria). To demonstrate the reactivity and specificity of the probes for bacteria found in urine, they were used in hybridization assays. $^{32}$P-end-labeled or $^{125}$I-labeled oligonucleotide probes were mixed with RNA released from cells by standard methods (e.g, the sonic disruption techniques described in Murphy et al., U.S. patent App. Ser. No. 841,860, detergent with glass beads, or enzymatic lysis). Probe was mixed with RNA in 0.48 M sodium phosphate, pH 6.8, 1 mM EDTA, 1 mM EGTA, 1% sodium dodecyl sulfate (0.2 ml final volume) and hybridized at 60° C. for 2 hours. Five ml of 2% hydroxyapatite, 0.12 M sodium phosphate pH 6.8, 0.02% sodium dodecyl sulfate was added and the mixture incubated at 60° C. for 10 minutes. The mixture was centrifuged and the supernatant removed. Five ml of wash solution (0.12 M sodium phosphate, pH 6.8, 0.02% sodium dodecyl sulfate) was added and the sample was mixed, centrifuged and the supernatant removed. The amount of radioactivity bound to the hydroxyapatite was determined by scintillation counting. Tables 55–68 demonstrate the specificity of these probes and show that a combination of probes could be used to detect all bacteria which have been tested.

Table 55 shows that probe 1 hybridizes to the RNA of bacteria commonly isolated from urine and does not detect yeast RNA. Table 56 shows that probe 1 detects phylogenetically diverse bacteria and does not hybridize to human RNA.

TABLE 55

HYBRIDIZATION OF BACTERIAL PROBE 1
TO RNA OF ORGANISMS FOUND IN URINE

| Organism | ATCC# | % Probe* Bound |
|---|---|---|
| Candida albicans | 18804 | 2.6 |
| Candida krusei | 34135 | 2.2 |
| Candida parapsilosis | 22019 | 2.9 |
| Candida tropicalis | 750 | 2.5 |
| Citrobacter freundii | 8090 | 69 |
| Enterobacter aerogens | 13048 | 70 |
| Enterobacter cloacae | 13047 | 71 |
| Escherichia coli | 11775 | 67 |
| Klebsiella oxytoca | 13182 | 70 |
| Klebsiella pneumoniae | 13883 | 72 |
| Morganella morganii | 25830 | 66 |
| Proteus mirabilis | 29906 | 71 |
| Proteus vulgaris | 13315 | 67 |
| Providencia stuartii | 29914 | 69 |
| Pseudomonas aeruginosa | 10145 | 76 |
| Pseudomonas fluorescens | 13525 | 73 |
| Serratia marcescens | 13880 | 66 |
| Staphylococcus aureus | 12600 | 57 |
| Staphylococcus epidermidis | 14990 | 68 |
| Streptococcus agalactiae | 13813 | 68 |
| Streptococcus faecalis | 19433 | 51 |
| Streptococcus faecium | 19434 | 53 |
| Torulopsis glabrata | 2001 | 2.3 |
| Ureaplasma urealyticum | 27618 | 54 |

TABLE 56

HYBRIDIZATION OF BACTERIAL PROBE 1
TO RNAs OF A CROSS SECTION OF
PHYLOGENETICALLY DIVERSE ORGANISMS

| Organism | ATCC# | % Probe* Bound |
|---|---|---|
| Acinetobacter calcoaceticus | 23055 | 65 |
| Bacillus subtilis | 6051 | 73 |
| Bacteroides fragilis | 23745 | 61 |
| Branhamella catarrhalis | 25238 | 72 |
| Campylobacter jejuni | 33560 | 64 |
| Chlamydia trachomatis | VR878 | 14 |
| Chromobacterium violaceum | 29094 | 71 |
| Clostridium perfringens | 13124 | 74 |
| Corynebacterium xerosis | 373 | 38 |
| Deinococcus radiodurans | 35073 | 47 |
| Derxia gummosa | 15994 | 65 |
| Gardnerella vaginalis | 14018 | 67 |
| Hafnia alvei | 13337 | 60 |
| Lactobacillus acidophilus | 4356 | 56 |
| Moraxella oslensis | 19976 | 61 |
| Mycobacterium smegmatis | 14468 | 47 |
| Mycoplasma hominis | 14027 | 58 |
| Neisseria gonorrhoeae | 19424 | 58 |
| Rahnella aquatilis | 33071 | 74 |
| Rhodspirillum rubrum | 11170 | 73 |
| Vibrio parahaemolyticus | 17802 | 75 |
| Human | | 2.5 |

Table 57 shows that Probe 2 hybridizes to the RNA of bacteria commonly found in urine except *Ureaplasma urealyicum* and does not hybridize to yeast rRNA.

TABLE 57

HYBRIDIZATION OF BACTERIAL PROBE 2
TO RNA OF ORGANISMS FOUND IN URINE

| Organism | ATCC# | % Probe* Bound |
|---|---|---|
| Candida albicans | 18804 | 2.5 |
| Candida krusei | 34135 | 1.8 |
| Candida parapsilosis | 22019 | 1.6 |
| Candida tropicalis | 750 | 1.4 |
| Citrobacter freundii | 8090 | 61 |
| Enterobacter aerogenes | 13048 | 57 |
| Enterobacter cloacae | 13047 | 61 |
| Escherichia coli | 11775 | 67 |
| Klebsiella oxytoca | 13182 | 67 |
| Klebsiella pnuemoniae | 13883 | 51 |
| Morganella morganii | 25830 | 69 |
| Proteus mirabilis | 29906 | 69 |
| Proteus vulgaris | 13315 | 69 |
| Providencia stuartii | 29914 | 66 |
| Pseudomonas aeruginosa | 10145 | 59 |
| Pseudomonas fluorescens | 13525 | 58 |
| Serratia marcescens | 13880 | 64 |
| Staphylococcus aureus | 12600 | 60 |
| Staphylococcus epidermidis | 14990 | 60 |
| Streptococcus agalactiae | 13813 | 54 |
| Streptococcus faecalis | 19433 | 37 |
| Streptococcus faecium | 19434 | 58 |
| Torulopsis glabrata | 2001 | 1.5 |
| Ureaplasma urealyticum | 27618 | 3.2 |

Table 58 shows that probe 2 detects phylogenetically diverse bacteria and does not hybridize to human rRNA.

TABLE 58

HYBRIDIZATION OF BACTERIAL PROBE 2 TO RNAs
OF A CROSS SECTION OF PHYLOGENETICALLY
DIVERSE ORGANISMS

| Organism | ATCC# | % Probe* Bound |
|---|---|---|
| Acinetobacter calcoaceticus | 23055 | 76 |
| Bacillus subtilis | 6051 | 75 |
| Bacteroides fragilis | 23745 | 2.0 |
| Branhamella catarrhalis | 25238 | 70 |
| Campylobacter jejuni | 33560 | 2.5 |
| Chlamydia trachomatis | VR878 | 16 |
| Chromobacterium violaceum | 29094 | 61 |
| Clostridium perfringens | 13124 | 66 |
| Corynebacterium xerosis | 373 | 3.8 |
| Deinococcus radiodurans | 35073 | 6.0 |
| Derxia gummosa | 15994 | 61 |
| Gardnerella vaginalis | 14018 | 2.0 |
| Hafnia alvei | 13337 | 72 |
| Lactobacillus acidophilus | 4356 | 50 |
| Moraxella osloensis | 19976 | 64 |
| Mycobacterium smegmatis | 14468 | 19 |
| Mycoplasma hominis | 14027 | 34 |
| Neisseria gonorrhoeae | 19424 | 71 |
| Rahnella aquatilis | 33071 | 77 |
| Rhodospirillum rubrum | 11170 | 1.5 |
| Vibrio parahaemolyticus | 17802 | 73 |
| Yersinia enterocolitica | 9610 | 76 |
| Human | | 2.0 |

Table 59 shows that probe 3 hybridizes to the RNA of bacteria commonly found in urine and does not detect yeast rRNA.

TABLE 59

HYBRIDIZATION OF BACTERIAL PROBE 3 TO RNA OF ORGANISMS FOUND IN URINE

| Organism | ATCC# | % Probe* Bound |
| --- | --- | --- |
| Candida albicans | 18804 | 1.4 |
| Candida krusei | 34135 | 1.5 |
| Candida parapsilosis | 22019 | 2.2 |
| Candida tropicalis | 750 | 2.6 |
| Citrobacter freundii | 8090 | 79 |
| Enterobacter aerogenes | 13048 | 40 |
| Enterobacter cloacae | 13047 | 44 |
| Escherichia coli | 11775 | 67 |
| Klebsiella oxytoca | 13182 | 38 |
| Klebsiella pnuemoniae | 13883 | 45 |
| Morganella morganii | 25830 | 57 |
| Proteus mirabilis | 29906 | 40 |
| Proteus vulgaris | 13315 | 51 |
| Providencia stuartii | 29914 | 54 |
| Pseudomonas aeruginosa | 10145 | 61 |
| Pseudomonas fluorescens | 13525 | 56 |
| Serratia marcescens | 13880 | 54 |
| Staphylococcus aureus | 12600 | 37 |
| Staphylococcus epidermis | 14990 | 20 |
| Streptococcus agalactiae | 13813 | 34 |
| Streptococcus faecalis | 19433 | 20 |
| Streptococcus faecium | 19434 | 47 |
| Torulopsis glabrata | 2001 | 1.9 |
| Ureaplasma urealyticum | 27618 | 26 |

Table 60 shows that probe 3 detects phylogenetically diverse bacteria and does not hybridize to human rRNA.

TABLE 60

HYBRIDIZATION OF BACTERIAL PROBE 3 TO RNAs OF A CROSS SECTION OF PHYLOGENETICALLY DIVERSE ORGANISMS

| Organism Name | ATCC# | % Probe Bound |
| --- | --- | --- |
| Acinetobacter calcoaceticus | 23055 | 69 |
| Bacillus subtilis | 6051 | 35 |
| Bacteroides fragilis | 23745 | 1.2 |
| Branhamella catarrhalis | 25238 | 43 |
| Campylobacter jejuni | 33560 | 55 |
| Chlamydia trachomatis | VR878 | 42 |
| Chromobacterium violaceum | 29094 | 69 |
| Clostridium perfringens | 13124 | 62 |
| Corynebacterium xerosis | 373 | 23 |
| Deinococcus radiodurans | 35073 | 30 |
| Derxia gummosa | 15994 | 67 |
| Gardnerella vaginalis | 14018 | 40 |
| Hafnia alvei | 13337 | 56 |
| Lactobacillus acidophilus | 4356 | 36 |
| Moraxella osloensis | 19976 | 64 |
| Mycobacterium smegmatis | 14468 | 77 |
| Mycoplasma hominis | 14027 | 1.5 |
| Neisseria gonorrhoeae | 19424 | 26 |
| Rahnella aquatilis | 33071 | 66 |
| Rhodospirillum rubrum | 11170 | 51 |
| Vibrio parahaemolyticus | 17802 | 68 |
| Yersinia enterocolitica | 9610 | 68 |
| Human | | 0.9 |

Table 61 shows that probe 4 hybridizes to the RNA of bacteria commonly found in urine and does not detect yeast rRNA.

TABLE 61

HYBRIDIZATION OF BACTERIAL PROBE 4 TO RNA OF ORGANISMS FOUND IN URINE.

| Organism | ATCC # | % Probe Bound |
| --- | --- | --- |
| Candida albicans | 18804 | 4.5 |
| Candida krusei | 34135 | 2.5 |
| Candida parapsilosis | 22019 | 2.7 |
| Candida tropicalis | 750 | 2.5 |
| Citrobacter freundii | 8090 | 55 |
| Enterobacter aerogenes | 13048 | 52 |
| Enterobacter cloacae | 13047 | 57 |
| Escherichia coli | 11775 | 70 |
| Klebsiella oxytoca | 13182 | 70 |
| Klebsiella pneumoniae | 13883 | 43 |
| Morganella morganii | 25830 | 74 |
| Proteus mirabilis | 29906 | 74 |
| Proteus vulgaris | 13315 | 73 |
| Providencia stuartii | 29914 | 73 |
| Pseudomonas aeruginosa | 10145 | 76 |
| Pseudomonas fluorescens | 13525 | 79 |
| Serratia marcescens | 13880 | 74 |
| Staphylococcus aureus | 12600 | 73 |
| Staphylococcus epidermidis | 14990 | 73 |
| Streptococcus agalactiae | 13813 | 70 |
| Streptococcus faecalis | 19433 | 37 |
| Streptococcus faecium | 19434 | 63 |
| Torulopsis glabrata | 2001 | 2.2 |
| Ureaplasma urealyticum | 27618 | 43 |

Table 62 shows that probe 4 detects phylogenetically diverse bacteria and does not hybridize to human rRNA.

TABLE 62

HYBRIDIZATION OF BACTERIAL PROBE 4 TO RNAs OF A CROSS SECTION OF PHYLOGENETICALLY DIVERSE ORGANISMS

| Organism Name | ATCC # | % Probe Bound |
| --- | --- | --- |
| Acinetobacter calcoaceticus | 23055 | 69 |
| Bacillus subtilis | 6051 | 55 |
| Bacteroides fragilis | 23745 | 3.0 |
| Branhamella catarrhalis | 25238 | 59 |
| Campylobacter jejuni | 33560 | 65 |
| Chlamydia trachomatis | VR878 | 50 |
| Chromobacterium violaceum | 29094 | 61 |
| Clostridium perfringens | 13124 | 57 |
| Corynebacterium xerosis | 373 | 9.5 |
| Deinococcus radiodurans | 35073 | 63 |
| Derxia gummosa | 15994 | 65 |
| Gardnerella vaginalis | 14018 | 57 |
| Hafnia alvei | 13337 | 67 |
| Lactobacillus acidophilus | 4356 | 68 |
| Moraxella osloensis | 19976 | 68 |
| Mycobacterium smegmatis | 14468 | 28 |
| Mycoplasma hominis | 14027 | 74 |
| Neisseria gonorrhoeae | 19424 | 76 |
| Rahnella aquatilis | 33071 | 68 |
| Rhodospirillum rubrum | 11170 | 59 |
| Vibrio parahaemolyticus | 17802 | 75 |
| Yersinia enterocolitica | 9610 | 74 |
| Human | | 2.8 |

Table 63 shows that probe 5 hybridizes to the RNA of bacteria commonly found in urine and does not detect yeast rRNA.

TABLE 63

HYBRIDIZATION OF BACTERIAL PROBE 5 TO RNA OF ORGANISMS FOUND IN URINE

| Organism | ATCC # | % Probe Bound |
|---|---|---|
| Candida albicans | 18804 | 1.8 |
| Candida krusei | 34135 | 1.7 |
| Candida parapsilosis | 22019 | 2.2 |
| Candida tropicalis | 750 | 1.8 |
| Citrobacter freundii | 8090 | 39 |
| Enterobacter aerogenes | 13048 | 38 |
| Enterobacter cloacae | 13047 | 43 |
| Escherichia coli | 11775 | 31 |
| Klebsiella oxytoca | 13182 | 38 |
| Klebsiella pneumoniae | 13883 | 66 |
| Morganella morganii | 25830 | 50 |
| Proteus mirabilis | 29906 | 44 |
| Proteus vulgaris | 13315 | 52 |
| Providencia stuartii | 29914 | 44 |
| Pseudomonas aeruginosa | 10145 | 47 |
| Pseudomonas fluorescens | 13525 | 25 |
| Serratia marcescens | 13880 | 35 |
| Staphylococcus aureus | 12600 | 26 |
| Staphylococcus epidermidis | 14990 | 37 |
| Streptococcus agalactiae | 13813 | 29 |
| Streptococcus faecalis | 19433 | 14 |
| Streptococcus faecium | 19434 | 33 |
| Torulopsis glabrata | 2001 | 2.2 |
| Ureaplasma urealyticum | 27618 | 73 |

Table 64 shows that probe 5 detects phylogenetically diverse bacteria and does not hybridize to human RNA.

TABLE 64

HYBRIDIZATION OF BACTERIAL PROBE 5 TO RNAs OF A CROSS SECTION OF PHYLOGENETICALLY DIVERSE ORGANISMS

| Organism | ATCC # | % Probe Bound |
|---|---|---|
| Acinetobacter calcoaceticus | 23055 | 20 |
| Bacillus subtilis | 6051 | 53 |
| Bacteroides fragilis | 23745 | 44 |
| Branhamella catarrhalis | 25238 | 22 |
| Campylobacter jejuni | 33560 | 35 |
| Chromobacterium violaceum | 29094 | 59 |
| Clostridium perfringens | 13124 | 63 |
| Corynebacterium xerosis | 373 | 1.7 |
| Deinococcus radiodurans | 35073 | 5.7 |
| Derxia gummosa | 15994 | 14 |
| Gardnerella vaginalis | 14018 | 1.6 |
| Hafnia alvei | 13337 | 44 |
| Lactobacillus acidophilus | 4356 | 1.5 |
| Moraxella osloensis | 19976 | 7.2 |
| Mycobacterium smegmatis | 14468 | 39 |
| Mycoplasma hominis | 14027 | 21 |
| Neisseria gonorrhoeae | 19424 | 40 |
| Rahnella aquatilis | 33071 | 55 |
| Rhodospirillum rubrum | 11170 | 17 |
| Vibrio parahaemolyticus | 17802 | 66 |
| Yersinia enterocolitica | 9610 | 64 |
| Human | | 1.6 |

Table 65 shows that probe 6 hybridizes to the RNA of bacteria commonly found in urine and does not detect yeast rRNA.

TABLE 65

HYBRIDIZATION OF BACTERIAL PROBE 6 TO RNA OF ORGANISMS FOUND IN URINE

| Organism | ATCC # | % Probe Bound |
|---|---|---|
| Candida albicans | 18804 | 3.0 |
| Candida krusei | 34135 | 2.0 |
| Candida parapsilosis | 22019 | 2.2 |
| Citrobacter freundii | 8090 | 54 |
| Enterobacter aerogenes | 13048 | 50 |
| Enterobacter cloacae | 13047 | 58 |
| Escherichia coli | 11775 | 63 |
| Klebsiella oxytoca | 13182 | 54 |
| Klebsiella pneumoniae | 13883 | 55 |
| Morganella morganii | 25830 | 60 |
| Proteus mirabilis | 29906 | 64 |
| Proteus vulgaris | 13315 | 67 |
| Providencia stuartii | 29914 | 64 |
| Pseudomonas aeruginosa | 10145 | 65 |
| Pseudomonas fluorescens | 13525 | 31 |
| Serratia marcescens | 13880 | 67 |
| Staphylococcus aureus | 12600 | 53 |
| Staphylococcus epidermidis | 14990 | 34 |
| Streptococcus agalactiae | 13813 | 31 |
| Streptococcus faecium | 19434 | 18 |
| Torulopsis glabrata | 2001 | 2.5 |

Table 66 shows that probe 6 detects some phylogenetically diverse bacteria and does not hybridize to human rRNA.

TABLE 66

HYBRIDIZATION OF BACTERIAL PROBE 5 TO RNAs OF A CROSS SECTION OF PHYLOGENETICALLY DIVERSE ORGANISMS

| Organism | ATCC # | % Probe Bound |
|---|---|---|
| Acinetobacter calcoaceticus | 23055 | 73 |
| Bacteroides fragilis | 23745 | 7.0 |
| Branhamella catarrhalis | 25238 | 4.0 |
| Deinococcus radiodurans | 35073 | 5.5 |
| Derxia gummosa | 15994 | 3.0 |
| Gardnerella vaginalis | 14018 | 2.0 |
| Hafnia alvei | 13337 | 3.5 |
| Lactobacillus acidophilus | 4356 | 17 |
| Moraxella osloensis | 19976 | 62 |
| Mycoplasma hominis | 14027 | 44 |
| Rahnella aquatilis | 33071 | 56 |
| Yersinia enterocolitica | 9610 | 50 |
| Human | | 4.0 |

Table 67 shows that probe 7 hybridizes to the RNA of bacteria commonly found in urine and does not detect yeast rRNA.

TABLE 67

HYBRIDIZATION OF BACTERIAL PROBE 7 TO RNA OF ORGANISMS FOUND IN URINE

| Organism | ATCC # | % Probe Bound |
|---|---|---|
| Candida albicans | 18804 | 2.1 |
| Candida krusei | 34135 | 2.0 |
| Candida tropicalis | 750 | 2.2 |
| Citrobacter freundii | 8090 | 67 |
| Enterobacter aerogenus | 13048 | 69 |
| Enterobacter cloacae | 13047 | 78 |
| Escherichia coli | 11775 | 75 |
| Klebsiella oxytoca | 13882 | 79 |
| Klebsiella pneumoniae | 13883 | 77 |
| Morganella morganii | 25830 | 76 |

TABLE 67-continued

HYBRIDIZATION OF BACTERIAL PROBE 7 TO RNA OF ORGANISMS FOUND IN URINE

| Organism | ATCC # | % Probe Bound |
|---|---|---|
| *Proteus mirabilis* | 29906 | 77 |
| *Proteus vulgaris* | 13315 | 79 |
| *Providencia stuartii* | 29914 | 64 |
| *Pseudomonas aeruginosa* | 10145 | 76 |
| *Pseudomonas fluorescens* | 13525 | 78 |
| *Serratia marcescens* | 13880 | 66 |
| *Staphylococcus aureus* | 12600 | 71 |
| *Staphylococcus epidermidis* | 14990 | 75 |
| *Streptococcus agalactiae* | 13813 | 70 |
| *Streptococcus faecalis* | 19433 | 58 |
| *Streptococcus faecium* | 19434 | 68 |
| *Torulopsis glabrata* | 2001 | 2.4 |
| *Ureaplasma urealyticum* | 27618 | 21 |

Table 68 shows that probe 7 detects phylogenetically diverse bacteria and does not hybridize to human rRNA.

TABLE 68

HYBRIDIZATION OF BACTERIAL PROBE 7 TO RNAs OF A CROSS SECTION OF PHYLOGENETICALLY DIVERSE ORGANISMS

| Organism | ATCC # | % Probe Bound |
|---|---|---|
| *Acinetobacter calcoaceticus* | 23055 | 86 |
| *Bacillus subtilis* | 6051 | 83 |
| *Bacteroides fragilis* | 23745 | 69 |
| *Branhamella catarrhalis* | 25238 | 74 |
| *Campylobacter jejuni* | 33560 | 5.3 |
| *Chlamydia trachomatis* | VR878 | 41 |
| *Chromobacterium violaceum* | 29094 | 69 |
| *Clostridium perfringens* | 13124 | 68 |
| *Corynebacterium xerosis* | 373 | 23 |
| *Deinococcus radiodurans* | 35073 | 70 |
| *Derxia gummosa* | 15994 | 69 |
| *Gardnerella vaginalis* | 14018 | 68 |
| *Hafnia alvei* | 13337 | 77 |
| *Moraxella osloensis* | 19976 | 68 |
| *Mycobacterium smegmatis* | 14468 | 64 |
| *Mycoplasma hominis* | 14027 | 4.0 |
| *Neisseria gonorrhoeae* | 19424 | 53 |
| *Rahnella aquatilis* | 33071 | 72 |
| *Rhodospirillum rubrum* | 11170 | 73 |
| *Vibrio parahaemolyticus* | 17802 | 67 |
| *Yersinia enterocolitica* | 9610 | 66 |
| Human | | 2.2 |

EXAMPLE 20

Fungi encompass a morphologically and physiologically diverse group of simple eucaryotic organisms. We estimate, using published sequences of three fungi, *Neurospora crassa*, PodosDora, and Saccharomyces, that the rRNA of fungi are 58–60% homologous to *E. coli* and 84–90% homologous to one another. Some fungi grow as single cells (yeasts), others as multinuclear filaments (molds) and still others can grow as either single cells or multicellular filaments (dimorphic fungi). Although many fungi are harmless inhabitants of their environments, others are harmful and cause disease. The presence of any fungi in some locations is undesirable or indicative of disease (e.g., culture media, pharmaceutical products, body fluids such as blood, urine or cerebrospinal fluid, and tissue biopsies). Low levels of fungi are considered acceptable in other products such as drinking water and food products. This has created the need for a means of detecting and quantitating fungi in a sample.

The current methods for detecting and quantifying fungi involve microscopic examination of samples and culture on different media. Although most yeasts can be grown from clinical samples in a matter of days, some filamentous fungi take up to four weeks culture time, after which special staining procedures, biochemical analysis and antigen tests are performed. The oligonucleotide sequences below, when used in a hybridization assay, detect the five yeasts most commonly isolated in the clinical setting, *Candida albicans, Torulopsis glabrata, Candida tropicalis, Candida parapsilosis* and *Candida krusei*. Five other fungi representing the Trichosporon, Blastomyces, Cryptococcus and Saccharomyces genera are also detected. The present invention allows one step detection of these organisms and, in relation to culture, reduces the time to identification or elimination of these fungi as the cause of an infection. This represents a significant improvement over prior art methods.

The four probes which hybridize to the organisms of interest were identified using 3 primers complementary to conserved regions on 18S or 28S rRNA. Sequence 1 was obtained using an 18S primer with the sequence 5'-AGA ATT TCA CCT CTG-3'. Sequence 2 was obtained using a 28S primer with the sequence 5'-CCT TCT CCC GAA GTT ACG G 3'. Sequences 3 and 4 were obtained with a 28S primer with the sequence 5'-TTC CGA CTT CCA TGG CCA CCG TCC-3'. The following sequences were characterized and shown to hybridize to fungal rRNA. The sequences of *Saccharomyces cerevisiae*, *Saccharomyces carlsbergensis*, *Escherichia coli* and human rRNA were used for comparison with the sequences of interest.

1. CCC GAC CGT CCC TAT TAA TCA TTA CGA TGG

2. CGA CTT GGC ATG AAA ACT ATT CCT TCC TGT GG

3. GCT CTT CAT TCA ATT GTC CAC GTT CAA TTA AGC AAC

AAG G

GCT CTG CAT TCA AAC GTC CGC GTT CAA TAA AGA AAC

AGG G

Sequence 1, from 18S rRNA, is 30 bases in length and has a Tm of 68° C. Sequence 2, from 23S rRNA, is 32 bases in length and has a Tm of 67° C. Sequence 3, from 23S rRNA, is 40 bases in length and has a Tm of 66° C. Sequence 4, from 23S rRNA, is 40 bases in length and has a Tm of 68° C. Sequence 1 hybridizes in the region corresponding to position 845–880 of *Saccharomyces cerevisiae* 18s rRNA. Sequence 2 hybridizes in the region corresponding to position 1960–2000 of Saccharomyces cerevisiae 28s rRNA and sequences 3 and 4 hybridize in the region of 1225–1270 of the 28s rRNA.

To demonstrate the reactivity and specificity of these probes for fungal RNA, they were used in hybridization assays. 32p_ or $^{125}$I-labeled oligonucleotide probes were mixed with purified RNA or RNA released from cells by standard lysis techniques in 0.2 ml of 0.48 M sodium phosphate pH 6.8, 1% sodium dodecyl sulfate, 1 mM EDTA, 1 mM EGTA and incubated at 60° C. for 2 hours. Following incubation, 5 ml of 2% hydroxyapatite, 0.12 M sodium phosphate pH 6.8, 0.02% sodium dodecyl sulfate was added and the samples incubated 10 minutes at 60° C. The samples were centrifuged and the supernatants removed. Five ml of 0.12 M sodium phosphate pH 6.8, 0.02% sodium dodecyl sulfate was added, the samples were mixed, centrifuged and the supernatants removed. The results are shown in Table 69. Probe 1 detects all ten fungi which were tested, probe 2 detects all six of the yeasts which were tested, probe 3 detects five of the six yeasts, and probe 4 detects *C. krusei* only. Thus probe 4 could be used to detect and identify *C. krusei* in samples, probe 1, 2 or combination of 3 and 4 could be used to detect the yeasts, and probe 1 could be used to detect any of the ten organisms listed in Table 69.

One potential use for these probes is to identify yeasts in urine samples or other normally sterile body fluids. The probes were hybridized to a panel of bacteria most commonly isolated from urine and shown not to react (Table 70). Table 71 shows that the probes do not hybridize to phylogenetically diverse bacteria or to human RNA.

TABLE 69

HYBRIDIZATION OF YEAST PROBES TO YEAST RNA

| | | % Probe Bound | | | |
|---|---|---|---|---|---|
| Organism | ATCC # | #1 | #2 | #3 | #4 |
| Blastomyces dermatitidis | C.I. | 25 | 1.4 | 1.5 | 1.5 |
| Candida albicans | 18804 | 40 | 63 | 56 | 2.0 |
| C. krusei | 34135 | 73 | 62 | 2.2 | 70 |
| C. parapsilosis | 22019 | 71 | 63 | 65 | 2.0 |
| C. tropicalis | 750 | 62 | 71 | 71 | 2.0 |
| Cryptococcus laurentii | C.I. | 43 | 1.4 | 1.5 | 1.5 |
| Cryptococcus neoformans | C.I. | 60 | 1.3 | 1.5 | 1.6 |
| Torulopsis glabrata | 2001 | 61 | 44 | 62 | 2.0 |
| Trichosporon beigelii | C.I. | 57 | 1.3 | 2.1 | 1.5 |
| Saccharomyces cerevisiae | C.I. | 41 | 67 | 53 | 1.9 |

C.I. = Clinical isolate

TABLE 70

HYBRIDIZATION OF FUNGAL PROBES 1–4 TO RNA OF ORGANISMS FOUND IN URINE

| | | % Probe Bound | | | |
|---|---|---|---|---|---|
| Organism | ATCC# | #1 | #2 | #3 | #4 |
| Citrobacter freundii | 8090 | 1.5 | 1.7 | 1.5 | 2.1 |
| Enterobacter aerogenes | 13048 | 2.5 | 1.9 | 2.0 | 2.0 |
| Enterobacter cloacae | 13047 | 2.5 | 1.6 | 2.6 | 2.0 |
| Escherichia coli | 11775 | 3.0 | 2.0 | 1.6 | 1.5 |
| Klebsiella oxytoca | 13182 | 2.5 | 2.2 | 2.5 | 2.0 |
| Klebsiella pneumoniae | 13883 | 2.5 | 2.2 | 2.1 | 2.0 |
| Morganella morganii | 25830 | 2.0 | 2.8 | 1.7 | 1.9 |
| Proteus mirabilis | 29906 | 2.5 | 1.9 | 2.3 | 2.0 |
| Proteus vulgaris | 13315 | 2.0 | 2.2 | 2.0 | 1.5 |
| Probidencia stuartii | 29914 | 3.0 | 1.7 | 2.8 | 2.0 |
| Pseudomonas aeruginosa | 10145 | 2.0 | 1.9 | 1.3 | 2.0 |
| Pseudomonas fluorescens | 13525 | 2.5 | 2.7 | 2.1 | 2.0 |
| Serratia marcescens | 13880 | 2.5 | 1.7 | 1.8 | 2.0 |
| Staphylococcus aureus | 12600 | 2.0 | 1.7 | 1.8 | 2.0 |
| Staphylococcus epidermidis | 14990 | 3.0 | 1.5 | 1.3 | 2.0 |
| Streptococcus agalactiae | 13813 | 2.5 | 1.9 | 1.3 | 2.5 |
| Streptococcus faecalis | 19433 | 1.7 | 3.3 | 3.5 | 1.9 |
| Streptococcus faecium | 19434 | 2.0 | 2.9 | 2.1 | 1.5 |
| Ureaplasma urealyticum | 27618 | 2.1 | 3.1 | 2.4 | 1.8 |

TABLE 71

HYBRIDIZATION OF FUNGAL PROBES 1–4 TO RNAs OF A CROSS SECTION OF PHYLOGENETICALLY DIVERSE ORGANISMS

| | | % Probe Bound | | | |
|---|---|---|---|---|---|
| Organism | ATCC# | #1 | #2 | #3 | #4 |
| Acinetobacter calcoaceticus | 23055 | 2.5 | 2.5 | 2.0 | 1.9 |
| Bacillus subtilis | 6051 | 2.0 | 2.8 | 2.4 | 2.4 |
| Bacteroides fragilis | 23745 | 2.0 | 2.2 | 2.5 | 2.3 |
| Branhamella catarrhalis | 25238 | 2.5 | 3.2 | 1.8 | 1.7 |
| Campylobacter jejuni | 33560 | 2.5 | 2.1 | 2.0 | 1.9 |
| Chlamydia trachomatis | VR878 | 3.1 | 3.1 | 1.8 | 2.7 |

TABLE 71-continued

HYBRIDIZATION OF FUNGAL PROBES 1–4 TO RNAs OF A CROSS SECTION OF PHYLOGENETICALLY DIVERSE ORGANISMS

| | | % Probe Bound | | | |
|---|---|---|---|---|---|
| Organism | ATCC# | #1 | #2 | #3 | #4 |
| Chromobacterium violaceum | 29094 | 2.5 | 1.7 | 2.0 | 2.2 |
| Clostridium perfringens | 13124 | 1.9 | 2.3 | 1.8 | 1.8 |
| Corynebacterium xerosis | 373 | 1.6 | 4.8 | 1.8 | 1.1 |
| Deinococcus radiodurans | 35073 | 2.0 | 1.6 | 2.1 | 0.8 |
| Derxia gummosa | 15994 | 3.0 | 1.5 | 1.7 | 1.8 |
| Gardnerella vaginalis | 14018 | 2.0 | 2.2 | 1.3 | 1.2 |
| Hafnia alvei | 13337 | 1.0 | 2.5 | 1.7 | 1.6 |
| Lactobacillus acidophilus | 4356 | 2.0 | 2.7 | 2.0 | 1.9 |
| Moraxella osloensis | 19976 | 2.0 | 2.1 | 1.9 | 1.8 |
| Mycobacterium smegmatis | 14468 | 1.6 | 1.8 | 1.8 | 1.7 |
| Mycoplasma hominis | 14027 | 1.5 | 1.8 | 1.6 | 1.5 |
| Neisseria gonorrhoeae | 19424 | 2.0 | 2.7 | 1.6 | 1.6 |
| Rahnella aquatilis | 33071 | 2.0 | 2.7 | 2.3 | 2.1 |
| Rhodospirillum rubrum | 11170 | 2.0 | 1.8 | 1.6 | 1.5 |
| Vibrio parahaemolyticus | 17802 | 2.5 | 3.1 | 1.7 | 1.6 |
| Yersinia enterocolitica | 9610 | 2.0 | 1.8 | 2.3 | 2.2 |
| Human | | 2.0 | 1.8 | 2.1 | 3.0 |

Two derivatives of probe 1 also were made:
CCCGACCGTCCCTATTAATCATTAC-GATGGTCCTAGAAAC
CCCGACCGTCCCTATTAATCATTACGATGG
The first derivative works well at 65° C., the second at 60° C.

EXAMPLE 21

Gonorrhea is one of the most commonly reported bacterial infections in the U.S., with over two million cases reported annually. This sexually transmitted disease usually results in anterior urethritis in males and involves the cervix in females. While severe complications and even sterility can occur in untreated individuals, asymptomatic infections are common, resulting in carriers who unknowingly spread the disease.

The causative agent, *Neisseria gonorrhoeae*, is a gram negative, oxidase positive diplococcus with stringent growth requirements. The method used for diagnosis depends on the site of infection and the patient symptoms. Gonococcal urethritis in males is diagnosed with good sensitivity and specificity using gram stain. Culture, requiring 24–72 hours, usually must be performed to confirm diagnosis of gonorrhea from all females and asymptomatic males. Following the detection of the organism from growth in culture, *Neisseria gonorrhoeae* must be identified by further tests such as carbohydrate degradation, coagglutination, fluorescent antibody screens or chromogenic enzyme substrate assays.

*Neisseria gonorrhoeae* is particularly difficult to detect and distinguish using a nucleic acid probe because it is very closely related to *N. meningitidis*. Data published in Kingsbury, D. T., *J. Bacteriol.* 94:870–874 (1967) shows a DNA:DNA homology for the two species of approximately 80–94%. Under guidelines established by the Ad Hoc Committee on Reconciliation of Approaches to Bacterial Systematics, *Int'l J. System. Bacteriol.* 37:463–464 (1987), the phylogenetic definition of a species generally means 70% or greater DNA:DNA homology. Despite the fact that these organisms may be considered to be the same species under established principles, we were able to make probes capable of distinguishing them.

As expected, the rRNA homology between *N. gonorrhoeae* and *N. meningitidis* is even greater because of known conserved regions. We noted a 1.0% difference between the 16S and a 1.1% difference between the 23S rRNA sequences of *N. gonorrhoeae* and *N. meningitidis* using our sequencing data.

Making a probe for *N. gonorrhoeae* was complicated by the fact that in some sites where *N. meningitidis* and *N. gonorrhoeae* differed, other Neisseria species were similar to *N. gonorrhoeae*. The few mismatches which exist between these two species are in the most variable regions, i.e., regions which vary not only between species, but also from strain to strain. Despite the fact that some believed the species could not be distinguished with nucleic acid probes at all, and others believed that rRNA was too conserved to be useful in probe diagnostics, we were able to make probes capable of differentiating *N. gonorrhoeae* and *N. meningitidis*.

The present invention has significant advantages over each of the prior art methods; the probes are more specific and much faster than culture methods. It also is believed that the probes are more sensitive, (i.e., able to detect a smaller number of organisms in a clinical sample) than prior art methods.

The primers used to identify these probe sequences had the following sequences:
1. GGCCGTTACCCCACCTACTAGCTAAT
2. GTATTACCGCGGCTGCTGGCAC
3. GCTCGTTGCGGGACTTAACCCACCAT Each of the rRNA sites chosen to target had at least two mismatches to *E. coli*, *N. meningitidis*, *N. cinerea*, *N. lactamica*, *N. mucosa*, and *Kingella kingae*.

Oligonucleotides complementary to sequences adjacent to the probe regions were synthesized and used in the hybridization mix according to Hogan et al., U.S. patent app. Ser. No. 124,975, to be filed Nov. 24, 1987, entitled "Means and Method for Enhancing Nucleic Acid Hybridization (the "helper" patent application).

The following sequences were characterized and shown to be specific for *Neisseria gonorrhoeae*. The phylogenetically nearest neighbors *Neisseria meningitidis*, *N. lactamica*, *N. cinerea*, *N. mucosa*, and *Kingella kingae* were used for comparison with the *N. gonorrhoeae* sequence.
1. CCG CCG CTA CCC GGT AC
2. TCA TCG GCC GCC GAT ATT GGC
3. GAG CAT TCC GCA CAT GTC AAAACC AGG TA Sequence 1, complementary to 16S rRNA in the region 125–150, is 17 bases in length and has a Tm of 56° C.
Sequence 2, complementary to 16S rRNA in the region 455–485, is 21 bases in length and has a Tm of 63° C.
Sequence 3, complementary to 16S rRNA in the region 980–1015, is 29 bases in length and has a Tm of 57° C.

The reactivity and specificity of the probes for *Neisseria gonorrhoeae* was demonstrated with a hybridization assay. The three oligonucleotide probes were iodinated and mixed with unlabeled oligonucleotides of sequence 5'-CCC CTG CTT TCC CTC TCT AGA CGT ATG CGG TAT TAG CTG ATC TTT CG-3' 5'-GCC TTT TCT TCC CTG ACA AAA GTC CTT TAC AAC CCG-3' 5'-GGC ACG TAG TTA GCC GGT GCT TAT TCT TCA GGT AC-3' and 5'-GGT TCT TCG CGT TGC ATC GAA TTA ATC CAC ATC ATC CAC CGC-3' and with purified RNA in 0.48 M sodium phosphate, ph6.8, 0.5% sodium dodecyl sulfate (SDS) and incubated at 60° C. for one hour. Following incubation, 4 ml of 2% hydroxyapatite, 0.12 M sodium phosphate pH6.8, 0.02% SDS was added and the mixture was incubated at 60° C. for 5 minutes. The samples were centrifuged and the supernatants were removed. Five ml of wash solution (0.12 M sodium phosphate pH6.8, 2% SDS) was added and the samples were mixed, centrifuged, and the supernatants removed. The amount of radioactivity bound to the hydroxyapatite was determined in a gamma counter.

Table 72 shows that the probes hybridize well to *N. gonorrhoeae* RNA and do not hybridize to the other species tested.

TABLE 72

HYBRIDIZATION OF *NEISSERIA GONORRHOEAE* PROBES 1–3 TO NEISSERIA AND KINGELLA RNAS

| Organisms | ATCC# | % Probe Bound |
|---|---|---|
| *Kingella kingae* | 23332 | 0.09 |
| *Neisseria cinerea* | 14685 | 0.04 |
| *N. gonorrhoeae* | 19424 | 48.4 |
| *N. lactamica* | 23970 | 0.07 |
| *N. meningitidis* serogroup A | 13077 | 0.04 |
| *N. meningitidis* serogroup B | 13090 | 0.04 |
| *N. meningitidis* serogroup C | 13102 | 0.04 |
| *N. mucosa* | 19696 | 0.07 |
| *N. subflava* | 14799 | 0.05 |

The following derivatives of Neisseria probes also have been made and used:
GAG GAT TCC GCA CAT GTC AAA ACC AGG
GAG GAT TCC GCA CAT GTC AAA ACC AGG TAA
CCC GCT ACC CGG TAC GTT C
CCG CTA CCC GGT ACG TTC.

Although the above examples of performance were determined using the standard assay format previously described, the specific probes may be used under a wide variety of experimental conditions. For example, additives may be included to the reaction solutions to provide optimal reaction conditions for accelerated hybridization. Such additives may include buffers, chelators, organic compounds and nucleic acid precipitating agents such as detergents, dihydroxybenzene, sodium dodecyl sulfate, sodium diisobutyl sulfosuccinate, sodium tetradecyl sulfate, sarkosyl and the alkali metal salts and ammonium salts of $SO\text{-}2_4$, $PO\text{-}3_4$, $Cl^{-1}$ and $HCOO^{-1}$. Such additives can be utilized by one skilled in the art to provide optimal conditions for the hybridization reaction to take place. These conditions for accelerated hybridization of single stranded nucleic acid molecules into double stranded molecules are the subject of the above-noted U.S. patent App. Ser. No. 627,795 filed Jul. 5, 1984, continuation filed Jun.4, 1987 (serial no. not yet assigned) and Ser. No. 816,711 filed Jan. 7, 1986, which are both entitled ACCELERATED NUCLEIC ACID REASSOCIATION METHOD.

The present invention can be carried out on nonviral organisms from purified samples or unpurified clinical samples such as sputum, feces, tissue, blood, spinal or synovial fluids serum, urine or other bodily fluids, or other samples such as environmental or food samples. Prior to cell breakage and hybridization, the cells can be suspended or placed in solution. In the case of the unpurified samples referred to above, the cells may remain intact and untreated in their own biological environment prior to the assay.

The probes of the present invention may be used in an assay either alone or in combination with different probes. Several individual probes also can be linked together during nucleic acid synthesis. This results in one probe molecule which contains multiple probe sequences, and therefore, multiple specificities. For example, a single nucleic acid molecule can be synthesized which contains both the *Mycobacterium avium* and the *Mycobacterium intracellulare* sequences described in Examples 1 and 2. When hybridized with either *M. avium* or *M. intracellulare* rRNA this probe will hybridize completely. If the two probe sequences were combined separately in an assay only one half of the mixed individual probes will hybridize with either *M. avium* or *M. intracellulare* rRNA. Other embodiments also may be practiced within the scope of the claims. For example, probes may be labelled using a variety of labels, as described within, and may be incorporated into diagnostic kits.

We claim:

1. A probe comprising an oligonculeotide 10 to 100 nucleotides in length able to hybridize to a *Neisseria gonorrhoeae* nucleic acid target region to form a detectable target:probe duplex under selective hybridization assay conditions, said target region corresponding to, or perfectly complementary to a nucleic acid corresponding to, a region selected from the group consisting of:

bases 125–150 of *E. coli* 16S rRNA and bases 980–1015 of *E. coli* 16S rRNA; wherein said oligonucleotide comprises a sequence which is at least 75% complementary to a target sequence of 10 contiguous nucleotides present in said target region and said oligonucleotide does not hybridize to nucleic acid from *Neisseria meningitidis* to form a detectable non-target:probe duplex under said hybridization conditions.

2. The probe of claim 1, wherein said oligonucleotide comprises a sequence selected from the group consisting of:

SEQ ID NO. 1, CCGCCGCTACCCGGTAC,

SEQ ID NO. 3, GAGCATTCCGCACATGTCAAAAC-CAGGTA,

SEQ ID NO. 4, GAGGATTCCGCACATGTCAAAAC-CAGG,

SEQ ID NO. 5, GAGGATTCCGCACATGTCAAAAC-CAGGTAA,

SEQ ID NO. 6, CCCGCTACCCGGTACGTTC, and

SEQ ID NO. 7, CCGCTACCCGGTACGTTC, and sequences fully complementary and of the same length thereto.

3. The probe of claim 1, wherein said target region corresponds to, or is perfectly complementary to a nucleic acid corresponding to, bases 125–150 of *E. coli* 16S rRNA.

4. The probe of claim 3, wherein said target region corresponds to bases 125–150 of *E. coli* 16S rRNA.

5. The probe of claim 3, wherein said target sequence of 10 continuous nucleotides is present in a nucleic acid sequence selected from the group consisting of:

SEQ ID NO: 6: CCCGCTACCCGGTACGTTC,

SEQ ID NO: 7: CCGCTACCCGGTACGTTC, and sequences perfectly complementary thereto.

6. The probe of claim 1, wherein said target region corresponds to, or is perfectly complementary to a nucleic acid corresponding to, bases 980–1015 of *E. coli* 16S rRNA.

7. The probe of claim 6, wherein said target region corresponds to bases 980–1015 of *E. coli* 16S rRNA.

8. The probe of claim 6, wherein said target sequence of 10 contiguous nucleotides is present in a nucleic acid sequence selected from the group consisting of:

SEQ ID NO: 4: GAGGATTCCGCACATGTCAAAAC-CAGG,

SEQ ID NO: 5: GAGGATTCCGCACATGTCAAAAC-CAGGTAA, and sequences perfectly complementary thereto.

9. The probe of any of claims 3–8, wherein said oligonucleotide comprises a sequence which is at least 90% complementary to said target sequence of 10 contiguous nucleotides.

10. The probe of claim 9, wherein said oligonucleotide comprises a sequence which is 100% complementary to said target sequence of 10 contiguous nucleotides.

11. The probe of claim 9, wherein said selective hybridization assay conditions comprise 0.12 M phosphate buffer containing equimolar amounts of $Na_2HPO_4$ and $NaH_2PO_4$, 1 mM EDTA and 0.02% sodium dodecyl sulfate at 65° C.

12. The probe of claim 9, wherein said oligonucleotide is 15–50 bases in length.

13. A probe comprising an oligonucleotide 15 to 100 nucleotides in length able to hybridize to a *Neisseria gonorrhoeae* nucleic acid target region to form a detectable target:probe duplex under selective hybridization assay conditions, said target-region corresponding to, or perfectly complementary to a nucleic acid corresponding to, a region selected from the group consisting of:

bases 125–150 of *E. coli* 16S. rRNA and bases 980–1015 of *E. coli* 16S rRNA; wherein said oligonucleotide comprises a sequence which is at least 75% complementary to a target sequence of 15 contiguous nucleotides present in said target region and said oligonucleotide does not hybridize to nucleic acid from *Neisseria meningitidis* to form a detectable non-target:probe duplex under said hybridization conditions.

14. The probe of claim 13, wherein said target region corresponds to, or is perfectly complementary to a nucleic acid corresponding to, bases 125–150 of *E. coli* 16S rRNA.

15. The probe of claim 14, wherein said target region corresponds to bases 125–150 of *E. coli* 16S rRNA.

16. The probe of claim 14, wherein said target sequence of 15 contiguous nucleotides is present in a nucleic acid sequence selected from the group consisting of:

SEQ ID NO: 6: CCCGCTACCCGGTACGTTC,

SEQ ID NO: 7: CCGCTACCCGGTACGTTC, and sequences perfectly complementary thereto.

17. The probe of claim 13, wherein said target region corresponds to, or is perfectly complementary to a nucleic acid corresponding to, bases 980–1015 of *E. coli* 16S rRNA.

18. The probe of claim 17, wherein said target region corresponds to bases 980–1015 of *E. coli* 16S rRNA.

19. The probe of claim 17, wherein said target sequence of 15 contiguous nucleotides is present in a nucleic acid sequence selected from the group consisting of:

SEQ ID NO: 4: GAGGATTCCGCACATGTCAAAAC-CAGG,

SEQ ID NO: 5: GAGGATTCCGCACATGTCAAAAC-CAGGTAA, and sequences perfectly complementary thereto.

20. The probe of any of claims 14–19, wherein said oligonucleotide comprises a sequence which is at least 90% complementary to said target sequence of 15 contiguous nucleotides.

21. The probe of claim 20, wherein said oligonucleotide comprises a sequence which is 100% complementary to said target sequence of 15 contiguous nucleotides.

22. The probe of any of claims 14–19, wherein said oligonucleotide is 15–50 bases in length.

23. The probe claim 22, wherein said oligonucleotide comprises a sequence which is at least 90% complementary to said target sequence of 15 contiguous nucleotides.

24. The probe of claim 23, wherein said oligonucleotide comprises a sequence which is 100% complementary to said target sequence of 15 contiguous nucleotides.

25. The probe of claim 22, wherein said selective hybridization assay conditions comprise 0.12 M phosphate buffer containing equimolar amounts of $Na_2HPO_4$ and $NaH_2PO_4$, 1 mM and 0.02% sodium dodecyl sulfate at 65° C.

* * * * *